(12) United States Patent
Aman et al.

(10) Patent No.: US 9,815,872 B2
(45) Date of Patent: Nov. 14, 2017

(54) TOXOID PEPTIDES DERIVED FROM PHENOL SOLUBLE MODULIN, DELTA TOXIN, SUPERANTIGENS, AND FUSIONS THEREOF

(71) Applicant: Integrated Biotherapeutics, Inc., Gaithersburg, MD (US)

(72) Inventors: Mohammad Javad Aman, Rockville, MD (US); Rajan Prasad Adhikari, Gaithersburg, MD (US); Sergey Shulenin, Point of Rocks, MD (US); Frederick Wayne Holtsberg, Taneytown, MD (US); Hatice Karauzum, Rockville, MD (US)

(73) Assignee: INTEGRATED BIOTHERAPEUTICS, INC., Rockville, MD (US)

( * ) Notice: Subject to any disclaimer, the term of this patent is extended or adjusted under 35 U.S.C. 154(b) by 0 days.

(21) Appl. No.: 14/899,993

(22) PCT Filed: Jun. 18, 2014

(86) PCT No.: PCT/US2014/042999
§ 371 (c)(1),
(2) Date: Dec. 18, 2015

(87) PCT Pub. No.: WO2014/205111
PCT Pub. Date: Dec. 24, 2014

(65) Prior Publication Data
US 2016/0185829 A1    Jun. 30, 2016

Related U.S. Application Data

(60) Provisional application No. 61/836,959, filed on Jun. 19, 2013.

(51) Int. Cl.
*C07K 14/31* (2006.01)
*A61K 39/085* (2006.01)
*A61K 38/00* (2006.01)
*A61K 39/00* (2006.01)

(52) U.S. Cl.
CPC ............ *C07K 14/31* (2013.01); *A61K 39/085* (2013.01); *A61K 38/00* (2013.01); *A61K 2039/55572* (2013.01); *A61K 2039/70* (2013.01)

(58) Field of Classification Search
None
See application file for complete search history.

(56) References Cited

U.S. PATENT DOCUMENTS

| | | | |
|---|---|---|---|
| 6,399,332 B1 | 6/2002 | Ulrich et al. | |
| 6,713,284 B2 | 3/2004 | Ulrich et al. | |
| 7,087,235 B2 * | 8/2006 | Ulrich | C07K 14/31 424/184.1 |
| 7,226,595 B2 * | 6/2007 | Antonsson | A61K 47/48369 424/178.1 |
| 7,378,257 B2 | 5/2008 | Ulrich et al. | |
| 7,750,132 B2 | 7/2010 | Ulrich | |
| 7,754,225 B2 | 7/2010 | Fattom et al. | |
| 8,067,202 B2 | 11/2011 | Ulrich et al. | |
| 2007/0087014 A1 * | 4/2007 | Pavliak | A61K 39/085 424/203.1 |
| 2010/0119477 A1 * | 5/2010 | Otto | G01N 33/56938 424/85.2 |

FOREIGN PATENT DOCUMENTS

| | | |
|---|---|---|
| WO | 2012109167 | 8/2012 |
| WO | 2013082558 | 6/2013 |
| WO | 2014205111 | 12/2014 |

OTHER PUBLICATIONS

Shylaja et al. Indian J Microbiol (Jul.-Sep. 2012) 52(3):449-455.*
Bavari, et al., Superantigen vaccines: a comparative study of genetically attenuated receptor-binding mutants of staphylococcal enterotoxin A, 1996, J Infect Dis.
Bavari and Ulrich, Staphylococcal enterotoxin A and toxic shock syndrome toxin compete with CD4 for human major histocompatibility complex class II binding, Infect Immun, 63 (2):423-429 (1995).
Todd et al., Toxic-shock syndrome associated with phage-group-I Staphylococci, Lancet 2, (8100):1116-1118 (1978).
Aarestrup, et al., "Frequency of alpha- and beta-haemolysin in *Staphylococcus aureus* of bovine and human origin—A comparison between pheno- and genotype and variation in phenotypic expression,"1999, APMIS, 107 (4):425-430.
Marrack et al., "The Staphylococcal Enterotoxins and Their Relatives," Science, vol. 248, No. 1, (1990).
McKenney D. et al., "Broadly Protective Vaccine for *Staphylococcus aureus* Based on an in Vivo-Expressed Antigen," Science, 284(5419):1523-1527, May 28, 1999 .
Verghese A. et al., "LY146032 in a Hamster Model of *Staphylococcus aureus* Pneumonia—Effect on in vivo Clearance and Mortality and in vitro Opsonophagocytic Killing," Chemotherapy. 34:497-503 (1988).
Kephart, et al. "Comparison of the Invesligational drug, LV146032, with vancomycin in experimental pneumonia due to methidillln-resistant *Staphylococcus aureus*," J Antimicrob Chemother. 21:33-9, (1988).
Enkhbaatar P. et al., "Novel Ovine Model of Methicillian-Resistant *Staphylococcus aures*—Induced Pneumonia and Sepsis," Shock 29(5):642-9 (2008) .

(Continued)

*Primary Examiner* — Oluwatosin Ogunbiyi
(74) *Attorney, Agent, or Firm* — Thompson Coburn LLP

(57) ABSTRACT

The present disclosure provides immunogenic compositions useful in prevention and treatment of *Staphylococcus aureus* infection. In particular, the disclosure provides delta toxin and phenol-soluble modulin peptides as well as mutants, fragments, variants or derivatives thereof. The disclosure further provides multivalent oligopeptides, fusion proteins comprising two or more staphylococcal proteins, e.g., DT, PSM, alpha hemolysin, leukocidin, superantigen, or any fragments, variants, derivatives, or mutants thereof fused together as a single polypeptide in any order.

11 Claims, 9 Drawing Sheets

(56) References Cited

OTHER PUBLICATIONS

Figure 1C:
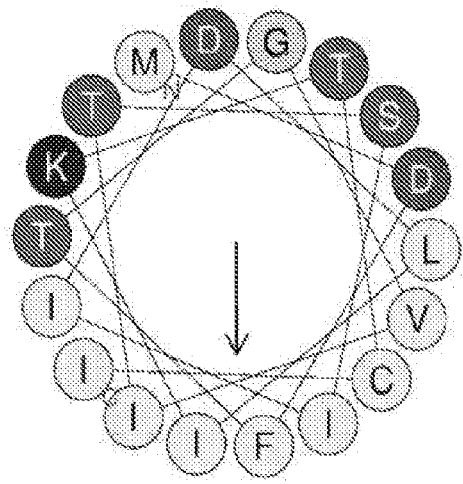

Boles, et al., Generation of protective immunity by inactivated recombinant staphylococcal enterotoxin B vaccine in nonhuman primates and identification of correlates of immunity 2003 Clin Immunol, 108 (1):51-59.

Boles, et al., Correlation of body temperature with protection against staphylococcal enterotoxin B exposure and use in determining vaccine dose-schedule, 2002, Vaccine, 21 (21-22):2791-2796.

Ulrich, et al., Development of engineered vaccines effective against structurally related bacterial superantigens, 1998, Vaccine, 16 (19):1857-1864.

Fournier et al., Isolation of Type 5 Capsular Polysaccharide From the *Staphyloccus aureus*, Ann. Inst. Pasteur/Microbiol., vol. 138, pp. 561-567 (1987).

Bubeck Wardenburg and Schneewind, Vaccine protection against *Staphylococcus aureus* pneumonia J Exp Med, 205 (2):287-294 (2008).

Wang et al., "*Staphylococcus epidermidis* surfactant peptides promote biofilm maturation and dissemination of biofilm-associated infection in mice," Nat. Med, 13 (12):1510-1514 (2007).

Novick et al., Synthesis of staphylococcal virulence factors is controlled by a regulatory RNA molecule EMBO Journal 12(10):3967-3975 (1993).

Adhikari et al, "Lower Antibody Levels to *Staphylococcus aureus* Exotoxins Are Associated With Sepsis in Hospitalized Adults With Invasive *S. aureus* Infections," J Infec Dis, 206 (6):915-923 (2012).

Bohach et al., "Staphylococcal and streptococcal pyrogenic toxins involved in toxic shock syndrome and related illnesses,"(1990) Crit Rev Microbiol.

Omoe et al., "Detection of seg, seh, and sei genes in *Staphylococcus aureus* Isolates and Determination of the Enterotoxin Productivities of *S. aureus* Isolates Harboring seg, seh, or sei Genes," (2002) J Clin Microbiol 40 (3):857-862.

Chatterjee et al., "Distribution and Regulation of the Mobile Genetic Element-Encoded Phenol-Soluble Modulin PSM-mec in Methicillin-Resistant *Staphylococcus aureus*," PLoS One, 6 (12):e28781 (2011).

Kaito et al., "Transcription and Translation Products of the Cytolysin Gene psm-mec on the Mobile Genetic Element SCCmec Regulate *Staphylococcus aureus* Virulence," PLoS Pathog, 7 (2):e1001267 (2011).

Cheung et al., "Direct and synergistic hemolysis caused by *Staphylococcus* phenol-soluble modulins: implications for diagnosis and pathogenesis," MicrbesInfect 14 (4):380-386 (2012).

Periasamy et al., "How *Staphylococcus aureus* biofilms develop their characteristic structure," Proc Natl Acad Sci 109 (4):1281-1286 (2012).

Novick, "Autoinduction and signal transduction in the regulation of staphylococcal virulence," Mol Microbiol 48 (6) 1429-1449 (2003).

Kreger et al., "Purification and Properties of Staphylococcal Delta Hemolysin," Infect Immun 3 (3):449-465 (1971).

Omae et al., "Inhibition of Colony-spreading Activity of *Staphylococcus aureus* by Secretion of δ-Hemolysin," J Biol Chem, 287 (19)15570-15579 (2012).

Giese et al., "Expression of δ-toxin by *Staphylococcus aureus* mediates escape from phago-endosomes of human epithelial and endothelial cells in the presence of β-toxin," Cell Microbiol 13 (2):316-329 (2011).

Schmitz et al., Delta-Toxin from *Staphylococcus aureus* as a Costimulator of Human Neutrophil Oxidative Burst (1997) J Infect Dis 176 (6):1531-1537.

Bhakdi and Tranum-Jensen, "Alpha-toxin of *Staphylococcus aureus*," 1991, Microbiol Rev, 55 (4):733-751.

McElroy, et al., "Alpha-toxin damages the air-blood barrier of the lung in a rat model of *Staphylococcus aureus* induced pneumonia," 1999, Infect Immun, 67 (10):5541-5544.

Brown and Pattee, "Identification of a chromosomal determinant of alpha-toxin production in *Staphylococcus aureus*," 1980, Infect Immun, 30 (1):36-42.

Husmann, et al., "Elimination of a bacterial pore-forming toxin by sequential endocytosis and exocytosis," 2009, FEBS Lett, 583 (2):337-344.

Shukla, et al., "Virulence genes and genotypic associations in nasal carriage, community-associated methicillin-susceptible and methicillin-resistant USA400 *Staphylococcus aureus*," 2010, J Clin Microbiol, 48 (10):3582-3592.

Gautier, et al., "HELIQUEST: a web server to screen sequences with specific α-helical properties," 2008, Bioinformatics, 24 (18):2101-2102.

Bubeck-Wardenburg J. et al., "Surface Proteins and Exotoxins Are Required for the Pathogenesis of *Staphylococcus aureus* Pneumonia," Infect Immun. 75:1040-4 (2007).

Menzies and Kernodle, "Passive immunization with antiserum to a nontoxic alpha-toxin mutant from *Staphylococcus aureus* is protective in a murine model," 1996; Infect Immun, 64 (5):1839-1841.

Adhikari, et al., "Novel structurally designed vaccine for *S. aureus* α-hemolysin: protection against bacteremia and pneumonia," 2012, PLoS One, 7 (6) : e38567.

Diep and Otto, "The role of virulence determinants in community-associated MRSA pathogenesis," Trends Microbiol, 16 (8):361-369 (2008).

Miles, et al., "Properties of Bacillus cereus hemolysin II: A heptameric transmembrane pore," 2002, Protein Sci, 11(4):894-902.

Karauzum, et al., Structurally Designed Attenuated Subunit Vaccines for *S. aureus* LukS-PV and LukF-PV Confer Protection in a Mouse Bacteremia Model2013, PLoS One, 8 (6):e65384.

Johns and Khan, "Staphylococcal enterotoxin B gene is associated with a discrete genetic element," 1988, J Bacteriol, 170 (9):4033-4039.

Choi, et al., "Interaction of *Staphylococcus aureus* toxin "superantigens" with human T cells," 1989, Proc Natl Acad Sci U S A, 86 (22):8941-8948.

O'Riordan and Lee, "*Staphylococcus aureus* Capsular Polysaccharides," Clinical Microbiology Reviews, Jan. 2004, p. 218-234, vol. 17, No. 1.

Poutrel and Sutra, "Type 5 and 8 capsular polysaccharides are expressed by *Staphylococcus aureus* isolates from rabbits, poultry, pigs, and horses," J Clin Microbiol. Feb. 1993;31(2):467-469.

Tollersrud et al., "Genetic and Serologic Evaluation of Capsule Production by Bovine Mammary Isolates of *Staphylococcus aureus* and Other *Staphylococcus* spp. from Europe and the United States," J Clin Microbiol. Aug. 2000;38(8):2998-3003.

Cunnion KM et al., "Capsule production and growth phase influence binding of complement to *Staphylococcus aureus*," Infect Immun. Nov. 2001;69(11):6796-803.

Wu and Park, "Chemical Characterization of a New Surface Antigenic Polysaccharide from a Mutant of *Staphylococcus aureus*," 1971. J. Bacterial. 108:874-884.

Fournier, J. M., et al., "Purification and characterization of *Staphylococcus aureus* type 8 capsular polysaccharide," Infect Immun. 45:87-93 (1984).

A Fattom et al., "Laboratory and clinical evaluation of conjugate vaccines composed of *Staphylococcus aureus* type 5 and type 8 capsular polysaccharides bound to *Pseudomonas aeruginosa* recombinant exoprotein A," Infect. Immun. Mar. 1993; 61(3):1023-1032, A Fattom et al., "A *Staphylococcus aureus* capsular polysaccharide (CP) vaccine and CP-specific antibodies protect mice against bacterial challenge," Infect. Immun. May 1996; 64(5):1659-1665, Lee et al., "Protective efficacy of antibodies to the *Staphylococcus aureus* type 5 capsular polysaccharide in a modified model of endocarditis in rats," Infect Immun. Oct. 1997; 65(10): 4146-4151.

Shinefield H et al., "Use of a *Staphylococcus aureus* conjugate vaccine in patients receiving hemodialysis," N Engl J Med. Feb. 14, 2002;346(7):491-6

Fattom Al et al., "Development of StaphVAX, a polysaccharide conjugate vaccine against *S. aureus* infection: from the lab bench to phase III clinical trials," Vaccine. Feb. 17, 2004;22(7):880-7.

Maira-Litran T et al, "Comparative Opsonic and Protective Activities of *Staphylococcus aureus* Conjugate Vaccines Containing Native or Deacetylated Staphylococcal Poly-N-Acetyl-β-(1-6)-Glucosamine," Infect Immun. Oct. 2005;73 (10):6752-62.

(56) References Cited

OTHER PUBLICATIONS

Tuchscherr LP. et al., "Antibodies to capsular polysaccharide and clumping factor A prevent mastitis and the emergence of unencapsulated and small-colony variants of *Staphylococcus aureus* in mice," Infect Immun. Dec. 2008;76(12):5738-44.
McKenney D. et al., "Vaccine potential of poly-1-6 beta-D-N-succinylglucosamine, an immunoprotective surface polysaccharide of *Staphylococcus aureus* and *Staphylococcus epidermidis*," J. Biotechnol. Sep. 29, 2000;83(1-2): 37-44.
Neuhaus, F.C. and J. Baddiley, "A continuum of anionic charge: structures and functions of D-alanyl-teichoic acids in gram-positive bacteria," Microbial Mol Biol Rev, 67(4):686-723(1998).
Thakker, M., et al., "*Staphylococcus aureus* serotype 5 capsular polysaccharide is antiphagocytic and enhances bacterial virulence in a murine bacteremia model," Infect Immun, 1998 66(11):5183-1589.
Yang, Z. et al. "Overcoming Immunity to a Viral Vaccine by DNA Priming before Vector Boosting," J Viral. 77:799-803, 2002.

\* cited by examiner

PSM alpha 1    PSM alpha 2    PSM alpha 3

Hydrophobic face :   Hydrophobic face :   Hydrophobic face :
V I L I F I I I I M   F I L I F I I I I M   F F L L F F V L F M PSM alpha 4    PSM beta 1    PSM beta 2    Delta Toxin Hydrophobic face :   Hydrophobic face :   Hydrophobic face :   Hydrophobic face :
I I I I I F I V I I M   L A I M V F   L A I M V A   I I I V V I I

Figure 1(a)

| Delta Toxin | | | | | | |
|---|---|---|---|---|---|---|
| Parameters | WT | ala | 2 ala | gly | 2 gly | gly ala |
| Hydrophobicity <H> | 0.65 | 0.57 | 0.52 | 0.55 | 0.49 | 0.50 |
| Hydrophobic moment <µH> | 0.62 | 0.58 | 0.53 | 0.57 | 0.51 | 0.52 |
| Wheel helix | | | | | | |
| PSM | | | | | | |
| Parameters | WT | ala | 2 ala | gly | 2 gly | gly ala |
| Hydrophobicity <H> | 0.63 | 0.55 | 0.50 | 0.56 | 0.47 | 0.49 |
| Hydrophobic moment <µH> | 0.71 | 0.67 | 0.62 | 0.65 | 0.59 | 0.60 |
| Wheel helix | | | | | | |

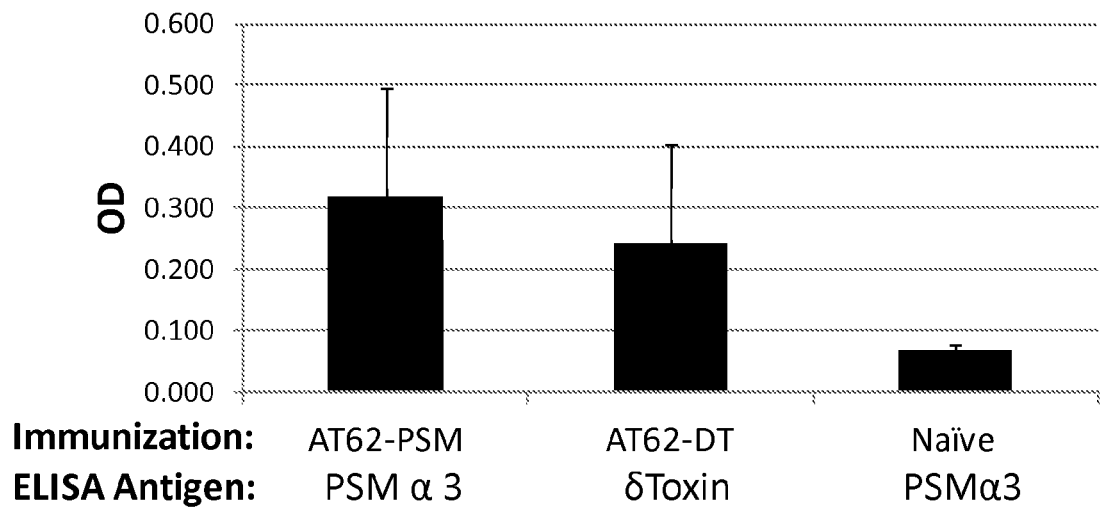
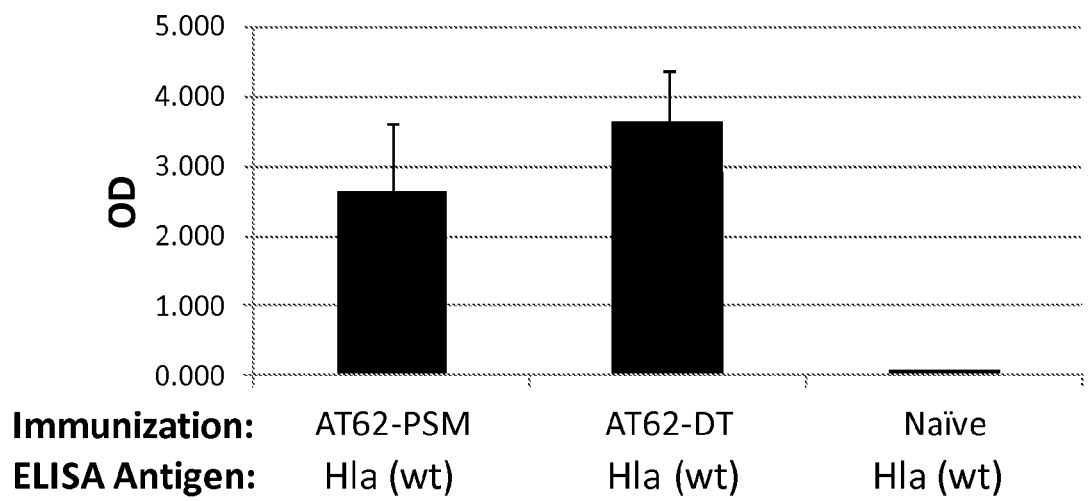
Figure 6

AT-62_rSEB:

rSEB_AT-62:

AT-62_rSEB_DT:

Figure 7

SEQUENCE LISTING

<160> NUMBER OF SEQ ID NOS: 66

<210> SEQ ID NO 1
<211> LENGTH: 26
<212> TYPE: PRT
<213> ORGANISM: Staphylococcus aureus

<400> SEQUENCE: 1

Met Ala Gln Asp Ile Ile Ser Thr Ile Gly Asp Leu Val Lys Trp Ile
1               5                   10                  15

Ile Asp Thr Val Asn Lys Phe Thr Lys Lys
            20                  25

```
<210> SEQ ID NO 2
<211> LENGTH: 26
<212> TYPE: PRT
<213> ORGANISM: Artificial
<220> FEATURE:
<223> OTHER INFORMATION: synthetic

<400> SEQUENCE: 2

Met Ala Gln Asp Ile Ile Ser Thr Ile Gly Asp Ala Val Lys Trp Ile
1               5                   10                  15

Ile Asp Thr Val Asn Lys Phe Thr Lys Lys
            20                  25

<210> SEQ ID NO 3
<211> LENGTH: 26
<212> TYPE: PRT
<213> ORGANISM: Artificial
<220> FEATURE:
<223> OTHER INFORMATION: synthetic

<400> SEQUENCE: 3

Met Ala Gln Asp Ile Ile Ser Thr Ile Gly Asp Ala Val Lys Trp Ile
1               5                   10                  15

Ile Asp Thr Ala Asn Lys Phe Thr Lys Lys
            20                  25

<210> SEQ ID NO 4
<211> LENGTH: 26
<212> TYPE: PRT
<213> ORGANISM: Artificial
<220> FEATURE:
<223> OTHER INFORMATION: synthetic

<400> SEQUENCE: 4

Met Ala Gln Asp Ile Ile Ser Thr Ile Gly Asp Gly Val Lys Trp Ile
1               5                   10                  15

Ile Asp Thr Val Asn Lys Phe Thr Lys Lys
            20                  25

<210> SEQ ID NO 5
<211> LENGTH: 26
<212> TYPE: PRT
<213> ORGANISM: Artificial
<220> FEATURE:
<223> OTHER INFORMATION: synthetic

<400> SEQUENCE: 5

Met Ala Gln Asp Ile Ile Ser Thr Ile Gly Asp Gly Val Lys Trp Ile
1               5                   10                  15

Ile Asp Thr Gly Asn Lys Phe Thr Lys Lys
            20                  25

<210> SEQ ID NO 6
<211> LENGTH: 22
<212> TYPE: PRT
<213> ORGANISM: Staphylococcus aureus

<400> SEQUENCE: 6

Met Glu Phe Val Ala Lys Leu Phe Lys Phe Phe Lys Asp Leu Leu Gly
1               5                   10                  15

Lys Phe Leu Gly Asn Asn
            20

<210> SEQ ID NO 7
```

<211> LENGTH: 22
<212> TYPE: PRT
<213> ORGANISM: Artificial
<220> FEATURE:
<223> OTHER INFORMATION: synthetic

<400> SEQUENCE: 7

```
Met Glu Phe Val Ala Lys Leu Phe Lys Phe Phe Lys Asp Ala Leu Gly
1               5                   10                  15

Lys Phe Leu Gly Asn Asn
            20
```

<210> SEQ ID NO 8
<211> LENGTH: 22
<212> TYPE: PRT
<213> ORGANISM: Artificial
<220> FEATURE:
<223> OTHER INFORMATION: synthetic

<400> SEQUENCE: 8

```
Met Glu Phe Ala Ala Lys Leu Phe Lys Phe Phe Lys Asp Ala Leu Gly
1               5                   10                  15

Lys Phe Leu Gly Asn Asn
            20
```

<210> SEQ ID NO 9
<211> LENGTH: 22
<212> TYPE: PRT
<213> ORGANISM: Artificial
<220> FEATURE:
<223> OTHER INFORMATION: synthetic

<400> SEQUENCE: 9

```
Met Glu Phe Val Ala Lys Leu Phe Lys Phe Phe Lys Asp Gly Leu Gly
1               5                   10                  15

Lys Phe Leu Gly Asn Asn
            20
```

<210> SEQ ID NO 10
<211> LENGTH: 22
<212> TYPE: PRT
<213> ORGANISM: Artificial
<220> FEATURE:
<223> OTHER INFORMATION: synthetic

<400> SEQUENCE: 10

```
Met Glu Phe Gly Ala Lys Leu Phe Lys Phe Phe Lys Asp Gly Leu Gly
1               5                   10                  15

Lys Phe Leu Gly Asn Asn
            20
```

<210> SEQ ID NO 11
<211> LENGTH: 22
<212> TYPE: PRT
<213> ORGANISM: Artificial
<220> FEATURE:
<223> OTHER INFORMATION: synthetic

<400> SEQUENCE: 11

```
Met Glu Phe Gly Ala Lys Leu Phe Lys Phe Phe Lys Asp Ala Leu Gly
1               5                   10                  15

Lys Phe Leu Gly Asn Asn
            20
```

-continued

<210> SEQ ID NO 12
<211> LENGTH: 21
<212> TYPE: PRT
<213> ORGANISM: Staphylococcus aureus

<400> SEQUENCE: 12

Met Gly Ile Ile Ala Gly Ile Ile Lys Phe Ile Lys Gly Leu Ile Glu
1               5                   10                  15
Lys Phe Thr Gly Lys
            20

<210> SEQ ID NO 13
<211> LENGTH: 22
<212> TYPE: PRT
<213> ORGANISM: Staphylococcus aureus

<400> SEQUENCE: 13

Met Glu Phe Val Ala Lys Leu Phe Lys Phe Phe Lys Asp Leu Leu Gly
1               5                   10                  15
Lys Phe Leu Gly Asn Asn
            20

<210> SEQ ID NO 14
<211> LENGTH: 20
<212> TYPE: PRT
<213> ORGANISM: Staphylococcus aureus

<400> SEQUENCE: 14

Met Ala Ile Val Gly Thr Ile Ile Lys Ile Ile Lys Ala Ile Ile Asp
1               5                   10                  15
Ile Phe Ala Lys
            20

<210> SEQ ID NO 15
<211> LENGTH: 44
<212> TYPE: PRT
<213> ORGANISM: Staphylococcus aureus

<400> SEQUENCE: 15

Met Glu Gly Leu Phe Asn Ala Ile Lys Asp Thr Val Thr Ala Ala Ile
1               5                   10                  15
Asn Asn Asp Gly Ala Lys Leu Gly Thr Ser Ile Val Asn Ile Val Glu
            20                  25                  30
Asn Gly Val Gly Leu Leu Ser Lys Leu Phe Gly Phe
        35                  40

<210> SEQ ID NO 16
<211> LENGTH: 44
<212> TYPE: PRT
<213> ORGANISM: Staphylococcus aureus

<400> SEQUENCE: 16

Met Thr Gly Leu Ala Glu Ala Ile Ala Asn Thr Val Gln Ala Ala Gln
1               5                   10                  15
Gln His Asp Ser Val Lys Leu Gly Thr Ser Ile Val Asp Ile Val Ala
            20                  25                  30
Asn Gly Val Gly Leu Leu Gly Lys Leu Phe Gly Phe
        35                  40

<210> SEQ ID NO 17
<211> LENGTH: 354
<212> TYPE: DNA

<213> ORGANISM: Artificial
<220> FEATURE:
<223> OTHER INFORMATION: synthetic

<400> SEQUENCE: 17

```
atggcggata gcgacatcaa catcaaaacg ggtactacgg acattggcag caatacgacc      60
gtcaagaccg gtgatctggt cacctatgac aaagagaatg gtatgcacaa aaaggtgttt     120
tacagcttca ttgatgacaa aaatcacaac aagaagctgt tggttattcg taccaaaggc     180
accattgccg gtggtggcgg ttccggcggt ggcggtagca tggcacagga catcatctct     240
accatcggcg atctggtgaa atggatcatt gataccgtta acaagttcac gaaaaagcat     300
catcaccatc accactgata actcgagcac caccaccacc accactgaga tccg           354
```

<210> SEQ ID NO 18
<211> LENGTH: 104
<212> TYPE: PRT
<213> ORGANISM: Artificial
<220> FEATURE:
<223> OTHER INFORMATION: synthetic

<400> SEQUENCE: 18

```
Ala Asp Ser Asp Ile Asn Ile Lys Thr Gly Thr Thr Asp Ile Gly Ser
1               5                   10                  15
Asn Thr Thr Val Lys Thr Gly Asp Leu Val Thr Tyr Asp Lys Glu Asn
                20                  25                  30
Gly Met His Lys Lys Val Phe Tyr Ser Phe Ile Asp Asp Lys Asn His
            35                  40                  45
Asn Lys Lys Leu Leu Val Ile Arg Thr Lys Gly Thr Ile Ala Gly Gly
        50                  55                  60
Gly Gly Ser Gly Gly Gly Gly Ser Met Ala Gln Asp Ile Ile Ser Thr
65                  70                  75                  80
Ile Gly Asp Leu Val Lys Trp Ile Ile Asp Thr Val Asn Lys Phe Thr
                85                  90                  95
Lys Lys His His His His His His
            100
```

<210> SEQ ID NO 19
<211> LENGTH: 311
<212> TYPE: DNA
<213> ORGANISM: Artificial
<220> FEATURE:
<223> OTHER INFORMATION: synthetic

<400> SEQUENCE: 19

```
atggcggata gcgacatcaa catcaaaacg ggtactacgg acattggcag caatacgacc      60
gtcaagaccg gtgatctggt cacctatgac aaagagaatg gtatgcacaa aaaggtgttt     120
tacagcttca ttgatgacaa aaatcacaac aagaagctgt tggttattcg taccaaaggc     180
accattgccg gtggtggcgg ctccggtggc ggtggttcta tggaatttgt tgcaaagctg     240
ttcaaattct ttaaggatct gctgggtaaa ttcctgggca caaccatca tcaccatcac     300
cactgataac t                                                          311
```

<210> SEQ ID NO 20
<211> LENGTH: 101
<212> TYPE: PRT
<213> ORGANISM: Artificial
<220> FEATURE:
<223> OTHER INFORMATION: synthetic

<400> SEQUENCE: 20

Met Ala Asp Ser Asp Ile Asn Ile Lys Thr Gly Thr Thr Asp Ile Gly
1               5                   10                  15

Ser Asn Thr Thr Val Lys Thr Gly Asp Leu Val Thr Tyr Asp Lys Glu
            20                  25                  30

Asn Gly Met His Lys Lys Val Phe Tyr Ser Phe Ile Asp Asp Lys Asn
        35                  40                  45

His Asn Lys Lys Leu Leu Val Ile Arg Thr Lys Gly Thr Ile Ala Gly
    50                  55                  60

Gly Gly Gly Ser Gly Gly Gly Ser Met Glu Phe Val Ala Lys Leu
65                  70                  75                  80

Phe Lys Phe Phe Lys Asp Leu Leu Gly Lys Phe Leu Gly Asn Asn His
                85                  90                  95

His His His His His
            100

<210> SEQ ID NO 21
<211> LENGTH: 387
<212> TYPE: DNA
<213> ORGANISM: Artificial
<220> FEATURE:
<223> OTHER INFORMATION: synthetic

<400> SEQUENCE: 21
atggcggata gcgacatcaa catcaaaacg ggtactacgg acattggcag caatacgacc      60
gtcaagaccg gtgatctggt cacctatgac aaagagaatg gtatgcacaa aaaggtgttt    120
tacagcttca ttgatgacaa aaatcacaac aagaagctgt tggttattcg taccaaaggc    180
accattgccg gtggtggtgg ttctatggcg caggacatca tttccacgat cggcgatctg    240
gttaaatgga tcatcgacac cgtgaacaag tttaccaaga aaggtggtgg cggtagcatg    300
gaatttgttg caaaactgtt caaattcttt aaggatctgc tgggcaagtt cctgggcaac    360
aatcatcatc accatcacca ctgataa                                        387

<210> SEQ ID NO 22
<211> LENGTH: 127
<212> TYPE: PRT
<213> ORGANISM: Artificial
<220> FEATURE:
<223> OTHER INFORMATION: synthetic

<400> SEQUENCE: 22

Met Ala Asp Ser Asp Ile Asn Ile Lys Thr Gly Thr Thr Asp Ile Gly
1               5                   10                  15

Ser Asn Thr Thr Val Lys Thr Gly Asp Leu Val Thr Tyr Asp Lys Glu
            20                  25                  30

Asn Gly Met His Lys Lys Val Phe Tyr Ser Phe Ile Asp Asp Lys Asn
        35                  40                  45

His Asn Lys Lys Leu Leu Val Ile Arg Thr Lys Gly Thr Ile Ala Gly
    50                  55                  60

Gly Gly Gly Ser Met Ala Gln Asp Ile Ile Ser Thr Ile Gly Asp Leu
65                  70                  75                  80

Val Lys Trp Ile Ile Asp Thr Val Asn Lys Phe Thr Lys Lys Gly Gly
                85                  90                  95

Gly Gly Ser Met Glu Phe Val Ala Lys Leu Phe Lys Phe Phe Lys Asp
            100                 105                 110

Leu Leu Gly Lys Phe Leu Gly Asn Asn His His His His His His

<210> SEQ ID NO 23
<211> LENGTH: 312
<212> TYPE: PRT
<213> ORGANISM: Artificial
<220> FEATURE:
<223> OTHER INFORMATION: synthetic

<400> SEQUENCE: 23

Met Ala Asp Ser Asp Ile Asn Ile Lys Thr Gly Thr Thr Asp Ile Gly
1               5                   10                  15

Ser Asn Thr Thr Val Lys Thr Gly Asp Leu Val Thr Tyr Asp Lys Glu
            20                  25                  30

Asn Gly Met His Lys Lys Val Phe Tyr Ser Phe Ile Asp Asp Lys Asn
        35                  40                  45

His Asn Lys Lys Leu Leu Val Ile Arg Thr Lys Gly Thr Ile Ala Gly
    50                  55                  60

Gly Gly Gly Ser Gly Gly Gly Ser Glu Ser Gln Pro Asp Pro Lys
65                  70                  75                  80

Pro Asp Glu Leu His Lys Ser Ser Lys Phe Thr Gly Leu Met Glu Asn
                85                  90                  95

Met Lys Val Leu Tyr Asp Asp Asn His Val Ser Ala Ile Asn Val Lys
            100                 105                 110

Ser Ile Asp Gln Phe Arg Tyr Phe Asp Leu Ile Tyr Ser Ile Lys Asp
        115                 120                 125

Thr Lys Leu Gly Asn Tyr Asp Asn Val Arg Val Glu Phe Lys Asn Lys
130                 135                 140

Asp Leu Ala Asp Lys Tyr Lys Asp Lys Tyr Val Asp Val Phe Gly Ala
145                 150                 155                 160

Asn Ala Tyr Tyr Gln Cys Ala Phe Ser Lys Lys Thr Asn Asp Ile Asn
                165                 170                 175

Ser His Gln Thr Asp Lys Arg Lys Thr Cys Met Tyr Gly Gly Val Thr
            180                 185                 190

Glu His Asn Gly Asn Gln Leu Asp Lys Tyr Arg Ser Ile Thr Val Arg
        195                 200                 205

Val Phe Glu Asp Gly Lys Asn Leu Leu Ser Phe Asp Val Gln Thr Asn
210                 215                 220

Lys Lys Lys Val Thr Ala Gln Glu Leu Asp Tyr Leu Thr Arg His Tyr
225                 230                 235                 240

Leu Val Lys Asn Lys Lys Leu Tyr Glu Phe Asn Asn Ser Pro Tyr Glu
                245                 250                 255

Thr Gly Tyr Ile Lys Phe Ile Glu Asn Glu Asn Ser Phe Trp Tyr Asp
            260                 265                 270

Met Met Pro Ala Pro Gly Asp Lys Phe Asp Gln Ser Lys Tyr Leu Met
        275                 280                 285

Met Tyr Asn Asp Asn Lys Met Val Asp Ser Lys Asp Val Lys Ile Glu
    290                 295                 300

Val Tyr Leu Thr Thr Lys Lys Lys
305                 310

<210> SEQ ID NO 24
<211> LENGTH: 948
<212> TYPE: DNA
<213> ORGANISM: Artificial
<220> FEATURE:
<223> OTHER INFORMATION: synthetic

<400> SEQUENCE: 24

```
catatggcag attctgatat taatattaaa accggtacta cagatattgg aagcaatact    60
acagtaaaaa caggtgattt agtcacttat gataaagaaa atggcatgca caaaaaagta   120
ttttatagtt ttatcgatga taaaaatcat aataaaaaac tgctagttat tagaacgaaa   180
ggtaccattg ctgggggagg ggggagcggg ggaggggga gcgagagtca accagatcct    240
aaaccagatg agttgcacaa atcgagtaaa ttcactggtt tgatggaaaa tatgaaagtt   300
ttgtatgatg ataatcatgt atcagcaata acgttaaat ctatagatca gtttcgttac    360
tttgacttaa tatattctat taaggacact aagttaggga attatgataa tgttcgagtc   420
gaatttaaaa acaaagattt agctgataaa tacaaagata aatacgtaga tgtgtttgga   480
gctaatgcgt attatcaatg tgcgttttct aaaaaaacga atgatattaa ttcgcatcaa   540
actgacaaac gaaaaacttg tatgtatggt ggtgtaactg agcataatgg aaaccaatta   600
gataaatata gaagtattac tgttcgggta tttgaagatg gtaaaaattt attatctttt   660
gacgtacaaa ctaataagaa aaaggtgact gctcaagaat tagattacct aactcgtcac   720
tatttggtga aaaataaaaa actctatgaa tttaacaact cgccttatga aacgggatat   780
attaaattta tagaaaatga aatagctttt ggtatgaca tgatgcctgc accaggagat   840
aaatttgacc aatctaaata tttaatgatg tacaatgaca ataaaatggt tgattctaaa   900
gatgtgaaga ttgaagttta tcttacgaca aagaaaaagt gaggatcc              948
```

<210> SEQ ID NO 25
<211> LENGTH: 948
<212> TYPE: DNA
<213> ORGANISM: Artificial
<220> FEATURE:
<223> OTHER INFORMATION: synthetic

<400> SEQUENCE: 25

```
catatggcag actcggacat caacatcaaa acgggcacga cggacattgg ctcaaacacg    60
acggtgaaaa cgggcgacct ggtgacctac gacaaagaaa acggcatgca taaaaaagtg   120
ttttatagct tcatcgatga caaaaaccac aacaaaaaac tgctggtcat tcgtaccaag   180
ggtacgatcg caggtggtgg tggttctggc ggtggtggta gtgaatccca gccggacccg   240
aaaccggacg aactgcataa aagctctaaa tttaccggcc tgatggaaaa tatgaaagtg   300
ctgtatgatg acaaccacgt gtcagccatt aatgttaaat cgatcgatca attccgttat   360
ttcgacctga tttactcaat caaagatacc aaactgggca actatgacaa tgtgcgcgtt   420
gaattcaaaa acaaagatct ggcagacaaa tacaaagata aatacgtcga cgtgttcggt   480
gcgaatgcct attaccagtg cgctttcagc aagaaaacca acgatatcaa ctctcatcaa   540
accgacaaac gtaaaacgtg tatgtatggc ggtgtgaccg aacacaacgg caatcagctg   600
gataaatacc gtagtatcac ggttcgcgtc tttgaagatg gtaaaaacct gctgtccttc   660
gatgtccaga ccaacaagaa aaagtgacg gcacaagaac tggattatct gacccgccat   720
tacctggtta aaacaaaaa actgtacgaa ttcaacaact caccgtatga aacgggctac   780
atcaaattca tcgaaaacga aaactcgttc ggtacgata tgatgccggc cccgggcgat   840
aaattcgacc agtccaaata tctgatgatg tacaatgata caaaatggt tgactccaaa   900
gatgtgaaaa tcgaagttta cctgacgacg aaaaaaaaat aaggatcc               948
```

<210> SEQ ID NO 26

<211> LENGTH: 312
<212> TYPE: PRT
<213> ORGANISM: Artificial
<220> FEATURE:
<223> OTHER INFORMATION: synthetic

<400> SEQUENCE: 26

Met Glu Ser Gln Pro Asp Pro Lys Pro Asp Glu Leu His Lys Ser Ser
1               5                   10                  15

Lys Phe Thr Gly Leu Met Glu Asn Met Lys Val Leu Tyr Asp Asp Asn
            20                  25                  30

His Val Ser Ala Ile Asn Val Lys Ser Ile Asp Gln Phe Arg Tyr Phe
        35                  40                  45

Asp Leu Ile Tyr Ser Ile Lys Asp Thr Lys Leu Gly Asn Tyr Asp Asn
    50                  55                  60

Val Arg Val Glu Phe Lys Asn Lys Asp Leu Ala Asp Lys Tyr Lys Asp
65                  70                  75                  80

Lys Tyr Val Asp Val Phe Gly Ala Asn Ala Tyr Tyr Gln Cys Ala Phe
                85                  90                  95

Ser Lys Lys Thr Asn Asp Ile Asn Ser His Gln Thr Asp Lys Arg Lys
            100                 105                 110

Thr Cys Met Tyr Gly Gly Val Thr Glu His Asn Gly Asn Gln Leu Asp
        115                 120                 125

Lys Tyr Arg Ser Ile Thr Val Arg Val Phe Glu Asp Gly Lys Asn Leu
    130                 135                 140

Leu Ser Phe Asp Val Gln Thr Asn Lys Lys Lys Val Thr Ala Gln Glu
145                 150                 155                 160

Leu Asp Tyr Leu Thr Arg His Tyr Leu Val Lys Asn Lys Lys Leu Tyr
                165                 170                 175

Glu Phe Asn Asn Ser Pro Tyr Glu Thr Gly Tyr Ile Lys Phe Ile Glu
            180                 185                 190

Asn Glu Asn Ser Phe Trp Tyr Asp Met Met Pro Ala Pro Gly Asp Lys
        195                 200                 205

Phe Asp Gln Ser Lys Tyr Leu Met Met Tyr Asn Asp Asn Lys Met Val
    210                 215                 220

Asp Ser Lys Asp Val Lys Ile Glu Val Tyr Leu Thr Thr Lys Lys Lys
225                 230                 235                 240

Gly Gly Gly Gly Ser Gly Gly Gly Ser Ala Asp Ser Asp Ile Asn
                245                 250                 255

Ile Lys Thr Gly Thr Thr Asp Ile Gly Ser Asn Thr Thr Val Lys Thr
            260                 265                 270

Gly Asp Leu Val Thr Tyr Asp Lys Glu Asn Gly Met His Lys Lys Val
        275                 280                 285

Phe Tyr Ser Phe Ile Asp Asp Lys Asn His Asn Lys Lys Leu Leu Val
    290                 295                 300

Ile Arg Thr Lys Gly Thr Ile Ala
305                 310

<210> SEQ ID NO 27
<211> LENGTH: 948
<212> TYPE: DNA
<213> ORGANISM: Artificial
<220> FEATURE:
<223> OTHER INFORMATION: synthetic

<400> SEQUENCE: 27
catatggaga gtcaaccaga tcctaaacca gatgagttgc acaaatcgag taaattcact    60

```
ggtttgatgg aaaatatgaa agttttgtat gatgataatc atgtatcagc aataaacgtt      120
aaatctatag atcagtttcg ttactttgac ttaatatatt ctattaagga cactaagtta      180
gggaattatg ataatgttcg agtcgaattt aaaaacaaag atttagctga taaatacaaa      240
gataaatacg tagatgtgtt tggagctaat gcgtattatc aatgtgcgtt ttctaaaaaa      300
acgaatgata ttaattcgca tcaaactgac aaacgaaaaa cttgtatgta tggtggtgta      360
actgagcata atgaaaacca attagataaa tatagaagta ttactgttcg ggtatttgaa      420
gatggtaaaa atttattatc ttttgacgta caaactaata agaaaaaggt gactgctcaa      480
gaattagatt acctaactcg tcactatttg gtgaaaaata aaaaactcta tgaatttaac      540
aactcgcctt atgaaacggg atatattaaa tttatagaaa atgagaatag cttttggtat      600
gacatgatgc ctgcaccagg agataaattt gaccaatcta atatttaat gatgtacaat       660 gacaataaaa tggttgattc taaagatgtg aagattgaag tttatcttac gacaaagaaa      720
aaggggggag gggggagcgg gggaggggg agcgcagatt ctgatattaa tattaaaacc       780
ggtactacag atattggaag caatactaca gtaaaaacag gtgatttagt cacttatgat      840
aaagaaaatg gcatgcacaa aaaagtattt tatagtttta tcgatgataa aaatcataat      900
aaaaaactgc tagttattag aacgaaaggt accattgctt gaggatcc                  948
```

<210> SEQ ID NO 28
<211> LENGTH: 948
<212> TYPE: DNA
<213> ORGANISM: Artificial
<220> FEATURE:
<223> OTHER INFORMATION: synthetic

<400> SEQUENCE: 28

```
catatggaaa gccaaccgga cccgaaaccg gacgaactgc ataaaagctc aaaattcacg       60
ggcctgatgg aaaacatgaa agtgctgtac gacgataacc atgtcagtgc aattaatgtg      120
aaatccatcg atcagtttcg ttatttcgac ctgatttact caatcaaaga taccaaactg      180
ggcaactatg acaatgtgcg cgttgaattc aaaaacaaag atctggcaga caaatacaaa      240
gataaatacg tcgacgtgtt cggtgcgaat gcctattacc agtgcgcttt cagcaagaaa      300
accaacgata ttaattcgca tcaaaccgac aaacgtaaaa cgtgtatgta tggcggtgtc      360
accgaacaca acggcaatca actggataaa taccgtagca tcacggttcg cgtcttttgaa     420 gatggtaaaa acctgctgtc tttcgacgtg cagaccaaca agaaaaaagt tacggcgcaa      480
gaactggatt atctgacccg ccattacctg gttaaaaaca aaaaactgta cgaattcaac      540
aactcaccgt atgaaacggg ctacatcaaa ttcatcgaaa acgaaaactc gttctggtac      600
gatatgatgc cggccccggg cgataaattc gaccagagta atacctgat gatgtacaac       660 gataacaaaa tggtggattc caaagacgtg aaaattgaag tttatctgac caccaagaaa      720
aaaggtggtg gtggtagcgg tggtggtggt agcgccgatt ctgacattaa catcaaaacc      780
ggcaccacgg atatcggttc taataccacg gttaaaaccg gcgatctggt cacgtatgac      840
aaagaaaacg gtatgcacaa aaaagtgttt tattccttca ttgacgacaa aaatcacaac      900
aaaaaactgc tggttatccg cacgaaaggc accatcgcat aaggatcc                  948
```

<210> SEQ ID NO 29
<211> LENGTH: 338
<212> TYPE: PRT
<213> ORGANISM: Artificial
<220> FEATURE:

<223> OTHER INFORMATION: synthetic

<400> SEQUENCE: 29

```
Met Ala Asp Ser Asp Ile Asn Ile Lys Thr Gly Thr Thr Asp Ile Gly
1               5                   10                  15

Ser Asn Thr Thr Val Lys Thr Gly Asp Leu Val Thr Tyr Asp Lys Glu
            20                  25                  30

Asn Gly Met His Lys Lys Val Phe Tyr Ser Phe Ile Asp Asp Lys Asn
        35                  40                  45

His Asn Lys Lys Leu Leu Val Ile Arg Thr Lys Gly Thr Ile Ala Gly
    50                  55                  60

Gly Gly Gly Ser Glu Ser Gln Pro Asp Pro Lys Pro Asp Glu Leu His
65                  70                  75                  80

Lys Ser Ser Lys Phe Thr Gly Leu Met Glu Asn Met Lys Val Leu Tyr
                85                  90                  95

Asp Asp Asn His Val Ser Ala Ile Asn Val Lys Ser Ile Asp Gln Phe
            100                 105                 110

Arg Tyr Phe Asp Leu Ile Tyr Ser Ile Lys Asp Thr Lys Leu Gly Asn
        115                 120                 125

Tyr Asp Asn Val Arg Val Glu Phe Lys Asn Lys Asp Leu Ala Asp Lys
    130                 135                 140

Tyr Lys Asp Lys Tyr Val Asp Val Phe Gly Ala Asn Ala Tyr Tyr Gln
145                 150                 155                 160

Cys Ala Phe Ser Lys Lys Thr Asn Asp Ile Asn Ser His Gln Thr Asp
                165                 170                 175

Lys Arg Lys Thr Cys Met Tyr Gly Gly Val Thr Glu His Asn Gly Asn
            180                 185                 190

Gln Leu Asp Lys Tyr Arg Ser Ile Thr Val Arg Val Phe Glu Asp Gly
        195                 200                 205

Lys Asn Leu Leu Ser Phe Asp Val Gln Thr Asn Lys Lys Lys Val Thr
    210                 215                 220

Ala Gln Glu Leu Asp Tyr Leu Thr Arg His Tyr Leu Val Lys Asn Lys
225                 230                 235                 240

Lys Leu Tyr Glu Phe Asn Asn Ser Pro Tyr Glu Thr Gly Tyr Ile Lys
                245                 250                 255

Phe Ile Glu Asn Glu Asn Ser Phe Trp Tyr Asp Met Met Pro Ala Pro
            260                 265                 270

Gly Asp Lys Phe Asp Gln Ser Lys Tyr Leu Met Met Tyr Asn Asp Asn
        275                 280                 285

Lys Met Val Asp Ser Lys Asp Val Lys Ile Glu Val Tyr Leu Thr Thr
    290                 295                 300

Lys Lys Lys Gly Gly Gly Ser Met Ala Gln Asp Ile Ile Ser Thr
305                 310                 315                 320

Ile Gly Asp Leu Val Lys Trp Ile Ile Asp Thr Val Asn Lys Phe Thr
                325                 330                 335

Lys Lys
```

<210> SEQ ID NO 30
<211> LENGTH: 1026
<212> TYPE: DNA
<213> ORGANISM: Artificial
<220> FEATURE:
<223> OTHER INFORMATION: synthetic

<400> SEQUENCE: 30

```
catatggcag attctgatat taatattaaa accggtacta cagatattgg aagcaatact      60
acagtaaaaa caggtgattt agtcacttat gataaagaaa atggcatgca caaaaaagta     120
ttttatagtt ttatcgatga taaaaatcat aataaaaaac tgctagttat tagaacgaaa     180
ggtaccattg ctgggggagg ggggagcgag agtcaaccag atcctaaacc agatgagttg     240
cacaaatcga gtaaattcac tggtttgatg aaaatatga aagttttgta tgatgataat     300
catgtatcag caataaacgt taaatctata gatcagtttc gttactttga cttaatatat     360
tctattaagg acactaagtt agggaattat gataatgttc gagtcgaatt taaaaacaaa     420
gatttagctg ataaatacaa agataaatac gtagatgtgt ttggagctaa tgcgtattat     480
caatgtgcgt tttctaaaaa aacgaatgat attaattcgc atcaaactga caaacgaaaa     540
acttgtatgt atggtggtgt aactgagcat aatggaaacc aattagataa atatagaagt     600
attactgttc gggtatttga agatggtaaa aatttattat cttttgacgt acaaactaat     660
aagaaaaagg tgactgctca agaattagat tacctaactc gtcactattt ggtgaaaaat     720
aaaaaactct atgaatttaa caactcgcct tatgaaacgg gatatattaa atttatagaa     780
aatgagaata gcttttggta tgacatgatg cctgcaccag agataaaatt tgaccaatct     840
aaatatttaa tgatgtacaa tgacaataaa atggttgatt ctaaagatgt gaagattgaa     900
gtttatctta cgacaagaa aaagggggga ggggggagca tggcacaaga tatcattca     960
acaatcggtg acttagtaaa atggattatc gacacagtga acaaattcac taaaaaatga    1020
ggatcc                                                                1026
```

<210> SEQ ID NO 31
<211> LENGTH: 1026
<212> TYPE: DNA
<213> ORGANISM: Artificial
<220> FEATURE:
<223> OTHER INFORMATION: synthetic

<400> SEQUENCE: 31

```
catatggcag atagcgacat caacatcaag acgggcacga cggacattgg ctcaaacacg      60
acggtgaaaa cgggtgacct ggttacctac gataaagaaa acggcatgca taagaaggtg     120
ttttattctt tcatcgatga caaaaaccac aataaaaagc tgctggttat tcgtaccaag     180
ggtacgattg cgggcggtgg cggtagtgaa tcccagccgg acccgaaacc ggacgaactg     240
cataagagct ctaaatttac cggcctgatg aaaatatga aagtgctgta tgatgacaac     300
cacgtctcag ccattaatgt gaaatcgatc gatcaatttc gttatttcga cctgatttac     360
agcatcaagg ataccaaact gggcaactac gacaatgtgc gcgttgaatt taaaaacaag     420
gatctggcag acaaatataa ggataaatac gtcgacgtgt ttggtgcgaa tgcctattac     480
cagtgcgctt tcagtaaaaa gaccaacgat atcaactccc atcaaaccga caagcgtaaa     540
acgtgtatgt atggcggtgt caccgaacac aacggcaatc agctggataa ataccgttca     600
atcacggttc gcgtctttga agatggtaaa aacctgctgt cgttcgatgt tcagaccaat     660
aaaaagaaag tcacggcaca agaactggat tatctgaccc gccattacct ggttaagaac     720
aagaagctgt acgaattcaa caacagtccg tatgaaacgg gctacatcaa gttcatcgaa     780
aacgaaaaca gcttctggta cgatatgatg ccggcaccgg tgataagtt cgaccagagc     840
aagtacctga tgatgtacaa cgataacaag atggttgatt ctaaggacgt gaaaatcgaa     900
gtttatctga ccacgaagaa aaagggcggt ggcggtagca tggctcaaga tattatctct     960
accatcggtg acctggtgaa gtggattatt gacacggtga acaagtttac gaagaaatga    1020
```

```
                                                             -continued ggatcc                                                                  1026

<210> SEQ ID NO 32
<211> LENGTH: 675
<212> TYPE: PRT
<213> ORGANISM: Artificial
<220> FEATURE:
<223> OTHER INFORMATION: synthetic

<400> SEQUENCE: 32

Met Glu Ser Gln Pro Asp Pro Lys Pro Asp Glu Leu His Lys Ser Ser
1               5                   10                  15

Lys Phe Thr Gly Leu Met Glu Asn Met Lys Val Leu Tyr Asp Asp Asn
                20                  25                  30

His Val Ser Ala Ile Asn Val Lys Ser Ile Asp Gln Phe Arg Tyr Phe
            35                  40                  45

Asp Leu Ile Tyr Ser Ile Lys Asp Thr Lys Leu Gly Asn Tyr Asp Asn
        50                  55                  60

Val Arg Val Glu Phe Lys Asn Lys Asp Leu Ala Asp Lys Tyr Lys Asp
65                  70                  75                  80

Lys Tyr Val Asp Val Phe Gly Ala Asn Ala Tyr Tyr Gln Cys Ala Phe
                85                  90                  95

Ser Lys Lys Thr Asn Asp Ile Asn Ser His Gln Thr Asp Lys Arg Lys
            100                 105                 110

Thr Cys Met Tyr Gly Gly Val Thr Glu His Asn Gly Asn Gln Leu Asp
        115                 120                 125

Lys Tyr Arg Ser Ile Thr Val Arg Val Phe Glu Asp Gly Lys Asn Leu
    130                 135                 140

Leu Ser Phe Asp Val Gln Thr Asn Lys Lys Lys Val Thr Ala Gln Glu
145                 150                 155                 160

Leu Asp Tyr Leu Thr Arg His Tyr Leu Val Lys Asn Lys Lys Leu Tyr
                165                 170                 175

Glu Phe Asn Asn Ser Pro Tyr Glu Thr Gly Tyr Ile Lys Phe Ile Glu
            180                 185                 190

Asn Glu Asn Ser Phe Trp Tyr Asp Met Met Pro Ala Pro Gly Asp Lys
        195                 200                 205

Phe Asp Gln Ser Lys Tyr Leu Met Met Tyr Asn Asp Asn Lys Met Val
    210                 215                 220

Asp Ser Lys Asp Val Lys Ile Glu Val Tyr Leu Thr Thr Lys Lys Lys
225                 230                 235                 240

Gly Gly Gly Ser Glu Lys Ser Glu Glu Ile Asn Glu Lys Asp Leu Arg
                245                 250                 255

Lys Lys Ser Glu Leu Gln Gly Thr Ala Leu Gly Asn Leu Lys Gln Ile
            260                 265                 270

Tyr Tyr Tyr Asn Glu Lys Ala Lys Thr Glu Asn Lys Glu Ser His Asp
        275                 280                 285

Gln Phe Arg Gln His Thr Ile Leu Phe Lys Gly Phe Phe Thr Asp His
    290                 295                 300

Ser Trp Tyr Asn Asp Leu Leu Val Arg Phe Asp Ser Lys Asp Ile Val
305                 310                 315                 320

Asp Lys Tyr Lys Gly Lys Lys Val Asp Leu Tyr Gly Ala Tyr Ala Gly
                325                 330                 335

Tyr Gln Cys Ala Gly Gly Thr Pro Asn Lys Thr Ala Cys Met Tyr Gly
            340                 345                 350
```

```
Gly Val Thr Leu His Asp Asn Asn Arg Leu Thr Glu Glu Lys Lys Val
            355                 360                 365

Pro Ile Asn Leu Trp Leu Asp Gly Lys Gln Asn Thr Val Pro Leu Glu
        370                 375                 380

Thr Val Lys Thr Asn Lys Lys Asn Val Thr Val Gln Glu Leu Asp Leu
385                 390                 395                 400

Gln Ala Arg Arg Tyr Leu Gln Glu Lys Tyr Asn Leu Tyr Asn Ser Asp
                405                 410                 415

Val Phe Asp Gly Lys Val Gln Arg Gly Leu Ile Val Phe His Thr Ser
            420                 425                 430

Thr Glu Pro Ser Val Asn Tyr Asp Leu Phe Gly Ala Gln Gly Gln Tyr
        435                 440                 445

Ser Asn Thr Leu Leu Arg Ile Tyr Arg Asp Asn Lys Thr Ile Asn Ser
    450                 455                 460

Glu Asn Met His Ile Asp Ile Tyr Leu Tyr Thr Ser Gly Gly Gly Gly
465                 470                 475                 480

Ser Ser Thr Asn Asp Asn Ile Lys Asp Leu Leu Asp Trp Tyr Ser Ser
                485                 490                 495

Gly Ser Asp Thr Phe Thr Asn Ser Glu Val Leu Ala Asn Ser Arg Gly
            500                 505                 510

Ser Met Arg Ile Lys Asn Thr Asp Gly Ser Ile Ser Leu Ile Ala Phe
        515                 520                 525

Pro Ser Pro Tyr Tyr Ser Pro Ala Phe Thr Lys Gly Glu Lys Val Asp
        530                 535                 540

Leu Asn Thr Lys Arg Thr Lys Lys Ser Gln His Thr Ser Glu Gly Thr
545                 550                 555                 560

Tyr Ile His Phe Gln Ile Ser Gly Val Thr Asn Thr Glu Lys Leu Pro
                565                 570                 575

Thr Pro Ile Glu Leu Pro Leu Lys Val Lys Val His Gly Lys Asp Ser
            580                 585                 590

Pro Leu Lys Tyr Trp Pro Lys Phe Asp Lys Gln Leu Ala Ile Ser
        595                 600                 605

Thr Leu Asp Phe Glu Ile Arg His Gln Leu Thr Gln Ile His Gly Leu
        610                 615                 620

Tyr Arg Ser Ser Asp Lys Thr Gly Gly Tyr Trp Lys Ile Thr Met Asn
625                 630                 635                 640

Asp Gly Ser Thr Tyr Gln Ser Asp Leu Ser Lys Lys Phe Glu Tyr Asn
                645                 650                 655

Thr Glu Lys Pro Pro Ile Asn Ile Asp Glu Ile Lys Thr Ile Glu Ala
            660                 665                 670

Glu Ile Asn
        675

<210> SEQ ID NO 33
<211> LENGTH: 675
<212> TYPE: PRT
<213> ORGANISM: Artificial
<220> FEATURE:
<223> OTHER INFORMATION: synthetic

<400> SEQUENCE: 33

Met Glu Ser Gln Pro Asp Pro Lys Pro Asp Glu Leu His Lys Ser Ser
1               5                   10                  15

Lys Phe Thr Gly Leu Met Glu Asn Met Lys Val Leu Tyr Asp Asp Asn
                20                  25                  30
```

-continued

His Val Ser Ala Ile Asn Val Lys Ser Ile Asp Gln Phe Arg Tyr Phe
            35                  40                  45

Asp Leu Ile Tyr Ser Ile Lys Asp Thr Lys Leu Gly Asn Tyr Asp Asn
 50                  55                  60

Val Arg Val Glu Phe Lys Asn Lys Asp Leu Ala Asp Lys Tyr Lys Asp
 65                  70                  75                  80

Lys Tyr Val Asp Val Phe Gly Ala Asn Ala Tyr Tyr Gln Cys Ala Phe
                 85                  90                  95

Ser Lys Lys Thr Asn Asp Ile Asn Ser His Gln Thr Asp Lys Arg Lys
             100                 105                 110

Thr Cys Met Tyr Gly Gly Val Thr Glu His Asn Gly Asn Gln Leu Asp
             115                 120                 125

Lys Tyr Arg Ser Ile Thr Val Arg Val Phe Glu Asp Gly Lys Asn Leu
 130                 135                 140

Leu Ser Phe Asp Val Gln Thr Asn Lys Lys Val Thr Ala Gln Glu
 145                 150                 155                 160

Leu Asp Tyr Leu Thr Arg His Tyr Leu Val Lys Asn Lys Lys Leu Tyr
                 165                 170                 175

Glu Phe Asn Asn Ser Pro Tyr Glu Thr Gly Tyr Ile Lys Phe Ile Glu
             180                 185                 190

Asn Glu Asn Ser Phe Trp Tyr Asp Met Met Pro Ala Pro Gly Asp Lys
             195                 200                 205

Phe Asp Gln Ser Lys Tyr Leu Met Met Tyr Asn Asp Asn Lys Met Val
 210                 215                 220

Asp Ser Lys Asp Val Lys Ile Glu Val Tyr Leu Thr Thr Lys Lys
 225                 230                 235                 240

Gly Gly Gly Ser Ser Thr Asn Asp Asn Ile Lys Asp Leu Leu Asp Trp
                 245                 250                 255

Tyr Ser Ser Gly Ser Asp Thr Phe Thr Asn Ser Glu Val Leu Ala Asn
             260                 265                 270

Ser Arg Gly Ser Met Arg Ile Lys Asn Thr Asp Gly Ser Ile Ser Leu
             275                 280                 285

Ile Ala Phe Pro Ser Pro Tyr Tyr Ser Pro Ala Phe Thr Lys Gly Glu
 290                 295                 300

Lys Val Asp Leu Asn Thr Lys Arg Thr Lys Lys Ser Gln His Thr Ser
 305                 310                 315                 320

Glu Gly Thr Tyr Ile His Phe Gln Ile Ser Gly Val Thr Asn Thr Glu
                 325                 330                 335

Lys Leu Pro Thr Pro Ile Glu Leu Pro Leu Lys Val Lys Val His Gly
             340                 345                 350

Lys Asp Ser Pro Leu Lys Tyr Trp Pro Lys Phe Asp Lys Lys Gln Leu
             355                 360                 365

Ala Ile Ser Thr Leu Asp Phe Glu Ile Arg His Gln Leu Thr Gln Ile
 370                 375                 380

His Gly Leu Tyr Arg Ser Ser Asp Lys Thr Gly Gly Tyr Trp Lys Ile
 385                 390                 395                 400

Thr Met Asn Asp Gly Ser Thr Tyr Gln Ser Asp Leu Ser Lys Lys Phe
                 405                 410                 415

Glu Tyr Asn Thr Glu Lys Pro Pro Ile Asn Ile Asp Glu Ile Lys Thr
             420                 425                 430

Ile Glu Ala Glu Ile Asn Gly Gly Gly Ser Glu Lys Ser Glu Glu
             435                 440                 445

Ile Asn Glu Lys Asp Leu Arg Lys Lys Ser Glu Leu Gln Gly Thr Ala

```
                450                 455                 460
Leu Gly Asn Leu Lys Gln Ile Tyr Tyr Tyr Asn Glu Lys Ala Lys Thr
465                 470                 475                 480

Glu Asn Lys Glu Ser His Asp Gln Phe Arg Gln His Thr Ile Leu Phe
                485                 490                 495

Lys Gly Phe Phe Thr Asp His Ser Trp Tyr Asn Asp Leu Leu Val Arg
                500                 505                 510

Phe Asp Ser Lys Asp Ile Val Asp Lys Tyr Lys Gly Lys Lys Val Asp
                515                 520                 525

Leu Tyr Gly Ala Tyr Ala Gly Tyr Gln Cys Ala Gly Gly Thr Pro Asn
                530                 535                 540

Lys Thr Ala Cys Met Tyr Gly Gly Val Thr Leu His Asp Asn Asn Arg
545                 550                 555                 560

Leu Thr Glu Glu Lys Lys Val Pro Ile Asn Leu Trp Leu Asp Gly Lys
                565                 570                 575

Gln Asn Thr Val Pro Leu Glu Thr Val Lys Thr Asn Lys Lys Asn Val
                580                 585                 590

Thr Val Gln Glu Leu Asp Leu Gln Ala Arg Arg Tyr Leu Gln Glu Lys
                595                 600                 605

Tyr Asn Leu Tyr Asn Ser Asp Val Phe Asp Gly Lys Val Gln Arg Gly
                610                 615                 620

Leu Ile Val Phe His Thr Ser Thr Glu Pro Ser Val Asn Tyr Asp Leu
625                 630                 635                 640

Phe Gly Ala Gln Gly Gln Tyr Ser Asn Thr Leu Leu Arg Ile Tyr Arg
                645                 650                 655

Asp Asn Lys Thr Ile Asn Ser Glu Asn Met His Ile Asp Ile Tyr Leu
                660                 665                 670

Tyr Thr Ser
        675

<210> SEQ ID NO 34
<211> LENGTH: 675
<212> TYPE: PRT
<213> ORGANISM: Artificial
<220> FEATURE:
<223> OTHER INFORMATION: synthetic

<400> SEQUENCE: 34

Met Glu Lys Ser Glu Ile Asn Glu Lys Asp Leu Arg Lys Lys Ser
1               5                   10                  15

Glu Leu Gln Gly Thr Ala Leu Gly Asn Leu Lys Gln Ile Tyr Tyr Tyr
                20                  25                  30

Asn Glu Lys Ala Lys Thr Glu Asn Lys Glu Ser His Asp Gln Phe Arg
                35                  40                  45

Gln His Thr Ile Leu Phe Lys Gly Phe Phe Thr Asp His Ser Trp Tyr
        50                  55                  60

Asn Asp Leu Leu Val Arg Phe Asp Ser Lys Asp Ile Val Asp Lys Tyr
65                  70                  75                  80

Lys Gly Lys Lys Val Asp Leu Tyr Gly Ala Tyr Ala Gly Tyr Gln Cys
                85                  90                  95

Ala Gly Gly Thr Pro Asn Lys Thr Ala Cys Met Tyr Gly Gly Val Thr
                100                 105                 110

Leu His Asp Asn Asn Arg Leu Thr Glu Glu Lys Lys Val Pro Ile Asn
                115                 120                 125

Leu Trp Leu Asp Gly Lys Gln Asn Thr Val Pro Leu Glu Thr Val Lys
```

```
                    130                 135                 140
Thr Asn Lys Lys Asn Val Thr Val Gln Glu Leu Asp Leu Gln Ala Arg
145                 150                 155                 160

Arg Tyr Leu Gln Glu Lys Tyr Asn Leu Tyr Asn Ser Asp Val Phe Asp
                    165                 170                 175

Gly Lys Val Gln Arg Gly Leu Ile Val Phe His Thr Ser Thr Glu Pro
                    180                 185                 190

Ser Val Asn Tyr Asp Leu Phe Gly Ala Gln Gly Gln Tyr Ser Asn Thr
                    195                 200                 205

Leu Leu Arg Ile Tyr Arg Asp Asn Lys Thr Ile Asn Ser Glu Asn Met
            210                 215                 220

His Ile Asp Ile Tyr Leu Tyr Thr Ser Gly Gly Gly Ser Glu Ser
225                 230                 235                 240

Gln Pro Asp Pro Lys Pro Asp Glu Leu His Lys Ser Ser Lys Phe Thr
                    245                 250                 255

Gly Leu Met Glu Asn Met Lys Val Leu Tyr Asp Asp Asn His Val Ser
                    260                 265                 270

Ala Ile Asn Val Lys Ser Ile Asp Gln Phe Arg Tyr Phe Asp Leu Ile
            275                 280                 285

Tyr Ser Ile Lys Asp Thr Lys Leu Gly Asn Tyr Asp Asn Val Arg Val
        290                 295                 300

Glu Phe Lys Asn Lys Asp Leu Ala Asp Lys Tyr Lys Asp Lys Tyr Val
305                 310                 315                 320

Asp Val Phe Gly Ala Asn Ala Tyr Tyr Gln Cys Ala Phe Ser Lys Lys
                    325                 330                 335

Thr Asn Asp Ile Asn Ser His Gln Thr Asp Lys Arg Lys Thr Cys Met
                    340                 345                 350

Tyr Gly Gly Val Thr Glu His Asn Gly Asn Gln Leu Asp Lys Tyr Arg
                    355                 360                 365

Ser Ile Thr Val Arg Val Phe Glu Asp Gly Lys Asn Leu Leu Ser Phe
            370                 375                 380

Asp Val Gln Thr Asn Lys Lys Lys Val Thr Ala Gln Glu Leu Asp Tyr
385                 390                 395                 400

Leu Thr Arg His Tyr Leu Val Lys Asn Lys Lys Leu Tyr Glu Phe Asn
                    405                 410                 415

Asn Ser Pro Tyr Glu Thr Gly Tyr Ile Lys Phe Ile Glu Asn Glu Asn
                    420                 425                 430

Ser Phe Trp Tyr Asp Met Met Pro Ala Pro Gly Asp Lys Phe Asp Gln
            435                 440                 445

Ser Lys Tyr Leu Met Met Tyr Asn Asp Asn Lys Met Val Asp Ser Lys
        450                 455                 460

Asp Val Lys Ile Glu Val Tyr Leu Thr Thr Lys Lys Gly Gly Gly
465                 470                 475                 480

Ser Ser Thr Asn Asp Asn Ile Lys Asp Leu Leu Asp Trp Tyr Ser Ser
                    485                 490                 495

Gly Ser Asp Thr Phe Thr Asn Ser Glu Val Leu Ala Asn Ser Arg Gly
                    500                 505                 510

Ser Met Arg Ile Lys Asn Thr Asp Gly Ser Ile Ser Leu Ile Ala Phe
            515                 520                 525

Pro Ser Pro Tyr Tyr Ser Pro Ala Phe Thr Lys Gly Glu Lys Val Asp
        530                 535                 540

Leu Asn Thr Lys Arg Thr Lys Lys Ser Gln His Thr Ser Glu Gly Thr
545                 550                 555                 560
```

Tyr Ile His Phe Gln Ile Ser Gly Val Thr Asn Thr Glu Lys Leu Pro
            565                 570                 575

Thr Pro Ile Glu Leu Pro Leu Lys Val Lys Val His Gly Lys Asp Ser
        580                 585                 590

Pro Leu Lys Tyr Trp Pro Lys Phe Asp Lys Lys Gln Leu Ala Ile Ser
            595                 600                 605

Thr Leu Asp Phe Glu Ile Arg His Gln Leu Thr Gln Ile His Gly Leu
        610                 615                 620

Tyr Arg Ser Ser Asp Lys Thr Gly Gly Tyr Trp Lys Ile Thr Met Asn
625                 630                 635                 640

Asp Gly Ser Thr Tyr Gln Ser Asp Leu Ser Lys Lys Phe Glu Tyr Asn
            645                 650                 655

Thr Glu Lys Pro Pro Ile Asn Ile Asp Glu Ile Lys Thr Ile Glu Ala
        660                 665                 670

Glu Ile Asn
    675

<210> SEQ ID NO 35
<211> LENGTH: 675
<212> TYPE: PRT
<213> ORGANISM: Artificial
<220> FEATURE:
<223> OTHER INFORMATION: synthetic

<400> SEQUENCE: 35

Met Glu Lys Ser Glu Glu Ile Asn Glu Lys Asp Leu Arg Lys Lys Ser
1               5                   10                  15

Glu Leu Gln Gly Thr Ala Leu Gly Asn Leu Lys Gln Ile Tyr Tyr Tyr
            20                  25                  30

Asn Glu Lys Ala Lys Thr Glu Asn Lys Glu Ser His Asp Gln Phe Arg
        35                  40                  45

Gln His Thr Ile Leu Phe Lys Gly Phe Phe Thr Asp His Ser Trp Tyr
    50                  55                  60

Asn Asp Leu Leu Val Arg Phe Asp Ser Lys Asp Ile Val Asp Lys Tyr
65                  70                  75                  80

Lys Gly Lys Lys Val Asp Leu Tyr Gly Ala Tyr Ala Gly Tyr Gln Cys
                85                  90                  95

Ala Gly Gly Thr Pro Asn Lys Thr Ala Cys Met Tyr Gly Gly Val Thr
            100                 105                 110

Leu His Asp Asn Asn Arg Leu Thr Glu Glu Lys Lys Val Pro Ile Asn
        115                 120                 125

Leu Trp Leu Asp Gly Lys Gln Asn Thr Val Pro Leu Glu Thr Val Lys
    130                 135                 140

Thr Asn Lys Lys Asn Val Thr Val Gln Glu Leu Asp Leu Gln Ala Arg
145                 150                 155                 160

Arg Tyr Leu Gln Glu Lys Tyr Asn Leu Tyr Asn Ser Asp Val Phe Asp
                165                 170                 175

Gly Lys Val Gln Arg Gly Leu Ile Val Phe His Thr Ser Thr Glu Pro
            180                 185                 190

Ser Val Asn Tyr Asp Leu Phe Gly Ala Gln Gly Gln Tyr Ser Asn Thr
        195                 200                 205

Leu Leu Arg Ile Tyr Arg Asp Asn Lys Thr Ile Asn Ser Glu Asn Met
    210                 215                 220

His Ile Asp Ile Tyr Leu Tyr Thr Ser Gly Gly Gly Gly Ser Ser Thr
225                 230                 235                 240

```
Asn Asp Asn Ile Lys Asp Leu Leu Asp Trp Tyr Ser Gly Ser Asp
                245                 250                 255

Thr Phe Thr Asn Ser Glu Val Leu Ala Asn Ser Arg Gly Ser Met Arg
                260                 265                 270

Ile Lys Asn Thr Asp Gly Ser Ile Ser Leu Ile Ala Phe Pro Ser Pro
                275                 280                 285

Tyr Tyr Ser Pro Ala Phe Thr Lys Gly Glu Lys Val Asp Leu Asn Thr
                290                 295                 300

Lys Arg Thr Lys Lys Ser Gln His Thr Ser Glu Gly Thr Tyr Ile His
305                 310                 315                 320

Phe Gln Ile Ser Gly Val Thr Asn Thr Glu Lys Leu Pro Thr Pro Ile
                325                 330                 335

Glu Leu Pro Leu Lys Val Lys Val His Gly Lys Asp Ser Pro Leu Lys
                340                 345                 350

Tyr Trp Pro Lys Phe Asp Lys Lys Gln Leu Ala Ile Ser Thr Leu Asp
                355                 360                 365

Phe Glu Ile Arg His Gln Leu Thr Gln Ile His Gly Leu Tyr Arg Ser
                370                 375                 380

Ser Asp Lys Thr Gly Gly Tyr Trp Lys Ile Thr Met Asn Asp Gly Ser
385                 390                 395                 400

Thr Tyr Gln Ser Asp Leu Ser Lys Lys Phe Glu Tyr Asn Thr Glu Lys
                405                 410                 415

Pro Pro Ile Asn Ile Asp Glu Ile Lys Thr Ile Glu Ala Glu Ile Asn
                420                 425                 430

Gly Gly Gly Ser Glu Ser Gln Pro Asp Pro Lys Pro Asp Glu Leu His
                435                 440                 445

Lys Ser Ser Lys Phe Thr Gly Leu Met Glu Asn Met Lys Val Leu Tyr
                450                 455                 460

Asp Asp Asn His Val Ser Ala Ile Asn Val Lys Ser Ile Asp Gln Phe
465                 470                 475                 480

Arg Tyr Phe Asp Leu Ile Tyr Ser Ile Lys Asp Thr Lys Leu Gly Asn
                485                 490                 495

Tyr Asp Asn Val Arg Val Glu Phe Lys Asn Lys Asp Leu Ala Asp Lys
                500                 505                 510

Tyr Lys Asp Lys Tyr Val Asp Val Phe Gly Ala Asn Ala Tyr Tyr Gln
                515                 520                 525

Cys Ala Phe Ser Lys Lys Thr Asn Asp Ile Asn Ser His Gln Thr Asp
                530                 535                 540

Lys Arg Lys Thr Cys Met Tyr Gly Gly Val Thr Glu His Asn Gly Asn
545                 550                 555                 560

Gln Leu Asp Lys Tyr Arg Ser Ile Thr Val Arg Val Phe Glu Asp Gly
                565                 570                 575

Lys Asn Leu Leu Ser Phe Asp Val Gln Thr Asn Lys Lys Lys Val Thr
                580                 585                 590

Ala Gln Glu Leu Asp Tyr Leu Thr Arg His Tyr Leu Val Lys Asn Lys
                595                 600                 605

Lys Leu Tyr Glu Phe Asn Asn Ser Pro Tyr Glu Thr Gly Tyr Ile Lys
                610                 615                 620

Phe Ile Glu Asn Glu Asn Ser Phe Trp Tyr Asp Met Met Pro Ala Pro
625                 630                 635                 640

Gly Asp Lys Phe Asp Gln Ser Lys Tyr Leu Met Met Tyr Asn Asp Asn
                645                 650                 655
```

```
Lys Met Val Asp Ser Lys Asp Val Lys Ile Glu Val Tyr Leu Thr Thr
            660                 665                 670

Lys Lys Lys
    675

<210> SEQ ID NO 36
<211> LENGTH: 675
<212> TYPE: PRT
<213> ORGANISM: Artificial
<220> FEATURE:
<223> OTHER INFORMATION: synthetic

<400> SEQUENCE: 36

Met Ser Thr Asn Asp Asn Ile Lys Asp Leu Leu Asp Trp Tyr Ser Ser
1               5                   10                  15

Gly Ser Asp Thr Phe Thr Asn Ser Glu Val Leu Ala Asn Ser Arg Gly
            20                  25                  30

Ser Met Arg Ile Lys Asn Thr Asp Gly Ser Ile Ser Leu Ile Ala Phe
        35                  40                  45

Pro Ser Pro Tyr Tyr Ser Pro Ala Phe Thr Lys Gly Glu Lys Val Asp
50              55                  60

Leu Asn Thr Lys Arg Thr Lys Lys Ser Gln His Thr Ser Glu Gly Thr
65                  70                  75                  80

Tyr Ile His Phe Gln Ile Ser Gly Val Thr Asn Thr Glu Lys Leu Pro
                85                  90                  95

Thr Pro Ile Glu Leu Pro Leu Lys Val Lys Val His Gly Lys Asp Ser
            100                 105                 110

Pro Leu Lys Tyr Trp Pro Lys Phe Asp Lys Lys Gln Leu Ala Ile Ser
        115                 120                 125

Thr Leu Asp Phe Glu Ile Arg His Gln Leu Thr Gln Ile His Gly Leu
130                 135                 140

Tyr Arg Ser Ser Asp Lys Thr Gly Gly Tyr Trp Lys Ile Thr Met Asn
145                 150                 155                 160

Asp Gly Ser Thr Tyr Gln Ser Asp Leu Ser Lys Lys Phe Glu Tyr Asn
                165                 170                 175

Thr Glu Lys Pro Pro Ile Asn Ile Asp Glu Ile Lys Thr Ile Glu Ala
            180                 185                 190

Glu Ile Asn Gly Gly Gly Ser Glu Lys Ser Glu Glu Ile Asn Glu Lys
        195                 200                 205

Asp Leu Arg Lys Lys Ser Glu Leu Gln Gly Thr Ala Leu Gly Asn Leu
210                 215                 220

Lys Gln Ile Tyr Tyr Tyr Asn Glu Lys Ala Lys Thr Glu Asn Lys Glu
225                 230                 235                 240

Ser His Asp Gln Phe Arg Gln His Thr Ile Leu Phe Lys Gly Phe Phe
                245                 250                 255

Thr Asp His Ser Trp Tyr Asn Asp Leu Leu Val Arg Phe Asp Ser Lys
            260                 265                 270

Asp Ile Val Asp Lys Tyr Lys Gly Lys Val Asp Leu Tyr Gly Ala
        275                 280                 285

Tyr Ala Gly Tyr Gln Cys Ala Gly Gly Thr Pro Asn Lys Thr Ala Cys
290                 295                 300

Met Tyr Gly Gly Val Thr Leu His Asp Asn Asn Arg Leu Thr Glu Glu
305                 310                 315                 320

Lys Lys Val Pro Ile Asn Leu Trp Leu Asp Gly Lys Gln Asn Thr Val
                325                 330                 335
```

Pro Leu Glu Thr Val Lys Thr Asn Lys Asn Val Thr Val Gln Glu
              340                 345                 350

Leu Asp Leu Gln Ala Arg Arg Tyr Leu Gln Glu Lys Tyr Asn Leu Tyr
355                 360                 365

Asn Ser Asp Val Phe Asp Gly Lys Val Gln Arg Gly Leu Ile Val Phe
        370                 375                 380

His Thr Ser Thr Glu Pro Ser Val Asn Tyr Asp Leu Phe Gly Ala Gln
385                 390                 395                 400

Gly Gln Tyr Ser Asn Thr Leu Leu Arg Ile Tyr Arg Asp Asn Lys Thr
                405                 410                 415

Ile Asn Ser Glu Asn Met His Ile Asp Ile Tyr Leu Tyr Thr Ser Gly
            420                 425                 430

Gly Gly Gly Ser Glu Ser Gln Pro Asp Pro Lys Pro Asp Glu Leu His
        435                 440                 445

Lys Ser Ser Lys Phe Thr Gly Leu Met Glu Asn Met Lys Val Leu Tyr
    450                 455                 460

Asp Asp Asn His Val Ser Ala Ile Asn Val Lys Ser Ile Asp Gln Phe
465                 470                 475                 480

Arg Tyr Phe Asp Leu Ile Tyr Ser Ile Lys Asp Thr Lys Leu Gly Asn
                485                 490                 495

Tyr Asp Asn Val Arg Val Glu Phe Lys Asn Lys Asp Leu Ala Asp Lys
            500                 505                 510

Tyr Lys Asp Lys Tyr Val Asp Val Phe Gly Ala Asn Ala Tyr Tyr Gln
        515                 520                 525

Cys Ala Phe Ser Lys Lys Thr Asn Asp Ile Asn Ser His Gln Thr Asp
530                 535                 540

Lys Arg Lys Thr Cys Met Tyr Gly Gly Val Thr Glu His Asn Gly Asn
545                 550                 555                 560

Gln Leu Asp Lys Tyr Arg Ser Ile Thr Val Arg Val Phe Glu Asp Gly
                565                 570                 575

Lys Asn Leu Leu Ser Phe Asp Val Gln Thr Asn Lys Lys Lys Val Thr
            580                 585                 590

Ala Gln Glu Leu Asp Tyr Leu Thr Arg His Tyr Leu Val Lys Asn Lys
        595                 600                 605

Lys Leu Tyr Glu Phe Asn Asn Ser Pro Tyr Glu Thr Gly Tyr Ile Lys
    610                 615                 620

Phe Ile Glu Asn Glu Asn Ser Phe Trp Tyr Asp Met Met Pro Ala Pro
625                 630                 635                 640

Gly Asp Lys Phe Asp Gln Ser Lys Tyr Leu Met Met Tyr Asn Asp Asn
                645                 650                 655

Lys Met Val Asp Ser Lys Asp Val Lys Ile Glu Val Tyr Leu Thr Thr
            660                 665                 670

Lys Lys Lys
    675

<210> SEQ ID NO 37
<211> LENGTH: 675
<212> TYPE: PRT
<213> ORGANISM: Artificial
<220> FEATURE:
<223> OTHER INFORMATION: synthetic

<400> SEQUENCE: 37

Met Ser Thr Asn Asp Asn Ile Lys Asp Leu Leu Asp Trp Tyr Ser Ser
1               5                   10                  15

Gly Ser Asp Thr Phe Thr Asn Ser Glu Val Leu Ala Asn Ser Arg Gly
            20                  25                  30

Ser Met Arg Ile Lys Asn Thr Asp Gly Ser Ile Ser Leu Ile Ala Phe
        35                  40                  45

Pro Ser Pro Tyr Tyr Ser Pro Ala Phe Thr Lys Gly Glu Lys Val Asp
    50                  55                  60

Leu Asn Thr Lys Arg Thr Lys Lys Ser Gln His Thr Ser Glu Gly Thr
65                  70                  75                  80

Tyr Ile His Phe Gln Ile Ser Gly Val Thr Asn Thr Glu Lys Leu Pro
                85                  90                  95

Thr Pro Ile Glu Leu Pro Leu Lys Val Lys Val His Gly Lys Asp Ser
            100                 105                 110

Pro Leu Lys Tyr Trp Pro Lys Phe Asp Lys Lys Gln Leu Ala Ile Ser
        115                 120                 125

Thr Leu Asp Phe Glu Ile Arg His Gln Leu Thr Gln Ile His Gly Leu
    130                 135                 140

Tyr Arg Ser Ser Asp Lys Thr Gly Gly Tyr Trp Lys Ile Thr Met Asn
145                 150                 155                 160

Asp Gly Ser Thr Tyr Gln Ser Asp Leu Ser Lys Lys Phe Glu Tyr Asn
                165                 170                 175

Thr Glu Lys Pro Pro Ile Asn Ile Asp Glu Ile Lys Thr Ile Glu Ala
            180                 185                 190

Glu Ile Asn Gly Gly Gly Ser Glu Ser Gln Pro Asp Pro Lys Pro
        195                 200                 205

Asp Glu Leu His Lys Ser Ser Lys Phe Thr Gly Leu Met Glu Asn Met
210                 215                 220

Lys Val Leu Tyr Asp Asp Asn His Val Ser Ala Ile Asn Val Lys Ser
225                 230                 235                 240

Ile Asp Gln Phe Arg Tyr Phe Asp Leu Ile Tyr Ser Ile Lys Asp Thr
                245                 250                 255

Lys Leu Gly Asn Tyr Asp Asn Val Arg Val Glu Phe Lys Asn Lys Asp
            260                 265                 270

Leu Ala Asp Lys Tyr Lys Asp Lys Tyr Val Asp Val Phe Gly Ala Asn
        275                 280                 285

Ala Tyr Tyr Gln Cys Ala Phe Ser Lys Lys Thr Asn Asp Ile Asn Ser
    290                 295                 300

His Gln Thr Asp Lys Arg Lys Thr Cys Met Tyr Gly Gly Val Thr Glu
305                 310                 315                 320

His Asn Gly Asn Gln Leu Asp Lys Tyr Arg Ser Ile Thr Val Arg Val
                325                 330                 335

Phe Glu Asp Gly Lys Asn Leu Leu Ser Phe Asp Val Gln Thr Asn Lys
            340                 345                 350

Lys Lys Val Thr Ala Gln Glu Leu Asp Tyr Leu Thr Arg His Tyr Leu
        355                 360                 365

Val Lys Asn Lys Lys Leu Tyr Glu Phe Asn Asn Ser Pro Tyr Glu Thr
    370                 375                 380

Gly Tyr Ile Lys Phe Ile Glu Asn Glu Asn Ser Phe Trp Tyr Asp Met
385                 390                 395                 400

Met Pro Ala Pro Gly Asp Lys Phe Asp Gln Ser Lys Tyr Leu Met Met
                405                 410                 415

Tyr Asn Asp Asn Lys Met Val Asp Ser Lys Asp Val Lys Ile Glu Val
            420                 425                 430

Tyr Leu Thr Thr Lys Lys Lys Gly Gly Gly Ser Glu Lys Ser Glu Glu

```
                435                 440                 445

Ile Asn Glu Lys Asp Leu Arg Lys Lys Ser Glu Leu Gln Gly Thr Ala
450                 455                 460

Leu Gly Asn Leu Lys Gln Ile Tyr Tyr Tyr Asn Glu Lys Ala Lys Thr
465                 470                 475                 480

Glu Asn Lys Glu Ser His Asp Gln Phe Arg Gln His Thr Ile Leu Phe
                485                 490                 495

Lys Gly Phe Phe Thr Asp His Ser Trp Tyr Asn Asp Leu Leu Val Arg
                500                 505                 510

Phe Asp Ser Lys Asp Ile Val Asp Lys Tyr Lys Gly Lys Lys Val Asp
                515                 520                 525

Leu Tyr Gly Ala Tyr Ala Gly Tyr Gln Cys Ala Gly Gly Thr Pro Asn
530                 535                 540

Lys Thr Ala Cys Met Tyr Gly Gly Val Thr Leu His Asp Asn Asn Arg
545                 550                 555                 560

Leu Thr Glu Glu Lys Lys Val Pro Ile Asn Leu Trp Leu Asp Gly Lys
                565                 570                 575

Gln Asn Thr Val Pro Leu Glu Thr Val Lys Thr Asn Lys Lys Asn Val
                580                 585                 590

Thr Val Gln Glu Leu Asp Leu Gln Ala Arg Arg Tyr Leu Gln Glu Lys
                595                 600                 605

Tyr Asn Leu Tyr Asn Ser Asp Val Phe Asp Gly Lys Val Gln Arg Gly
610                 615                 620

Leu Ile Val Phe His Thr Ser Thr Glu Pro Ser Val Asn Tyr Asp Leu
625                 630                 635                 640

Phe Gly Ala Gln Gly Gln Tyr Ser Asn Thr Leu Leu Arg Ile Tyr Arg
                645                 650                 655

Asp Asn Lys Thr Ile Asn Ser Glu Asn Met His Ile Asp Ile Tyr Leu
                660                 665                 670

Tyr Thr Ser
        675

<210> SEQ ID NO 38
<211> LENGTH: 21
<212> TYPE: PRT
<213> ORGANISM: Staphylococcus aureus

<400> SEQUENCE: 38

Met Gly Ile Ile Ala Gly Ile Ile Lys Val Ile Lys Ser Leu Ile Glu
1               5                   10                  15

Gln Phe Thr Gly Lys
            20

<210> SEQ ID NO 39
<211> LENGTH: 26
<212> TYPE: PRT
<213> ORGANISM: Artificial
<220> FEATURE:
<223> OTHER INFORMATION: synthetic
<220> FEATURE:
<221> NAME/KEY: VARIANT
<222> LOCATION: (5)..(5)
<223> OTHER INFORMATION: Xaa is isoleucine, glycine, or alanine
<220> FEATURE:
<221> NAME/KEY: VARIANT
<222> LOCATION: (6)..(6)
<223> OTHER INFORMATION: Xaa is isoleucine, glycine, or alanine
<220> FEATURE:
<221> NAME/KEY: VARIANT
<222> LOCATION: (9)..(9)
```

```
<223> OTHER INFORMATION: Xaa is isoleucine, glycine, or alanine
<220> FEATURE:
<221> NAME/KEY: VARIANT
<222> LOCATION: (12)..(12)
<223> OTHER INFORMATION: Xaa is leucine, glycine, or valine
<220> FEATURE:
<221> NAME/KEY: VARIANT
<222> LOCATION: (13)..(13)
<223> OTHER INFORMATION: Xaa is valine, glycine, or alanine
<220> FEATURE:
<221> NAME/KEY: VARIANT
<222> LOCATION: (16)..(16)
<223> OTHER INFORMATION: Xaa is  isoleucine, glycine, or alanine
<220> FEATURE:
<221> NAME/KEY: VARIANT
<222> LOCATION: (17)..(17)
<223> OTHER INFORMATION: Xaa is isoleucine, glycine, or alanine
<220> FEATURE:
<221> NAME/KEY: VARIANT
<222> LOCATION: (20)..(20)
<223> OTHER INFORMATION: Xaa is valine, glycine, or alanine

<400> SEQUENCE: 39

Met Ala Gln Asp Xaa Xaa Ser Thr Xaa Gly Asp Xaa Xaa Lys Trp Xaa
1               5                   10                  15

Xaa Asp Thr Xaa Asn Lys Phe Thr Lys Lys
            20                  25

<210> SEQ ID NO 40
<211> LENGTH: 21
<212> TYPE: PRT
<213> ORGANISM: Artificial
<220> FEATURE:
<223> OTHER INFORMATION: synthetic
<220> FEATURE:
<221> NAME/KEY: VARIANT
<222> LOCATION: (1)..(1)
<223> OTHER INFORMATION: Xaa is methionine, glycine, or alanine
<220> FEATURE:
<221> NAME/KEY: VARIANT
<222> LOCATION: (3)..(3)
<223> OTHER INFORMATION: Xaa is isoleucine, glycine, or alanine
<220> FEATURE:
<221> NAME/KEY: VARIANT
<222> LOCATION: (4)..(4)
<223> OTHER INFORMATION: Xaa is  isoleucine, glycine, or alanine
<220> FEATURE:
<221> NAME/KEY: VARIANT
<222> LOCATION: (7)..(7)
<223> OTHER INFORMATION: Xaa is  isoleucine, glycine, or alanine
<220> FEATURE:
<221> NAME/KEY: VARIANT
<222> LOCATION: (8)..(8)
<223> OTHER INFORMATION: Xaa is isoleucine, glycine, or alanine
<220> FEATURE:
<221> NAME/KEY: VARIANT
<222> LOCATION: (10)..(10)
<223> OTHER INFORMATION: Xaa is valine, glycine, or alanine
<220> FEATURE:
<221> NAME/KEY: VARIANT
<222> LOCATION: (11)..(11)
<223> OTHER INFORMATION: Xaa is isoleucine, glycine, or alanine
<220> FEATURE:
<221> NAME/KEY: VARIANT
<222> LOCATION: (14)..(14)
<223> OTHER INFORMATION: Xaa is  leucine, glycine, or alanine
<220> FEATURE:
<221> NAME/KEY: VARIANT
<222> LOCATION: (15)..(15)
<223> OTHER INFORMATION: Xaa is  isoleucine, glycine, or alanine
<220> FEATURE:
<221> NAME/KEY: VARIANT
<222> LOCATION: (18)..(18)
<223> OTHER INFORMATION: Xaa is phenylalanine, glycine, or alanine

<400> SEQUENCE: 40
```

```
Xaa Gly Xaa Xaa Ala Gly Xaa Xaa Lys Xaa Xaa Lys Ser Xaa Xaa Glu
1               5                   10                  15

Gln Xaa Thr Gly Lys
        20
```

<210> SEQ ID NO 41
<211> LENGTH: 21
<212> TYPE: PRT
<213> ORGANISM: Artificial
<220> FEATURE:
<223> OTHER INFORMATION: synthetic
<220> FEATURE:
<221> NAME/KEY: VARIANT
<222> LOCATION: (1)..(1)
<223> OTHER INFORMATION: Xaa is methionine, glycine, or alanine
<220> FEATURE:
<221> NAME/KEY: VARIANT
<222> LOCATION: (3)..(3)
<223> OTHER INFORMATION: Xaa is isoleucine, glycine, or alanine
<220> FEATURE:
<221> NAME/KEY: VARIANT
<222> LOCATION: (4)..(4)
<223> OTHER INFORMATION: Xaa is isoleucine, glycine, or alanine
<220> FEATURE:
<221> NAME/KEY: VARIANT
<222> LOCATION: (7)..(7)
<223> OTHER INFORMATION: Xaa is isoleucine, glycine, or alanine
<220> FEATURE:
<221> NAME/KEY: VARIANT
<222> LOCATION: (8)..(8)
<223> OTHER INFORMATION: Xaa is isoleucine, glycine, or alanine
<220> FEATURE:
<221> NAME/KEY: VARIANT
<222> LOCATION: (10)..(10)
<223> OTHER INFORMATION: Xaa is phenylalanine, glycine, or alanine
<220> FEATURE:
<221> NAME/KEY: VARIANT
<222> LOCATION: (11)..(11)
<223> OTHER INFORMATION: Xaa is isoleucine, glycine, or alanine
<220> FEATURE:
<221> NAME/KEY: VARIANT
<222> LOCATION: (14)..(14)
<223> OTHER INFORMATION: Xaa is leucine, glycine, or alanine
<220> FEATURE:
<221> NAME/KEY: VARIANT
<222> LOCATION: (15)..(15)
<223> OTHER INFORMATION: Xaa is isoleucine, glycine, or alanine
<220> FEATURE:
<221> NAME/KEY: VARIANT
<222> LOCATION: (18)..(18)
<223> OTHER INFORMATION: Xaa is phenylalanine, glycine, or alanine

<400> SEQUENCE: 41

```
Xaa Gly Xaa Xaa Ala Gly Xaa Xaa Lys Xaa Xaa Lys Gly Xaa Xaa Glu
1               5                   10                  15

Lys Xaa Thr Gly Lys
        20
```

<210> SEQ ID NO 42
<211> LENGTH: 22
<212> TYPE: PRT
<213> ORGANISM: Artificial
<220> FEATURE:
<223> OTHER INFORMATION: synthetic
<220> FEATURE:
<221> NAME/KEY: VARIANT
<222> LOCATION: (1)..(1)
<223> OTHER INFORMATION: Xaa is methionine, glycine, or alanine
<220> FEATURE:
<221> NAME/KEY: VARIANT
<222> LOCATION: (3)..(3)
<223> OTHER INFORMATION: Xaa is phenylalanine, glycine, or alanine
<220> FEATURE:

```
<221> NAME/KEY: VARIANT
<222> LOCATION: (4)..(4)
<223> OTHER INFORMATION: Xaa is valine, glycine, or alanine
<220> FEATURE:
<221> NAME/KEY: VARIANT
<222> LOCATION: (7)..(7)
<223> OTHER INFORMATION: Xaa is leucine, glycine, or alanine
<220> FEATURE:
<221> NAME/KEY: VARIANT
<222> LOCATION: (8)..(8)
<223> OTHER INFORMATION: Xaa is phenylalanine, glycine, or alanine
<220> FEATURE:
<221> NAME/KEY: VARIANT
<222> LOCATION: (10)..(10)
<223> OTHER INFORMATION: Xaa is phenylalanine, glycine, or alanine
<220> FEATURE:
<221> NAME/KEY: VARIANT
<222> LOCATION: (11)..(11)
<223> OTHER INFORMATION: Xaa is phenylalanine, glycine, or alanine
<220> FEATURE:
<221> NAME/KEY: VARIANT
<222> LOCATION: (14)..(14)
<223> OTHER INFORMATION: Xaa is leucine, glycine, or alanine
<220> FEATURE:
<221> NAME/KEY: VARIANT
<222> LOCATION: (15)..(15)
<223> OTHER INFORMATION: Xaa is leucine, glycine, or alanine
<220> FEATURE:
<221> NAME/KEY: VARIANT
<222> LOCATION: (18)..(18)
<223> OTHER INFORMATION: Xaa is phenylalanine, glycine, or alanine
<220> FEATURE:
<221> NAME/KEY: VARIANT
<222> LOCATION: (19)..(19)
<223> OTHER INFORMATION: Xaa is leucine, glycine, or alanine

<400> SEQUENCE: 42

Xaa Glu Xaa Xaa Ala Lys Xaa Xaa Lys Xaa Xaa Lys Asp Xaa Xaa Gly
 1               5                  10                  15

Lys Xaa Xaa Gly Asn Asn
            20

<210> SEQ ID NO 43
<211> LENGTH: 20
<212> TYPE: PRT
<213> ORGANISM: Artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: Xaa is  methionine, glycine, or alanine
<220> FEATURE:
<221> NAME/KEY: misc_feature
<222> LOCATION: (3)..(3)
<223> OTHER INFORMATION: Xaa is  isoleucine, glycine, or alanine
<220> FEATURE:
<221> NAME/KEY: misc_feature
<222> LOCATION: (4)..(4)
<223> OTHER INFORMATION: Xaa is  valine, glycine, or alanine
<220> FEATURE:
<221> NAME/KEY: misc_feature
<222> LOCATION: (7)..(7)
<223> OTHER INFORMATION: Xaa is  isoleucine, glycine, or alanine
<220> FEATURE:
<221> NAME/KEY: misc_feature
<222> LOCATION: (8)..(8)
<223> OTHER INFORMATION: Xaa is  isoleucine, glycine, or alanine
<220> FEATURE:
<221> NAME/KEY: misc_feature
<222> LOCATION: (10)..(10)
<223> OTHER INFORMATION: Xaa is  isoleucine, glycine, or alanine
<220> FEATURE:
<221> NAME/KEY: misc_feature
<222> LOCATION: (11)..(11)
<223> OTHER INFORMATION: Xaa is  isoleucine, glycine, or alanine
```

```
<220> FEATURE:
<221> NAME/KEY: misc_feature
<222> LOCATION: (14)..(14)
<223> OTHER INFORMATION: Xaa is  isoleucine, glycine, or alanine
<220> FEATURE:
<221> NAME/KEY: misc_feature
<222> LOCATION: (15)..(15)
<223> OTHER INFORMATION: Xaa is  isoleucine, glycine, or alanine
<220> FEATURE:
<221> NAME/KEY: misc_feature
<222> LOCATION: (17)..(17)
<223> OTHER INFORMATION: Xaa is  isoleucine, glycine, or alanine
<220> FEATURE:
<221> NAME/KEY: misc_feature
<222> LOCATION: (18)..(18)
<223> OTHER INFORMATION: Xaa is  phenylalanine, glycine, or alanine

<400> SEQUENCE: 43

Xaa Ala Xaa Xaa Gly Thr Xaa Xaa Lys Xaa Xaa Lys Ala Xaa Xaa Asp
1               5                  10                  15

Xaa Xaa Ala Lys
            20

<210> SEQ ID NO 44
<211> LENGTH: 44
<212> TYPE: PRT
<213> ORGANISM: Artificial
<220> FEATURE:
<223> OTHER INFORMATION: synthetic
<220> FEATURE:
<221> NAME/KEY: Variant
<222> LOCATION: (4)..(4)
<223> OTHER INFORMATION: Xaa is leucine, glycine, or alanine
<220> FEATURE:
<221> NAME/KEY: Variant
<222> LOCATION: (5)..(5)
<223> OTHER INFORMATION: Xaa is phenylalanine, glycine, or alanine
<220> FEATURE:
<221> NAME/KEY: Variant
<222> LOCATION: (8)..(8)
<223> OTHER INFORMATION: Xaa is isoleucine, glycine, or alanine
<220> FEATURE:
<221> NAME/KEY: Variant
<222> LOCATION: (12)..(12)
<223> OTHER INFORMATION: Xaa is valine, glycine, or alanine
<220> FEATURE:
<221> NAME/KEY: Variant
<222> LOCATION: (16)..(16)
<223> OTHER INFORMATION: Xaa is isoleucine, glycine, or alanine

<400> SEQUENCE: 44

Met Glu Gly Xaa Xaa Asn Ala Xaa Lys Asp Thr Xaa Thr Ala Ala Xaa
1               5                  10                  15

Asn Asn Asp Gly Ala Lys Leu Gly Thr Ser Ile Val Asn Ile Val Glu
            20                  25                  30

Asn Gly Val Gly Leu Leu Ser Lys Leu Phe Gly Phe
            35                  40

<210> SEQ ID NO 45
<211> LENGTH: 44
<212> TYPE: PRT
<213> ORGANISM: Artificial
<220> FEATURE:
<223> OTHER INFORMATION: synthetic
<220> FEATURE:
<221> NAME/KEY: Variant
<222> LOCATION: (4)..(4)
<223> OTHER INFORMATION: Xaa is leucine, glycine, or alanine
<220> FEATURE:
<221> NAME/KEY: Variant
<222> LOCATION: (8)..(8)
<223> OTHER INFORMATION: Xaa is isoleucine, glycine, or alanine
```

```
<220> FEATURE:
<221> NAME/KEY: Variant
<222> LOCATION: (12)..(12)
<223> OTHER INFORMATION: Xaa is valine, glycine, or alanine
<220> FEATURE:
<221> NAME/KEY: Variant
<222> LOCATION: (23)..(23)
<223> OTHER INFORMATION: Xaa is leucine, glycine, or alanine

<400> SEQUENCE: 45

Met Thr Gly Xaa Ala Glu Ala Xaa Ala Asn Thr Xaa Gln Ala Ala Gln
1               5                   10                  15

Gln His Asp Ser Val Lys Xaa Gly Thr Ser Ile Val Asp Ile Val Ala
            20                  25                  30

Asn Gly Val Gly Leu Leu Gly Lys Leu Phe Gly Phe
        35                  40

<210> SEQ ID NO 46
<211> LENGTH: 62
<212> TYPE: PRT
<213> ORGANISM: Artificial
<220> FEATURE:
<223> OTHER INFORMATION: synthetic

<400> SEQUENCE: 46

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala
    50                  55                  60

<210> SEQ ID NO 47
<211> LENGTH: 284
<212> TYPE: PRT
<213> ORGANISM: Staphylococcus aureus

<400> SEQUENCE: 47

Asp Asn Asn Ile Glu Asn Ile Gly Asp Gly Ala Glu Val Val Lys Arg
1               5                   10                  15

Thr Glu Asp Thr Ser Ser Asp Lys Trp Gly Val Thr Gln Asn Ile Gln
            20                  25                  30

Phe Asp Phe Val Lys Asp Lys Lys Tyr Asn Lys Asp Ala Leu Ile Leu
        35                  40                  45

Lys Met Gln Gly Phe Ile Asn Ser Lys Thr Thr Tyr Tyr Asn Tyr Lys
    50                  55                  60

Asn Thr Asp His Ile Lys Ala Met Arg Trp Pro Phe Gln Tyr Asn Ile
65                  70                  75                  80

Gly Leu Lys Thr Asn Asp Pro Asn Val Asp Leu Ile Asn Tyr Leu Pro
                85                  90                  95

Lys Asn Lys Ile Asp Ser Val Asn Val Ser Gln Thr Leu Gly Tyr Asn
            100                 105                 110

Ile Gly Gly Asn Phe Asn Ser Gly Pro Ser Thr Gly Gly Asn Gly Ser
        115                 120                 125

Phe Asn Tyr Ser Lys Thr Ile Ser Tyr Asn Gln Gln Asn Tyr Ile Ser
    130                 135                 140

Glu Val Glu His Gln Asn Ser Lys Ser Val Gln Trp Gly Ile Lys Ala
145                 150                 155                 160
```

Asn Ser Phe Ile Thr Ser Leu Gly Lys Met Ser Gly His Asp Pro Asn
            165                 170                 175

Leu Phe Val Gly Tyr Lys Pro Tyr Ser Gln Asn Pro Arg Asp Tyr Phe
            180                 185                 190

Val Pro Asp Asn Glu Leu Pro Pro Leu Val His Ser Gly Phe Asn Pro
            195                 200                 205

Ser Phe Ile Ala Thr Val Ser His Glu Lys Gly Ser Gly Asp Thr Ser
210                 215                 220

Glu Phe Glu Ile Thr Tyr Gly Arg Asn Met Asp Val Thr His Ala Thr
225                 230                 235                 240

Arg Arg Thr Thr His Tyr Gly Asn Ser Tyr Leu Glu Gly Ser Arg Ile
            245                 250                 255

His Asn Ala Phe Val Asn Arg Asn Tyr Thr Val Lys Tyr Glu Val Asn
            260                 265                 270

Trp Lys Thr His Glu Ile Lys Val Lys Gly His Asn
            275                 280

<210> SEQ ID NO 48
<211> LENGTH: 301
<212> TYPE: PRT
<213> ORGANISM: Staphylococcus aureus

<400> SEQUENCE: 48

Ala Gln His Ile Thr Pro Val Ser Glu Lys Lys Val Asp Asp Lys Ile
1               5                   10                  15

Thr Leu Tyr Lys Thr Thr Ala Thr Ser Asp Ser Asp Lys Leu Lys Ile
            20                  25                  30

Ser Gln Ile Leu Thr Phe Asn Phe Ile Lys Asp Lys Ser Tyr Asp Lys
            35                  40                  45

Asp Thr Leu Ile Leu Lys Ala Ala Gly Asn Ile Tyr Ser Gly Tyr Thr
50                  55                  60

Lys Pro Asn Pro Lys Asp Thr Ile Ser Ser Gln Phe Tyr Trp Gly Ser
65                  70                  75                  80

Lys Tyr Asn Ile Ser Ile Asn Ser Asp Ser Asn Asp Ser Val Asn Val
            85                  90                  95

Val Asp Tyr Ala Pro Lys Asn Gln Asn Glu Glu Phe Gln Val Gln Gln
            100                 105                 110

Thr Val Gly Tyr Ser Tyr Gly Gly Asp Ile Asn Ile Ser Asn Gly Leu
            115                 120                 125

Ser Gly Gly Gly Asn Gly Ser Lys Ser Phe Ser Glu Thr Ile Asn Tyr
            130                 135                 140

Lys Gln Glu Ser Tyr Arg Thr Ser Leu Asp Lys Arg Thr Asn Phe Lys
145                 150                 155                 160

Lys Ile Gly Trp Asp Val Glu Ala His Lys Ile Met Asn Asn Gly Trp
            165                 170                 175

Gly Pro Tyr Gly Arg Asp Ser Tyr His Ser Thr Tyr Gly Asn Glu Met
            180                 185                 190

Phe Leu Gly Ser Arg Gln Ser Asn Leu Asn Ala Gly Gln Asn Phe Leu
            195                 200                 205

Glu Tyr His Lys Met Pro Val Leu Ser Arg Gly Asn Phe Asn Pro Glu
            210                 215                 220

Phe Ile Gly Val Leu Ser Arg Lys Gln Asn Ala Ala Lys Lys Ser Lys
225                 230                 235                 240

Ile Thr Val Thr Tyr Gln Arg Glu Met Asp Arg Tyr Thr Asn Phe Trp

```
                       245                 250                 255
Asn Gln Leu His Trp Ile Gly Asn Asn Tyr Lys Asp Glu Asn Arg Ala
            260                 265                 270

Thr His Thr Ser Ile Tyr Glu Val Asp Trp Glu Asn His Thr Val Lys
            275                 280                 285

Leu Ile Asp Thr Gln Ser Lys Glu Lys Asn Pro Met Ser
            290                 295                 300

<210> SEQ ID NO 49
<211> LENGTH: 240
<212> TYPE: PRT
<213> ORGANISM: Artificial
<220> FEATURE:
<223> OTHER INFORMATION: synthetic

<400> SEQUENCE: 49

Met Glu Ser Gln Pro Asp Pro Lys Pro Asp Glu Leu His Lys Ser Ser
1               5                   10                  15

Lys Phe Thr Gly Leu Met Glu Asn Met Lys Val Leu Tyr Asp Asp Asn
            20                  25                  30

His Val Ser Ala Ile Asn Val Lys Ser Ile Asp Gln Phe Arg Tyr Phe
        35                  40                  45

Asp Leu Ile Tyr Ser Ile Lys Asp Thr Lys Leu Gly Asn Tyr Asp Asn
    50                  55                  60

Val Arg Val Glu Phe Lys Asn Lys Asp Leu Ala Asp Lys Tyr Lys Asp
65                  70                  75                  80

Lys Tyr Val Asp Val Phe Gly Ala Asn Ala Tyr Tyr Gln Cys Ala Phe
                85                  90                  95

Ser Lys Lys Thr Asn Asp Ile Asn Ser His Gln Thr Asp Lys Arg Lys
            100                 105                 110

Thr Cys Met Tyr Gly Gly Val Thr Glu His Asn Gly Asn Gln Leu Asp
        115                 120                 125

Lys Tyr Arg Ser Ile Thr Val Arg Val Phe Glu Asp Gly Lys Asn Leu
    130                 135                 140

Leu Ser Phe Asp Val Gln Thr Asn Lys Lys Lys Val Thr Ala Gln Glu
145                 150                 155                 160

Leu Asp Tyr Leu Thr Arg His Tyr Leu Val Lys Asn Lys Lys Leu Tyr
                165                 170                 175

Glu Phe Asn Asn Ser Pro Tyr Glu Thr Gly Tyr Ile Lys Phe Ile Glu
            180                 185                 190

Asn Glu Asn Ser Phe Trp Tyr Asp Met Met Pro Ala Pro Gly Asp Lys
        195                 200                 205

Phe Asp Gln Ser Lys Tyr Leu Met Met Tyr Asn Asp Asn Lys Met Val
    210                 215                 220

Asp Ser Lys Asp Val Lys Ile Glu Val Tyr Leu Thr Thr Lys Lys Lys
225                 230                 235                 240

<210> SEQ ID NO 50
<211> LENGTH: 232
<212> TYPE: PRT
<213> ORGANISM: Artificial
<220> FEATURE:
<223> OTHER INFORMATION: synthetic

<400> SEQUENCE: 50

Glu Lys Ser Glu Glu Ile Asn Glu Lys Asp Leu Arg Lys Lys Ser Glu
1               5                   10                  15
```

```
Leu Gln Gly Thr Ala Leu Gly Asn Leu Lys Gln Ile Tyr Tyr Asn
             20                  25                  30

Glu Lys Ala Lys Thr Glu Asn Lys Glu Ser His Asp Gln Phe Arg Gln
         35                  40                  45

His Thr Ile Leu Phe Lys Gly Phe Phe Thr Asp His Ser Trp Tyr Asn
 50                  55                  60

Asp Leu Leu Val Arg Phe Asp Ser Lys Asp Ile Val Asp Lys Tyr Lys
65                  70                  75                  80

Gly Lys Lys Val Asp Leu Tyr Gly Ala Tyr Ala Gly Tyr Gln Cys Ala
                 85                  90                  95

Gly Gly Thr Pro Asn Lys Thr Ala Cys Met Tyr Gly Val Thr Leu
                100                 105                 110

His Asp Asn Asn Arg Leu Thr Glu Glu Lys Lys Val Pro Ile Asn Leu
             115                 120                 125

Trp Leu Asp Gly Lys Gln Asn Thr Val Pro Leu Glu Thr Val Lys Thr
        130                 135                 140

Asn Lys Lys Asn Val Thr Val Gln Glu Leu Asp Leu Gln Ala Arg Arg
145                 150                 155                 160

Tyr Leu Gln Glu Lys Tyr Asn Leu Tyr Asn Ser Asp Val Phe Asp Gly
                165                 170                 175

Lys Val Gln Arg Gly Leu Ile Val Phe His Thr Ser Thr Glu Pro Ser
            180                 185                 190

Val Asn Tyr Asp Leu Phe Gly Ala Gln Gly Gln Tyr Ser Asn Thr Leu
        195                 200                 205

Leu Arg Ile Tyr Arg Asp Asn Lys Thr Ile Asn Ser Glu Asn Met His
210                 215                 220

Ile Asp Ile Tyr Leu Tyr Thr Ser
225                 230

<210> SEQ ID NO 51
<211> LENGTH: 195
<212> TYPE: PRT
<213> ORGANISM: Artificial
<220> FEATURE:
<223> OTHER INFORMATION: synthetic

<400> SEQUENCE: 51

Met Ser Thr Asn Asp Asn Ile Lys Asp Leu Leu Asp Trp Tyr Ser Ser
1                   5                  10                  15

Gly Ser Asp Thr Phe Thr Asn Ser Glu Val Leu Ala Asn Ser Arg Gly
             20                  25                  30

Ser Met Arg Ile Lys Asn Thr Asp Gly Ser Ile Ser Leu Ile Ala Phe
         35                  40                  45

Pro Ser Pro Tyr Tyr Ser Pro Ala Phe Thr Lys Gly Glu Lys Val Asp
     50                  55                  60

Leu Asn Thr Lys Arg Thr Lys Lys Ser Gln His Thr Ser Glu Gly Thr
65                  70                  75                  80

Tyr Ile His Phe Gln Ile Ser Gly Val Thr Asn Thr Glu Lys Leu Pro
                 85                  90                  95

Thr Pro Ile Glu Leu Pro Leu Lys Val Lys Val His Gly Lys Asp Ser
                100                 105                 110

Pro Leu Lys Tyr Trp Pro Lys Phe Asp Lys Lys Gln Leu Ala Ile Ser
            115                 120                 125

Thr Leu Asp Phe Glu Ile Arg His Gln Leu Thr Gln Ile His Gly Leu
        130                 135                 140
```

```
Tyr Arg Ser Ser Asp Lys Thr Gly Gly Tyr Trp Lys Ile Thr Met Asn
145                 150                 155                 160

Asp Gly Ser Thr Tyr Gln Ser Asp Leu Ser Lys Phe Glu Tyr Asn
            165                 170                 175

Thr Glu Lys Pro Pro Ile Asn Ile Asp Glu Ile Lys Thr Ile Glu Ala
            180                 185                 190

Glu Ile Asn
        195

<210> SEQ ID NO 52
<211> LENGTH: 22
<212> TYPE: PRT
<213> ORGANISM: Staphylococcus aureus

<400> SEQUENCE: 52

Met Asp Phe Thr Gly Val Ile Thr Ser Ile Ile Asp Leu Ile Lys Thr
1               5                   10                  15

Cys Ile Gln Ala Phe Gly
            20

<210> SEQ ID NO 53
<211> LENGTH: 22
<212> TYPE: PRT
<213> ORGANISM: Artificial
<220> FEATURE:
<223> OTHER INFORMATION: synthetic
<220> FEATURE:
<221> NAME/KEY: Variant
<222> LOCATION: (3)..(3)
<223> OTHER INFORMATION: Xaa is phenylalanine, glycine, or alanine
<220> FEATURE:
<221> NAME/KEY: Variant
<222> LOCATION: (6)..(6)
<223> OTHER INFORMATION: Xaa is valine, glycine, or alanine
<220> FEATURE:
<221> NAME/KEY: Variant
<222> LOCATION: (7)..(7)
<223> OTHER INFORMATION: Xaa is isoleucine, glycine, or alanine
<220> FEATURE:
<221> NAME/KEY: Variant
<222> LOCATION: (10)..(10)
<223> OTHER INFORMATION: Xaa is isoleucine, glycine, or alanine
<220> FEATURE:
<221> NAME/KEY: Variant
<222> LOCATION: (11)..(11)
<223> OTHER INFORMATION: Xaa is isoleucine, glycine, or alanine
<220> FEATURE:
<221> NAME/KEY: Variant
<222> LOCATION: (13)..(13)
<223> OTHER INFORMATION: Xaa is leucine, glycine, or alanine
<220> FEATURE:
<221> NAME/KEY: Variant
<222> LOCATION: (14)..(14)
<223> OTHER INFORMATION: Xaa is isoleucine, glycine, or alanine
<220> FEATURE:
<221> NAME/KEY: Variant
<222> LOCATION: (17)..(17)
<223> OTHER INFORMATION: Xaa is cysteine, glycine, or alanine
<220> FEATURE:
<221> NAME/KEY: Variant
<222> LOCATION: (18)..(18)
<223> OTHER INFORMATION: Xaa is isoleucine, glycine, or alanine

<400> SEQUENCE: 53

Met Asp Xaa Thr Gly Xaa Xaa Thr Ser Xaa Xaa Asp Xaa Xaa Lys Thr
1               5                   10                  15

Xaa Xaa Gln Ala Phe Gly
            20
```

```
<210> SEQ ID NO 54
<211> LENGTH: 284
<212> TYPE: PRT
<213> ORGANISM: Artificial
<220> FEATURE:
<223> OTHER INFORMATION: synthetic

<400> SEQUENCE: 54

Asp Asn Asn Ile Glu Asn Ile Gly Asp Gly Ala Glu Val Val Lys Arg
1               5                   10                  15

Thr Glu Asp Thr Ser Ser Asp Lys Trp Gly Val Phe Gln Asn Ile Gln
            20                  25                  30

Phe Asp Phe Val Lys Asp Lys Lys Tyr Asn Lys Asp Ala Leu Ile Leu
        35                  40                  45

Lys Met Gln Gly Phe Ile Asn Ser Lys Thr Thr Tyr Tyr Asn Tyr Lys
50                  55                  60

Asn Thr Asp His Ile Lys Ala Met Arg Trp Pro Phe Gln Tyr Asn Ile
65                  70                  75                  80

Gly Leu Lys Thr Asn Asp Pro Asn Val Asp Leu Ile Asn Tyr Leu Pro
                85                  90                  95

Ala Asn Lys Ile Asp Ser Val Asn Val Ser Gln Thr Leu Gly Tyr Asn
            100                 105                 110

Ile Gly Gly Asn Phe Asn Ser Gly Pro Ser Thr Gly Asn Gly Ser
        115                 120                 125

Phe Asn Tyr Ser Lys Thr Ile Ser Tyr Asn Gln Gln Asn Tyr Ile Ser
130                 135                 140

Glu Val Glu His Gln Asn Ser Lys Ser Val Gln Trp Gly Ile Lys Ala
145                 150                 155                 160

Asn Ser Phe Ile Thr Ser Leu Gly Lys Met Ser Gly His Asp Pro Asn
                165                 170                 175

Leu Phe Val Gly Tyr Lys Pro Tyr Ser Gln Asn Pro Arg Asp Tyr Phe
            180                 185                 190

Val Pro Asp Asn Glu Leu Pro Pro Leu Val His Ser Gly Phe Asn Pro
        195                 200                 205

Ala Phe Ile Ala Thr Val Ser His Glu Lys Gly Ser Gly Asp Thr Ser
210                 215                 220

Glu Phe Glu Ile Thr Tyr Gly Arg Asn Met Asp Val Thr His Ala Thr
225                 230                 235                 240

Arg Arg Thr Thr His Tyr Gly Asn Ser Tyr Leu Glu Gly Ser Arg Ile
                245                 250                 255

His Asn Ala Phe Val Asn Arg Asn Tyr Thr Val Lys Tyr Glu Val Asn
            260                 265                 270

Trp Lys Thr His Glu Ile Lys Val Lys Gly His Asn
        275                 280

<210> SEQ ID NO 55
<211> LENGTH: 301
<212> TYPE: PRT
<213> ORGANISM: Artificial
<220> FEATURE:
<223> OTHER INFORMATION: synthetic

<400> SEQUENCE: 55

Ala Gln His Ile Thr Pro Val Ser Glu Lys Lys Val Asp Asp Lys Ile
1               5                   10                  15

Thr Leu Tyr Lys Thr Thr Ala Thr Ser Asp Ser Asp Lys Leu Lys Ile
            20                  25                  30
```

-continued

```
Ser Gln Ile Leu Thr Phe Asn Phe Ile Lys Asp Lys Ser Tyr Asp Lys
            35                  40                  45

Asp Thr Leu Ile Leu Lys Ala Ala Gly Asn Ile Tyr Ser Gly Tyr Thr
 50                  55                  60

Lys Pro Asn Pro Lys Asp Thr Ile Ser Ser Gln Phe Tyr Trp Gly Ser
 65                  70                  75                  80

Lys Tyr Asn Ile Ser Ile Asn Ser Asp Ser Asn Asp Ser Val Asn Val
                85                  90                  95

Val Asp Tyr Ala Pro Ala Asn Gln Asn Glu Glu Phe Gln Val Gln Gln
            100                 105                 110

Thr Val Gly Tyr Ser Tyr Gly Gly Asp Ile Asn Ile Ser Asn Gly Leu
        115                 120                 125

Ser Gly Gly Gly Asn Gly Ser Lys Ser Phe Ser Glu Thr Ile Asn Tyr
130                 135                 140

Lys Gln Glu Ser Tyr Arg Thr Ser Leu Asp Lys Arg Thr Asn Phe Lys
145                 150                 155                 160

Lys Ile Gly Trp Asp Val Glu Ala His Lys Ile Met Asn Asn Gly Trp
                165                 170                 175

Gly Pro Tyr Gly Arg Asp Ser Tyr His Ser Thr Tyr Gly Asn Glu Met
            180                 185                 190

Phe Leu Gly Ser Arg Gln Ser Asn Leu Asn Ala Gly Gln Asn Phe Leu
        195                 200                 205

Glu Tyr His Lys Met Pro Val Leu Ser Arg Gly Asn Phe Asn Pro Glu
210                 215                 220

Phe Ile Gly Val Leu Ser Arg Lys Gln Asn Ala Ala Lys Lys Ser Lys
225                 230                 235                 240

Ile Thr Val Thr Tyr Gln Arg Glu Met Asp Arg Tyr Thr Asn Phe Trp
                245                 250                 255

Asn Gln Leu His Trp Ile Gly Asn Asn Tyr Lys Asp Glu Asn Arg Ala
            260                 265                 270

Thr His Thr Ser Ile Tyr Glu Val Asp Trp Glu Asn His Thr Val Lys
        275                 280                 285

Leu Ile Asp Thr Gln Ser Lys Glu Lys Asn Pro Met Ser
290                 295                 300
```

<210> SEQ ID NO 56
<211> LENGTH: 4
<212> TYPE: PRT
<213> ORGANISM: Artificial Sequence
<220> FEATURE:
<223> OTHER INFORMATION: Synthetic linker

<400> SEQUENCE: 56

```
Gly Gly Gly Ser
1
```

<210> SEQ ID NO 57
<211> LENGTH: 5
<212> TYPE: PRT
<213> ORGANISM: Artificial Sequence
<220> FEATURE:
<223> OTHER INFORMATION: Synthetic linker

<400> SEQUENCE: 57

```
Gly Gly Gly Gly Ser
1               5
```

<210> SEQ ID NO 58

```
<211> LENGTH: 10
<212> TYPE: PRT
<213> ORGANISM: Staphylococcus aureus

<400> SEQUENCE: 58

Val Ile Leu Ile Phe Ile Ile Ile Ile Met
1               5                   10

<210> SEQ ID NO 59
<211> LENGTH: 10
<212> TYPE: PRT
<213> ORGANISM: Staphylococcus aureus

<400> SEQUENCE: 59

Phe Ile Leu Ile Phe Ile Ile Ile Ile Met
1               5                   10

<210> SEQ ID NO 60
<211> LENGTH: 10
<212> TYPE: PRT
<213> ORGANISM: Staphylococcus aureus

<400> SEQUENCE: 60

Phe Phe Leu Leu Phe Phe Val Leu Phe Met
1               5                   10

<210> SEQ ID NO 61
<211> LENGTH: 11
<212> TYPE: PRT
<213> ORGANISM: Staphylococcus aureus

<400> SEQUENCE: 61

Ile Ile Ile Ile Ile Phe Ile Val Ile Ile Met
1               5                   10

<210> SEQ ID NO 62
<211> LENGTH: 6
<212> TYPE: PRT
<213> ORGANISM: Staphylococcus aureus

<400> SEQUENCE: 62

Leu Ala Ile Met Val Phe
1               5

<210> SEQ ID NO 63
<211> LENGTH: 6
<212> TYPE: PRT
<213> ORGANISM: Staphylococcus aureus

<400> SEQUENCE: 63

Leu Ala Ile Met Val Ala
1               5

<210> SEQ ID NO 64
<211> LENGTH: 7
<212> TYPE: PRT
<213> ORGANISM: Staphylococcus aureus

<400> SEQUENCE: 64

Ile Ile Ile Val Val Ile Ile
1               5

<210> SEQ ID NO 65
<211> LENGTH: 22
<212> TYPE: PRT
```

-continued

```
<213> ORGANISM: Staphylococcus aureus

<400> SEQUENCE: 65

Met Asp Phe Thr Gly Val Ile Thr Ser Ile Ile Asp Leu Ile Lys Thr
1               5                   10                  15

Cys Ile Gln Ala Phe Gly
            20

<210> SEQ ID NO 66
<211> LENGTH: 9
<212> TYPE: PRT
<213> ORGANISM: Staphylococcus aureus

<400> SEQUENCE: 66

Leu Val Cys Ile Phe Ile Ile Ile Ile
1               5
```

TOXOID PEPTIDES DERIVED FROM PHENOL SOLUBLE MODULIN, DELTA TOXIN, SUPERANTIGENS, AND FUSIONS THEREOF

CROSS-REFERENCE TO RELATED APPLICATIONS

This application is a 35 U.S.C. §371 US National Stage Application of International Patent Application PCT/US2014/042999, filed Jun. 18, 2014, which claims the benefit of U.S. Provisional Patent Application Ser. NO. 61/836,959, filed Jun. 19, 2013, the disclosures of both of which are incorporated herein by reference in their entireties.

INCORPORATION OF SEQUENCE LISTING

The sequence listing that is contained in the file named "57783_151830_SEQ_LST_ST25.txt", which is 88,443 bytes (measured in operating system MS-Windows), created on Jun. 19, 2013, is filed herewith by electronic submission and incorporated herein by reference in its entirety.

REFERENCE TO SEQUENCE LISTING SUBMITTED ELECTRONICALLY

The content of the electronically submitted sequence listing in ASCII text file (Name: 57783_132959_SEQ_LST_ST25.txt; Size: 88,443 bytes; and Date of Creation: Jun. 18, 2014) filed with the application is incorporated herein by reference in its entirety.

BACKGROUND

*Staphylococcus aureus* (SA) is a Gram-positive human pathogen that causes a wide range of infections from skin and soft tissue infections (SSTI) to life threatening sepsis and pneumonia. It is a leading cause of hospital- and community-associated infections worldwide (Barrio, et al., 2006, *Microbes Infect*, 8 (8):2068-2074; Brown, et al., 2009 *Clin Microbiol Infect*, 15 (2):156-164; Colin, et al. 1994, *Infect Immun*, 62 (8):3184-3188). The range of pathologies reflects the diverse abilities of SA to escape the immune response using a plethora of virulence factors: the superantigenic and pore-forming toxins, coagulase, capsular polysaccharide, adhesins, proteases, complement inactivating exoproteins, and other innate response modifiers (Barrio, et al., 2006, *Microbes Infect*, 8 (8):2068-2074; Deurenberg and Stobberingh, 2008, *Infect Genet Evol*, 8 (6):747-763).

Since its first emergence in the 1960s methicillin-resistant SA (MRSA) has become endemic in healthcare settings worldwide (Diep, et al., 2006, *J Infect Dis*, 193 (11):1495-1503). Since the 1990s, community associated MRSA strains (CA-MRSA) emerged, and are posing a major global challenge (Bassetti, et al., 2009, *Int J Antimicrob Agents*, 34 Suppl 1:S15-19; Bradley, 2005, *Semin Respir Crit Care Med*, 26 (6):643-649; Chambers, 2005, *N. Engl J Med*, 352 (14):1485-1487). Alpha hemolysin (α-toxin, Hla) is a major virulence factor in SA pneumonia and SSTI (Bubeck Wardenburg and Schneewind, 2008, *J Exp Med*, 205 (2):287-294; Kennedy, et al., 2010, *J Infect Dis*, 202 (7):1050-1058). Recently, cytolytic short peptides known as phenol soluble modulins (PSMs) were identified as key virulence factors that lyse neutrophils, the main line of defense against *S. aureus* (Wang, et al., 2007, *Nat Med*, 13 (12):1510-1514). Another related cytolytic short peptide of staphylococci is known as delta hemolysin or delta toxin (δtoxin) the key marker of *S. aureus* quorum sensing system (agr) (Novick, et al., 1993, *EMBO J*, 12 (10):3967-3975). A recent epidemiological study in a cohort of patients with SA bacteremia shows inverse correlation between probability of sepsis and pre-existing antibodies to Hla, PSM-α3, as well as δ-toxin (Adhikari, et al., 2012, *J Infect Dis*, 206 (6):915-923).

Staphylococcal superantigens (SAgs) induce a massive release of cytokines and chemokines, enhanced expression and activation of adhesion molecules, increased T-cell proliferation, and ultimately T-cell apoptosis/anergy. This sequence of events can culminate in Toxic Shock Syndrome (TSS), a life threatening condition (Todd, et al., 1978, *Lancet*, 2 (8100):1116-1118) characterized by rash, hypotension, fever, and multisystem dysfunction (Bohach, et al., 1990, *Crit Rev Microbiol*, 17 (4):251-272). A major challenge in development of multivalent *S. aureus* vaccines including superantigens is that there are more than 20 different SAgs and there is a wide range of variability in SAg presence in clinical isolates because most SEs are on mobile genetic elements, such as plasmids or pathogenicity islands (Staphylococcal enterotoxin K(sek), (Staphylococcal enterotoxin Q seq), lysogenic phages (Staphylococcal enterotoxin A (sea), or antibiotic resistance cassettes, like SCCmec (Staphylococcal enterotoxin H (seh) (Omoe, et al., 2002, *J Clin Microbiol*, 40 (3):857-862). Based on an extensive literature review encompassing over 6000 clinical isolates, the most widely represented Superantigens (Sags) appear to be toxic shock syndrome toxin 1 (TSST-1) and (Staphylococcal enterotoxin C (SEC), followed by (Staphylococcal enterotoxin A (SEA), (Staphylococcal enterotoxin D (SED), and (Staphylococcal enterotoxin B (SEB). More recent studies show the emergence of (Staphylococcal enterotoxin K (SEK) and (Staphylococcal enterotoxinQ (SEQ), primarily due to circulation of the USA300 clone. Attenuated Superantigen toxoids for (Staphylococcal enterotoxin (SEA), (Staphylococcal enterotoxin B (SEB), and TSST-1 have been designed and tested in animal models of toxic shock. These mutants are deficient in binding to MHC class II protein and therefore lack superantigenic activity (subject of U.S. Pat. Nos. 6,713,284; 6,399,332; 7,087,235; 7,750,132; 7,378,257, and 8,067,202). A simplified superantigen toxoid vaccine capable of inducing broad neutralizing antibodies is therefore highly is needed to be practical for inclusion into a multivalent *S. aureus* vaccine.

Phenol Soluble modulins (PSMs) and Delta-Hemolysin (δ-toxin): *S. aureus* secretes four short (~20 amino acids, α-type) and two longer (~40 amino acids, β-type) cytolytic peptides, known as phenol soluble modulin (PSM) (Wang, et al., 2007, *Nat Med*, 13 (12):1510-1514). In addition, SA produces δ-toxin, which is similar to the α-type PSMs. These genes are expressed in all *S. aureus* strains under the control of the agr system (Wang, et al., 2007, *Nat Med*, 13 (12):1510-1514). Recently, a novel PSM (PSM-mec) has been also identified within the staphylococcal methicillin resistance mobile genetic element SCCmec (Chatterjee, et al., 2011, *PLoS One*, 6 (12):e28781; Kaito, et al., 2011, *PLoS Pathog*, 7 (2):e1001267) suggesting that horizontal transfer of these toxins can contribute to MRSA virulence. PSMs are lytic towards neutrophils, the first line of host defense against SA (Wang, et al., 2007, *Nat Med*, 13 (12):1510-1514). Furthermore, recent studies indicate a synergistic effect on hemolytic activity of β-hemolysin (Cheung, et al., 2012, *Microbes Infect*, 14 (4):380-386). A key role of PSMs in pathogenesis has been shown in mouse models of bacteremia and SSTI using deletion mutants (Wang, et al., 2007, *Nat Med*, 13 (12):1510-1514). Furthermore, a recent report suggests a key role for PSMs in biofilm formation (Periasamy, et al., 2012, *Proc Natl Acad Sci USA*, 109 (4):1281-1286). Among the PSMs, PSM-α3 plays the most prominent role in *S. aureus* pathogenesis (Wang, et al., 2007, *Nat Med*, 13 (12):1510-1514).

δ-Toxin is encoded by the hld gene located within RNAIII transcript of agr locus. RNAIII is a regulatory RNA and plays a major role in regulation of SA quorum-sensing system for the expression of various virulence genes (Novick, 2003, *Mol Microbiol*, 48 (6):1429-1449; Novick, et al., 1993, *EMBO J*, 12 (10):3967-3975). With increased expression of RNAIII, the level of extracellular δ-toxin is increased reaching almost half the amount of total exoproteins at the stationary phase (Kreger, et al., 1971, *Infect Immun*, 3 (3):449-465). The hld$^{-/-}$ mutant of the CA-MRSA strain MW2 exhibited attenuated virulence in mouse bacteremia model (Wang, et al., 2007, *Nat Med*, 13 (12):1510-1514). A recent study also revealed that δ-toxin increases the cell number/unit area of colony by inhibiting colony spreading, resulting in a thicker giant colony and promotes the compartmentalization of SA colonies leading to efficient colonization (Omae, et al., 2012, *J Biol Chem*, 287 (19): 15570-15579). Thus δ-toxin also appears to modulate the physical state of SA colonies. δ-toxin also plays an important role in the escape of *S. aureus* from phago-endosomes of human epithelial and endothelial cells in the presence of beta-toxin (Giese, et al., 2011, *Cell Microbiol*, 13 (2):316-329) by acting as a costimulator of human neutrophil oxidative burst (Schmitz, et al., 1997, *J Infect Dis*, 176 (6):1531-1537).

*S. aureus* alpha hemolysin (Hla): The pore forming toxins form oligomeric beta barrel pores in the plasma membrane and play an important role for bacterial spread and survival, immune evasion and tissue destruction. SA alpha-toxin (Hla) (Bhakdi and Tranum-Jensen, 1991, *Microbiol Rev*, 55 (4):733-751) targets many cells such as lymphocytes, macrophages, pulmonary epithelial cells and endothelium, and erythrocytes (Bhakdi and Tranum-Jensen, 1991, *Microbiol Rev*, 55 (4):733-751; McElroy, et al., 1999, *Infect Immun*, 67 (10):5541-5544). Several lines of evidence validate Hla as a prime vaccine target for prevention of *S. aureus* infection or complications: i) hla is encoded by a chromosomal determinant (Brown and Pattee, 1980, *Infect Immun*, 30 (1):36-42), and expressed in most SA isolates (Aarestrup, et al., 1999, *APMIS*, 107 (4):425-430; Bhakdi and Tranum-Jensen, 1991, *Microbiol Rev*, 55 (4):733-751; Husmann, et al., 2009, *FEBS Lett*, 583 (2):337-344; Shukla, et al., 2010, *J Clin Microbiol*, 48 (10):3582-3592); ii) A partially attenuated Hla (H35L) and antibodies to Hla protect mice against SA pneumonia and skin infections (Kennedy, et al., 2010, *J Infect Dis*, 202 (7):1050-1058; Bubeck Wardenburg and Schneewind, 2008, *J Exp Med*, 205 (2):287-294; Ragle and Bubeck Wardenburg, 2009, *J Infect Dis*, 176 (6):1531-1537); iii) Antibodies to H35L protect mice from toxin and partially protect against bacterial challenge (Menzies and Kernodle, 1996; *Infect Immun*, 64 (5):1839-1841). While the H35 mutation largely abrogates the lytic activity of Hla, a single point mutation is not considered sufficiently safe to be developed as vaccine for human use.

WO 2012/109167A1 describes a rationally designed mutant vaccine for Hla referred to as AT62. Immunization of mice with AT62 protected the animals against *S. aureus* lethal sepsis and pneumonia (Adhikari, et al., 2012, *PLoS One*, 7 (6):e38567). Furthermore, antibodies raised against AT62 protected mice from lethal sepsis induced by *S. aureus* (Adhikari, et al., 2012, *PLoS One*, 7 (6):e38567).

Panton-Valentine Leukocidin (PVL): PVL is a member of a family of bicomponent cytolytic toxins known as leukotoxins that is produced by several CA-MRSA lineages (Diep and Otto, 2008, *Trends Microbiol*, 16 (8):361-369). The bi-component hemolysins and leukotoxins, play an important role in staphylococcal immune evasion. These toxins kill key immune cells and cause tissue destruction, thereby often weakening the host during the first stage of infection and promoting bacterial dissemination and metastatic growth in distant organs. The two PVL components LukS-PV and LukF-PV are secreted separately, and form the pore-forming octameric complex upon binding of LukS-PV to its receptor and subsequent binding of LukF-PV to LukS-PV (Miles, et al., 2002, *Protein Sci*, 11 (4):894-902; Pedelacq, et al., 2000, *Proc Natl Acad Sci USA*, 109 (4): 1281-1286). Targets of PVL are polymorphonuclear phagocytes (PMN), monocytes, and macrophages. Epidemiologically, PVL is associated with primary skin infections, such as furunculosis and severe necrotizing pneumonia that rapidly progresses towards acute respiratory distress syndrome. The role of PVL in skin, bone, and lung infections has been shown in animal models (Brown, et al., 2009 *Clin Microbiol Infect*, 15 (2):156-164; Cremieux, et al., 2009, *PLoS ONE*, 4 (9):e7204; Diep, et al., 2010, *Proc Natl Acad Sci USA*, 107 (12):5587-5592; Tseng, et al., 2009 *PLoS ONE*, 4 (7):e6387; Varshney, et al., 2010, *J Infect Dis* 1; 201(1):92-6). PVL-positive CA-MRSA affect healthy children or young adults that had neither any recent contact with health care facilities nor with any risk factors with a mortality of up to 75% (Gillet, et al., 2002, *Lancet*, 359 (9308):753-759; Lina, et al., 1999, *Clin Infect Dis*, 29 (5):1128-1132).

PCT application No. PCT/US12/67483 discloses rationally designed mutants vaccine for LukS-PV and LukF-PV. Immunization of mice with these mutants protected the animals against *S. aureus* lethal sepsis (Karauzum, et al., 2013, *PLoS ONE*, 8 (6):e65384). Furthermore, antibodies raised against LukS-PV mutant protected mice from lethal sepsis induced by *S. aureus* (Karauzum, et al., 2013, *PLoS ONE*, 8 (6):e65384).

*Staphylococcus aureus* enterotoxins: Superantigens (SAgs) constitute a large family of pyrogenic toxins composed of staphylococcal enterotoxins (SEs) and toxic shock syndrome toxin 1 (TSST-1) (Johns and Khan, 1988, *J Bacteriol*, 170 (9):4033-4039). In contrast to conventional antigens that undergo proteolytic processing by antigen presenting cells and are presented as MHC/peptide complex to T cells, SAgs cross link TCR with MHC Class II and activate up to 30% of T cells (Choi, et al., 1989, *Proc Natl Acad Sci USA*, 86 (22):8941-8; Marrack and Kappler, 1990, *Science*, 248 (4959):1) leading to massive release of cytokines and chemokines, enhanced expression as well as activation of cell-adhesion molecules, increased T-cell proliferation, and eventually T-cell apoptosis/anergy. This sequence of events can culminate in Toxic Shock Syndrome (TSS), a life threatening condition (Todd, et al., 1978, *Lancet*, 2 (8100):1116-1118) characterized by rash, hypotension, fever, and multisystem dysfunction (Bohach, et al., 1990, *Crit Rev Microbiol*, 17 (4):251-272). Antibodies play an important role in protection against TSS (Bonventre, et al., 1984, *J Infect Dis*, 150 (5):662-666; Notermans, et al., 1983, *J Clin Microbiol*, 18 (5):1055-1060), thus individuals that do not seroconvert towards the offending toxin due to hyporesponsive T-cells (Mahlknecht, et al., 1996, *Hum Immunol*, 45 (1):42-4) and/or T-cell dependent B-cell apoptosis (Hofer, et al., 1996, *Proc Natl Acad Sci USA*, 93 (11):5425-5430) are more likely to experience recurring bouts. Clonal deletion of CD4 T cells can further impair effective antibody response to other *S. aureus* antigens. Furthermore, at lower non-TSS inducing concentrations SAgs impact the virulence of *S. aureus* strains through induction of a local excessive inflammatory response. Attenuated mutants of SEs and TSST-1 have been developed that are deficient in binding to MHC-class II molecules. These mutants can serve as a vaccine for *S. aureus* infections as well as toxic shock syndrome by inducing neutralizing antibodies against superantigens.

SUMMARY

In one aspect, the disclosure provides a recombinant peptide that can include a *Staphylococcus aureus* delta toxin peptide or a mutant, fragment, variant or derivative thereof (DT); a *Staphylococcus aureus* phenol soluble modulin peptide or a mutant, fragment, variant or derivative thereof (PSM); or a fusion of a DT and a PSM; where the peptide is attenuated relative to wild-type DT, PSM, or both, and where the peptide can elicit an anti-*Staphylococcus aureus* immune response when administered to a subject. In certain aspects, surfactant properties of the DT, PSM, or both, is reduced, while maintaining immunogenicity. In certain aspects, hydrophobicity is reduced while maintaining the peptide's alpha-helical structure. In certain aspects, at least one hydrophobic amino acid is replaced with a less hydrophobic amino acid, for example, valine (V), leucine (L), isoleucine (I), phenylalanine (F), or methionine (M) can be replaced with glycine or alanine.

The disclosure provides a DT that includes the amino acid sequence MAQDX$_5$X$_6$STX$_9$GDX$_{12}$X$_{13}$KWX$_{16}$X$_{17}$DTX$_{20}$NKFTKK (SEQ ID NO: 39), where at least one of X X$_5$, X$_6$, X$_9$, X$_{12}$, X$_{13}$, X$_{16}$, X$_{17}$, or X$_{20}$ includes an amino acid substitution relative to SEQ ID NO: 1, and where X$_5$ is isoleucine (I), glycine (G) or alanine (A), X$_6$ is I, G, or A, X$_9$ is I, G, or A, X$_{12}$ is leucine (L), G, or V, X$_{13}$ is valine (V), G, or A, X$_{16}$ is I, G, or A, X$_{17}$ is I, G, or A, and X$_{20}$ is V, G, or A. In certain aspects the peptide includes the amino acid sequence SEQ ID NO: 2. In certain aspects the peptide includes the amino acid sequence SEQ ID NO: 4. In certain aspects the peptide includes the amino acid sequence SEQ ID NO: 3. In certain aspects the peptide includes the amino acid sequence SEQ ID NO: 5.

The disclosure further provides a PSM that can be PSMα1, PSMα2, PSMα3, PSMα4, PSMβ1, PSMβ2, PSM-mec, or any combination of two or more PSMs.

The disclosure provides a PSMα1 mutant including the amino acid sequence X$_1$GX$_3$X$_4$AGX$_7$X$_8$KX$_{10}$X$_{11}$KSX$_{14}$X$_{15}$EQX$_{18}$TGK (SEQ ID NO: 40), where at least one of X$_1$, X$_3$, X$_4$, X$_7$, X$_8$, X$_{10}$, X$_{11}$, X$_{14}$, X$_{15}$, or X$_{18}$ includes an amino acid substitution relative to SEQ ID NO: 38, and where X$_1$ is methionine (M), G, or A, X$_3$ is I, G, or A, X$_4$ is I, G, or A, X$_7$ is I, G, or A, X$_8$ is I, G, or A, X$_{10}$ is V, G, or A, X$_{11}$ is I, G, or A, X$_{14}$ is L, G, or A, X$_{15}$ is I, G, or A, and X$_{18}$ is F, G, or A. The disclosure provides a PSMα2 mutant including the amino acid sequence X$_1$GX$_3$X$_4$AGX$_7$X$_8$X$_{10}$X$_{11}$KGX$_{14}$X$_{15}$EKX$_{18}$TGK (SEQ ID NO: 41), where at least one of X$_1$, X$_3$, X$_4$, X$_7$, X$_8$, X$_{10}$, X$_{11}$, X$_{14}$, X$_{15}$, or X$_{18}$ includes an amino acid substitution relative to SEQ ID NO: 12, and where X$_1$ is M, G, or A, X$_3$ is I, G, or A, X$_4$ is I, G, or A, X$_7$ is I, G, or A, X$_8$ is I, G, or A, X$_{10}$ is F, G, or A, X$_{11}$ is I, G, or A, X$_{14}$ is L, G, or A, X$_{15}$ is I, G, or A, and X$_{18}$ is F, G, or A. The disclosure provides a PSMα3 mutant including the amino acid sequence X$_1$EX$_3$X$_4$AKX$_7$X$_8$KX$_{10}$X$_{11}$KDX$_{14}$X$_{15}$GKX$_{18}$X$_{19}$GNN (SEQ ID NO: 42), where at least one of X$_1$, X$_3$, X$_4$, X$_7$, X$_8$, X$_{10}$, X$_{11}$, X$_{14}$, X$_{15}$, X$_{18}$, or X$_{19}$ includes an amino acid substitution relative to SEQ ID NO: 6, and where X$_1$ is M, G, or A, X$_3$ is F, G, or A, X$_4$ is V, G, or A, X$_7$ is L, G, or A, X$_8$ is F, G, or A, X$_{10}$ is F, G, or A, X$_{11}$ is F, G, or A, X$_{14}$ is L, G, or A, X$_{15}$ is L, G, or A, X$_{18}$ is F, G, or A, and X$_{19}$ is L, G, or A. In certain aspects the peptide includes the amino acid sequence SEQ ID NO: 7. In certain aspects the peptide includes the amino acid sequence SEQ ID NO: 9. In certain aspects the peptide includes the amino acid sequence SEQ ID NO: 8. In certain aspects the peptide includes the amino acid sequence SEQ ID NO: 10. In certain aspects the peptide includes the amino acid sequence e SEQ ID NO: 11. The disclosure provides a PSMα4 mutant including the amino acid sequence X$_1$AX$_3$X$_4$GTX$_7$X$_8$KX$_{10}$X$_{11}$KAX$_{14}$X$_{15}$DX$_{17}$X$_{18}$AK (SEQ ID NO: 43), where at least one of X$_1$, X$_3$, X$_4$, X$_7$, X$_8$, X$_{10}$, X$_{11}$, X$_{14}$, X$_{15}$, X$_{17}$, or X$_{18}$ includes an amino acid substitution relative to SEQ ID NO: 14, and where X$_1$ is M, G, or A, X$_3$ is I, G, or A, X$_4$ is V, G, or A, X$_7$ is I, G, or A, X$_8$ is I, G, or A, X$_{10}$ is I, G, or A, X$_{11}$ is I, G, or A, X$_{14}$ is I, G, or A, X$_{15}$ is I, G, or A, X$_{17}$ is I, G, or A, and X$_{18}$ is F, G, or A. The disclosure provides a PSMf31 mutant including the amino acid sequence MEGX$_4$X$_5$NAX$_8$KD-TX$_{12}$TAAX$_{16}$NNDGAKLGTSIVNIVENGVGLLSKLFGF (SEQ ID NO: 44), where at least one of X$_4$, X$_5$, X$_8$, X$_{12}$, or X$_{16}$ includes an amino acid substitution relative to SEQ ID NO: 15, and where X$_4$ is L, G, or A, X$_5$ is F, G, or A, X$_8$ is I, G, or A, X$_{12}$ is V, G, or A, and X$_{16}$ is I, G, or A. The disclosure provides a PSMβ2 mutant including the amino acid sequence MTGX$_4$AEAX$_8$AN-TX$_{12}$QAAQQHDSVKX$_{23}$GTSIVDIVANGVGLLGKLFGF (SEQ ID NO: 45), where at least one of X$_4$, X$_8$, X$_{12}$, or X$_{23}$ includes an amino acid substitution relative to SEQ ID NO: 16, and where X$_4$ is L, G, or A, X$_8$ is I, G, or A, X$_{12}$ is V, G, or A, and X$_{23}$ is L, G, or A.

The disclosure further provides a multivalent oligopeptide that includes a fusion of two or more *Staphylococcus aureus*-derived peptides, or mutants, fragments, variants, or derivatives thereof arranged in any order, where the two or more *Staphylococcus aureus*-derived peptides, or mutants, fragments, variants, or derivatives thereof can be the same or different, and where the multivalent oligopeptide includes two or more of: a wild-type DT, or a mutant DT, e.g., as described herein; a wild-type PSM, or a mutant PSM, e.g., as described herein; an alpha hemolysin polypeptide or mutant, fragment, variant, or derivative thereof; a leukocidin polypeptide or mutant, fragment, variant, or derivative thereof; or a superantigen (SAg) polypeptide, or mutant, fragment, variant, or derivative thereof.

A multivalent oligopeptide as provided herein can include an alpha hemolysin polypeptide or mutant, fragment, variant, or derivative thereof such as the amino acid sequence SEQ ID NO: 46 (AT-62). A multivalent oligopeptide as provided herein can include a Panton-Valentine leukocidin (PVL) LukS-PV subunit such as an amino acid sequence at least 90% identical to SEQ ID NO: 47, a LukS-Mut9 (SEQ ID NO: 54), a Panton-Valentine leukocidin (PVL) LukF-PV subunit such as an amino acid sequence at least 90% identical to SEQ ID NO: 48, a LukF-Mut-1 (SEQ ID NO: 55), or a combination thereof. A multivalent oligopeptide as provided herein can include a staphylococcal enterotoxin B (SEB) or mutant, fragment, variant, or derivative thereof such as an amino acid sequence at least 90% identical to SEQ ID NO: 49, a staphylococcal enterotoxin A (SEA) or mutant, fragment, variant, or derivative thereof such as an amino acid sequence at least 90% identical to SEQ ID NO:

50, a staphylococcal toxic shock syndrome toxin-1 or mutant, fragment, variant, or derivative thereof such as an amino acid sequence at least 90% identical to SEQ ID NO: 51, or any combination thereof.

A multivalent oligopeptide as provided herein can include linkers connecting the two or more *Staphylococcus aureus*-derived peptides, or mutants, fragments, variants, or derivatives thereof are associated via a linker. The linker can include, e.g., at least one, but no more than 50 amino acids selected from the group consisting of glycine, serine, alanine, and a combination thereof. In certain aspects the linker includes $(GGGS)_n$ or $(GGGGS)_n$, where n is a integer from 1 to 10. Exemplary multivalent oligopeptides provided by the disclosure include, without limitation, the amino acid sequence SEQ ID NO: 18, SEQ ID NO: 20, SEQ ID NO: 22, SEQ ID NO: 23, SEQ ID NO: 26, SEQ ID NO: 29, SEQ ID NO: 32, SEQ ID NO: 33, SEQ ID NO. 34, SEQ ID NO: 35, SEQ ID NO: 36, SEQ ID NO: 37, or any combination thereof.

Any peptide or oligopeptide provided by the disclosure can further include a heterologous peptide or polypeptide including, but not limited to a His-tag, a ubiquitin tag, a NusA tag, a chitin binding domain, a B-tag, a HSB-tag, green fluorescent protein (GFP), a calmodulin binding protein (CBP), a galactose-binding protein, a maltose binding protein (MBP), cellulose binding domains (CBD's), an avidin/streptavidin/Strep-tag, trpE, chloramphenicol acetyltransferase, lacZ (β-Galactosidase), a FLAG™ peptide, an S-tag, a T7-tag, a fragment of any of the heterologous peptides, or a combination of two or more of the heterologous peptides. In certain aspects the heterologous peptide or polypeptide includes an immunogen, a T-cell epitope, a B-cell epitope, a fragment thereof, or a combination thereof.

Any peptide or oligopeptide provided by the disclosure can further include an immunogenic carbohydrate, e.g., a saccharide. The immunogenic carbohydrate can be a capsular polysaccharide or a surface polysaccharide. The immunogenic carbohydrate can include, without limitation, capsular polysaccharide (CP) serotype 5 (CP5), CP8, poly-N-acetylglucosamine (PNAG), poly-N-succinyl glucosamine (PNSG), Wall Teichoic Acid (WTA), Lipoteichoic acid (LTA), a fragment of any of the immunogenic carbohydrates, and a combination of two or more of the immunogenic carbohydrates. In certain aspects the immunogenic carbohydrate is conjugated to the oligopeptide.

The disclosure further provides an isolated polynucleotide that includes a nucleic acid any peptide or oligopeptide provided herein, and any combination thereof. In certain aspects the polynucleotide can further include a heterologous nucleic acid, e.g., a promoter operably associated with the nucleic acid encoding the multivalent oligopeptide, DT, PSM, or any combination thereof. The disclosure provides a vector that includes the polynucleotide provided by the disclosure, e.g., a plasmid. The disclosure provides a host cell that includes a vector provided by the disclosure. The host cell can be, e.g., a bacterium, e.g., *Escherichia coli*, an insect cell, a mammalian cell or a plant cell.

The disclosure further provides a method of producing a multivalent oligopeptide, DT, PSM, or any combination thereof as provided herein, that includes culturing a host cell and recovering the oligopeptide, DT, PSM, or any combination thereof.

The disclosure further provides a composition that includes any peptide, oligopeptide, or combination thereof provided by the disclosure, and a carrier. In certain aspects the composition further includes an adjuvant that can be, without limitation, alum, aluminum hydroxide, aluminum phosphate, or a glucopyranosyl lipid A-based adjuvant. In certain aspects the composition further includes an immunogen that can be, without limitation, a bacterial antigen such as a pore forming toxin, a superantigen, a cell surface protein, a fragment of any of the bacterial antigens, or a combination of two or more of the bacterial antigens.

The disclosure further provides a method of inducing a host immune response against *Staphylococcus aureus* that includes administering to a subject in need of the immune response an effective amount of the composition of the disclosure. In certain aspects the immune response is an antibody response, an innate response, a humoral response, a cellular response, and a combination of two or more of the immune responses. The disclosure further provides a method of preventing or treating a Staphylococcal, Streptococcal, or Enterococcal disease or infection in a subject that includes administering to a subject in need thereof the composition of the disclosure. The infection can be, e.g., a localized or systemic infection of skin, soft tissue, blood, or an organ, or can be auto-immune in nature. In certain aspects the disease is a respiratory disease, e.g., pneumonia. In certain aspects the disease is sepsis.

A subject to be treated by the methods of the disclosure can be a mammal, e.g., a human, bovine, or canine. The composition can be administered to the subject via intramuscular injection, intradermal injection, intraperitoneal injection, subcutaneous injection, intravenous injection, oral administration, mucosal administration, intranasal administration, or pulmonary administration.

The disclosure further provides a method of producing a vaccine against *S. aureus* infection that includes: isolating a peptide or oligopeptide as provided by this disclosure, or any combination thereof; and combining the peptide, oligopeptide, or any combination thereof with an adjuvant.

BRIEF DESCRIPTION OF THE DRAWINGS/FIGURES

FIG. 1: A) Helical wheel representation of PSM-α1-4, PSM-β1&2, and δ-toxin showing the hydrophobic and hydrophilic surfaces. B) Mutation strategies for the δ-toxin and PSM-α3. Amino acids L and V, conserved in hydrophobic faces, are replaced either by ala (A) or Gly (G) individually or in combination (gly-ala). The predicted decrease in hydrophobicity and hydrophobic moment are shown for each mutant. Polar amino acids are represented in red (D, E: – charge) and blue (R, K: + charge); Polar amino acids in pink/violet (Q, N, T); Hydrophobic in yellow (F, L, I) and such that are not disturbing hydrophobicity are marked in grey (A) or in green (P) for their aromatic side-chain. C) Helical wheel representation of PSM-mec showing the hydrophobic and hydrophilic surfaces.

Figure 2:
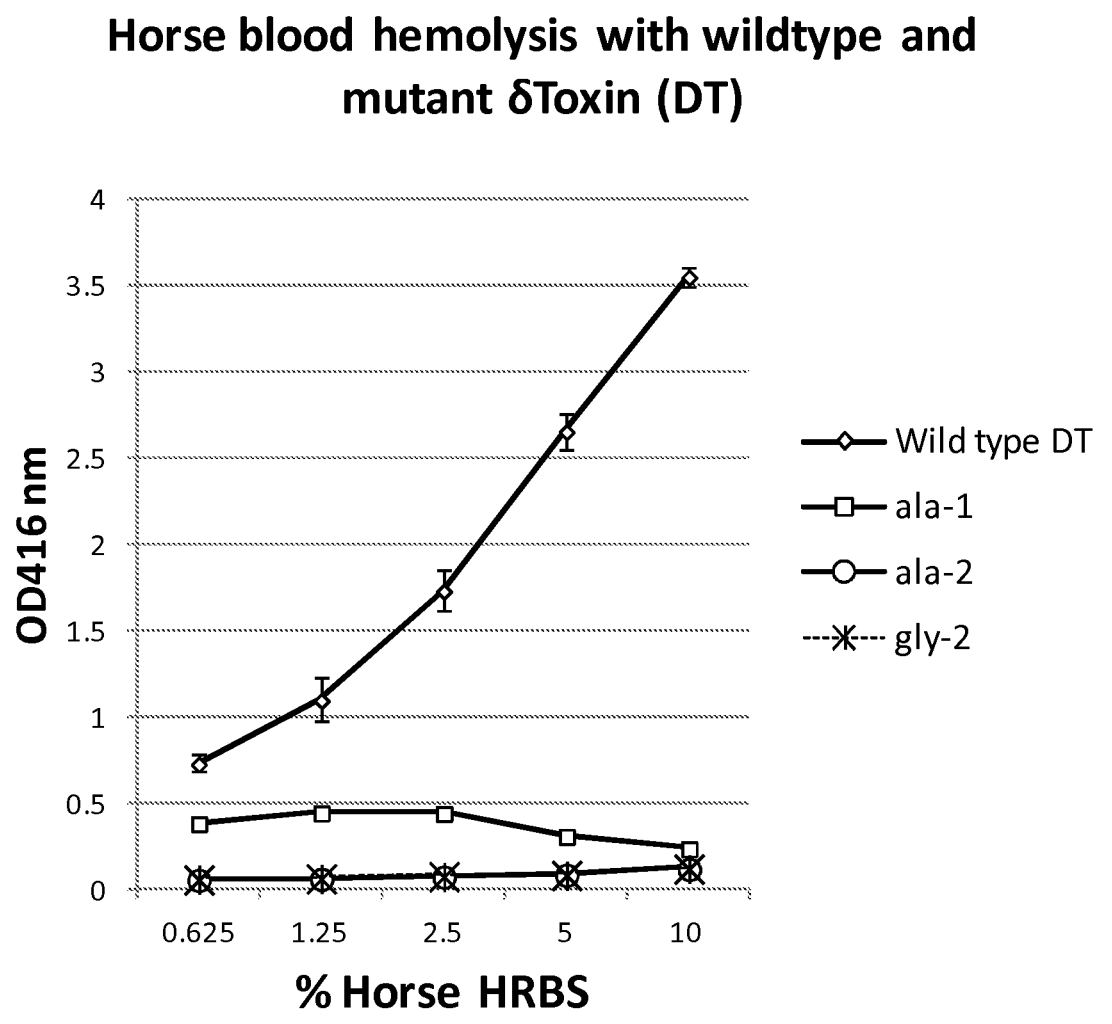

FIG. 2: Delta toxin mutants toxicity assay. WT and mutants at concentration of 12.5 μg/ml were tested in different % of horse RBC. Hemolysis ODs were measured at 416 nm.

Figure 3:
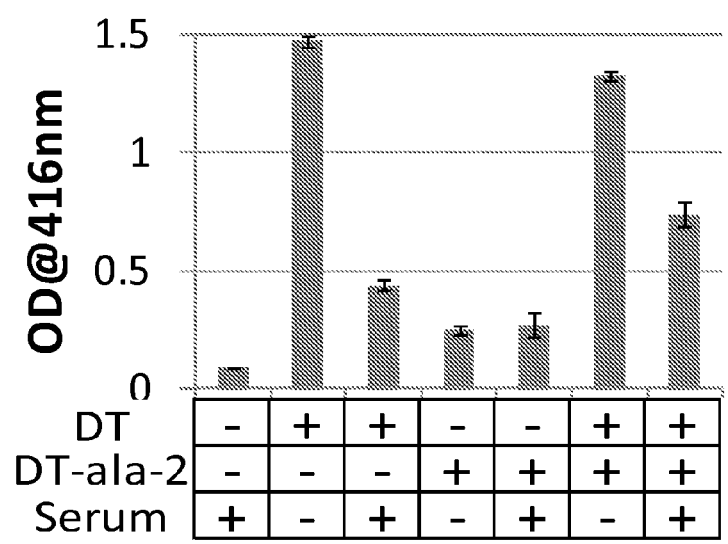

FIG. 3: DT-ala2 mutant is highly attenuated while retaining binding to human neutralizing antibodies (compare $3^{rd}$ and $7^{th}$ bar).

FIG. 4: PSM mutants toxicity assay. WT and mutants at different concentration were tested in different 5% of horse RBC. Hemolysis ODs were measured at 416 nm.

FIG. 5: A) Schematic of three fusion proteins generated with flexible linkers (G4S, denoted as L) and a 6xHis tag. B) Schematic of the secondary structure of AT62-DT-PSM construct. C) Candidate peptides were expressed in *E. coli* and tested by Western blot using an AT62 specific mAb.

Lanes 1 and 2: AT62_DT_PSM; 3 and 4: AT62_PSM; 5 and 6: AT62_DT (Two clones for each construct are shown).

FIG. 6: Antibody response of mice immunized with AT62-PSM and AT62-DT against wild type peptides or full length alpha hemolysin (Hla).

Figure 7:
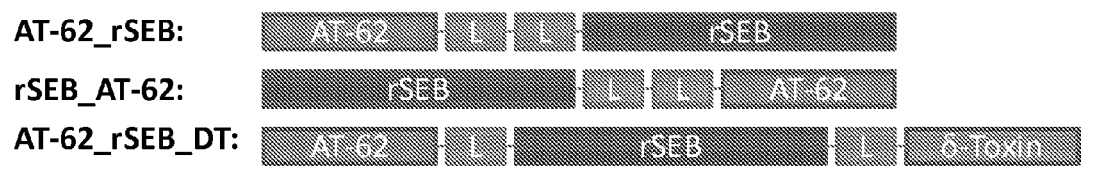

FIG. 7: A) Schematic of three fusion proteins: AT-62, rSEB and DT generated with flexible linkers (G4S, denoted as L).

Figure 8:
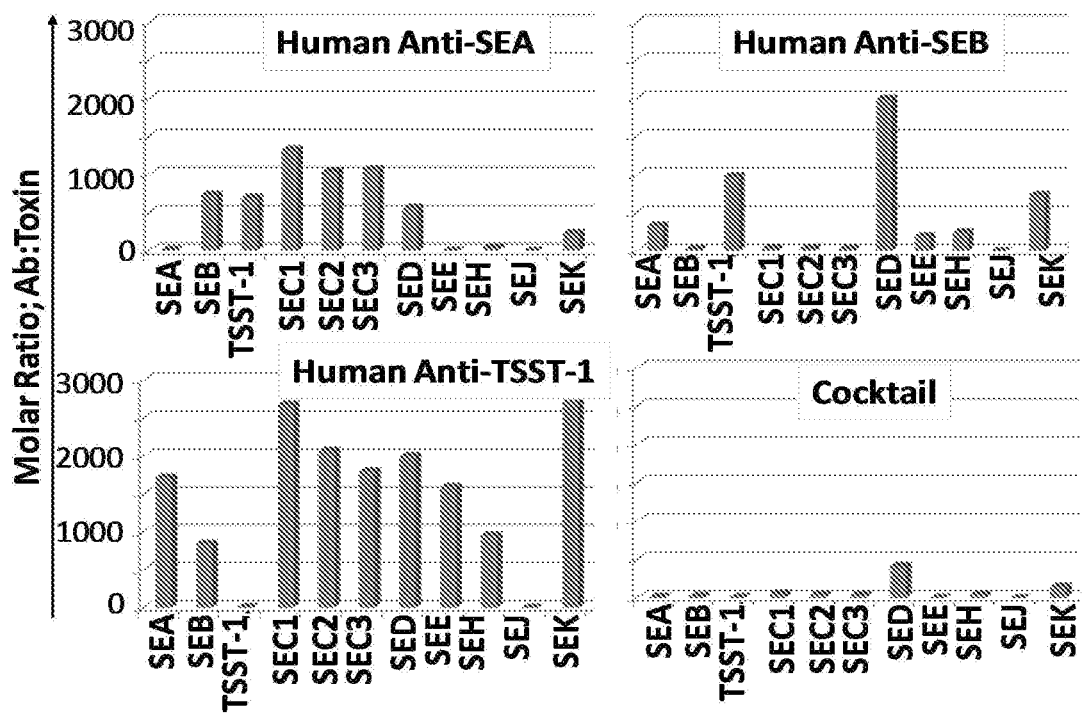

FIG. 8: Human antibodies to SEA, SEB, and TSST-1 were affinity purified from human IVIG and used in toxin neutralization assays with human PBMC against the SAgs shown on the X axes. The Y axis shows the molar ratio of antibody to toxin required for 50% inhibition of superantigenic activity of the respective SAg on the X axis. The panel titled Cocktail shows the activity of the combination of the three antibodies. Note that lower molar ratio indicates higher neutralizing activity towards the respective toxin.

DETAILED DESCRIPTION

I. Definitions

It is to be noted that the term "a" or "an" entity refers to one or more of that entity; for example, "a polynucleotide," is understood to represent one or more polynucleotides. As such, the terms "a" (or "an"), "one or more," and "at least one" can be used interchangeably herein.

Furthermore, "and/or" where used herein is to be taken as specific disclosure of each of the two specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range. Unless otherwise indicated, amino acid sequences are written left to right in amino to carboxy orientation. The headings provided herein are not limitations of the various aspects or embodiments of the disclosure, which can be had by reference to the specification as a whole. Accordingly, the terms defined immediately below are more fully defined by reference to the specification in its entirety.

Wherever embodiments are described with the language "comprising," otherwise analogous embodiments described in terms of "consisting of" and/or "consisting essentially of" are also provided.

Amino acids are referred to herein by their commonly known three letter symbols or by the one-letter symbols recommended by the IUPAC-IUB Biochemical Nomenclature Commission. Nucleotides, likewise, are referred to by their commonly accepted single-letter codes.

The terms "nucleic acid" or "nucleic acid fragment" refers to any one or more nucleic acid segments, e.g., DNA or RNA fragments, present in a polynucleotide or construct. Two or more nucleic acids of the disclosure can be present in a single polynucleotide construct, e.g., on a single plasmid, or in separate (non-identical) polynucleotide constructs, e.g., on separate plasmids. Furthermore, any nucleic acid or nucleic acid fragment can encode a single polypeptide, e.g., a single antigen, cytokine, or regulatory polypeptide, or can encode more than one polypeptide, e.g., a nucleic acid can encode two or more polypeptides. In addition, a nucleic acid can encode a regulatory element such as a promoter or a transcription terminator, or can encode a specialized element or motif of a polypeptide or protein, such as a secretory signal peptide or a functional domain.

The term "polynucleotide" is intended to encompass a singular nucleic acid or nucleic acid fragment as well as plural nucleic acids or nucleic acid fragments, and refers to an isolated molecule or construct, e.g., a virus genome (e.g., a non-infectious viral genome), messenger RNA (mRNA), plasmid DNA (pDNA), or derivatives of pDNA (e.g., minicircles as described in (Darquet, A-M et al., *Gene Therapy* 4:1341-1349, 1997) comprising a polynucleotide. A polynucleotide can be provided in linear (e.g., mRNA), circular (e.g., plasmid), or branched form as well as double-stranded or single-stranded forms. A polynucleotide can comprise a conventional phosphodiester bond or a non-conventional bond (e.g., an amide bond, such as found in peptide nucleic acids (PNA)).

As used herein, the term "polypeptide" is intended to encompass a singular "polypeptide" as well as plural "polypeptides," and comprises any chain or chains of two or more amino acids. Thus, as used herein, a "peptide," an "oligopeptide," a "dipeptide," a "tripeptide," a "protein," an "amino acid chain," an "amino acid sequence," "a peptide subunit," or any other term used to refer to a chain or chains of two or more amino acids, are included in the definition of a "polypeptide," (even though each of these terms can have a more specific meaning) and the term "polypeptide" can be used instead of, or interchangeably with any of these terms. The term further includes polypeptides which have undergone post-translational modifications, for example, glycosylation, acetylation, phosphorylation, amidation, derivatization by known protecting/blocking groups, proteolytic cleavage, or modification by non-naturally occurring amino acids.

The terms "delta toxin" or "DT" as used herein, and unless otherwise indicated, encompass wild-type delta toxin peptides as well as mutants, fragments, variants or derivatives thereof. The terms "phenol-soluble modulin," "PSM," PSMα1, PSMα2, PSMα3, PSMα4, PSMβ1, PSMβ2, and PSM-mec as used herein, and unless otherwise indicated, encompass wild-type phenol-soluble modulin peptides as well as mutants, fragments, variants or derivatives thereof. By "corresponding wild-type DT" or "corresponding wild-type PSM" is meant the native DT or PSM peptide from which a mutant peptide subunit was derived.

The term "multivalent oligopeptide" as used herein refers to a fusion protein comprising two or more staphylococcal proteins, e.g., DT, PSM, alpha hemolysin, leukocidin, superantigen, or any fragments, variants, derivatives, or mutants thereof fused together as a single polypeptide in any order. An oligopeptide can include other heterologous peptides as described elsewhere herein. Other peptides for inclusion in a multivalent oligopeptide provided herein include various other staphylococcal toxins or mutants fragments, variants, or derivatives thereof, described elsewhere herein or in PCT Publication Nos. WO 2012/109167A1 and WO 2013/082558A1, which are both incorporated by reference herein in their entireties.

This disclosure provides specific DT and PSM peptides as well as multivalent oligopeptides that can, but do not necessarily include either a wild-type or mutant DT, PSM, or any combination thereof. The collection of peptides and oligopeptides provided by the disclosure are collectively referred to herein as a "multivalent oligopeptide, DT, and/or PSM," or a "multivalent oligopeptide, DT, PSM, or any combination thereof." These collective references are meant to include, without limitation, any one peptide or oligopeptide as provided herein, or two, three, four, or more peptides or oligopeptides as provided herein.

The terms "fragment," "mutant," "derivative," or "variant" when referring to a multivalent oligopeptide, DT, and/or PSM of the present disclosure include any polypeptide which retains at least some of the immunogenicity or antigenicity of the source protein or proteins. Fragments of multivalent oligopeptides, DTs, and/or PSMs as described herein include proteolytic fragments, deletion fragments or fragments that exhibit increased solubility during expression, purification, and/or administration to an animal. Fragments of multivalent oligopeptides, DTs, and/or PSMs as described herein further include proteolytic fragments or deletion fragments which exhibit reduced pathogenicity or toxicity when delivered to a subject. Polypeptide fragments further include any portion of the polypeptide which comprises an antigenic or immunogenic epitope of the source polypeptide, including linear as well as three-dimensional epitopes.

An "epitopic fragment" of a polypeptide is a portion of the polypeptide that contains an epitope. An "epitopic fragment" can, but need not, contain amino acid sequence in addition to one or more epitopes.

The term "variant," as used herein, refers to a polypeptide that differs from the recited polypeptide due to amino acid substitutions, deletions, insertions, and/or modifications. Non-naturally occurring variants can be produced using art-known mutagenesis techniques. In some embodiments, variant polypeptides differ from an identified sequence by substitution, deletion or addition of three amino acids or fewer. Such variants can generally be identified by modifying a polypeptide sequence, and evaluating the antigenic or pathogenic properties of the modified polypeptide using, for example, the representative procedures described herein. In some embodiments, variants of a multivalent oligopeptide, DT, and/or PSM form a protein complex which is less toxic than the wild-type complex.

Polypeptide variants disclosed herein exhibit at least about 85%, 90%, 94%, 95%, 96%, 97%, 98%, 99% or 99.9% sequence identity with identified polypeptide. Variant polypeptides can comprise conservative or non-conservative amino acid substitutions, deletions or insertions. Variants can comprise multivalent oligopeptides, DTs, and/or PSMs identical to the various wild-type staphylococcal proteins except for at least 1, 2, 3, 4, 5, 6, 7, 8, 9, 10, 15, 20, or more amino acid substitutions, including specific mutations described elsewhere herein, where the substitutions render complex less toxic than a corresponding wild-type protein complex. Derivatives of multivalent oligopeptides, DTs, and/or PSMs as described herein are polypeptides which have been altered so as to exhibit additional features not found on the native polypeptide. Examples include fusion proteins. An analog is another form of a multivalent oligopeptide, DT, and/or PSM described herein. An example is a proprotein which can be activated by cleavage of the proprotein to produce an active mature polypeptide.

Variants can also, or alternatively, contain other modifications, whereby, for example, a polypeptide can be conjugated or coupled, e.g., fused to a heterologous amino acid sequence, e.g., a signal (or leader) sequence at the N-terminal end of the protein which co-translationally or post-translationally directs transfer of the protein. The polypeptide can also be conjugated or produced coupled to a linker or other sequence for ease of synthesis, purification or identification of the polypeptide (e.g., 6-His), or to enhance binding of the polypeptide to a solid support. For example, the polypeptide can be conjugated or coupled to an immunoglobulin Fc region. The polypeptide can also be conjugated or coupled to a sequence that imparts or modulates the immune response to the polypeptide (e.g., a T-cell epitope, B-cell epitope, cytokine, chemokine, etc.) and/or enhances uptake and/or processing of the polypeptide by antigen presenting cells or other immune system cells. The polypeptide can also be conjugated or coupled to other polypeptides/epitopes from *Staphylococcus* sp. and/or from other bacteria and/or other viruses to generate a hybrid immunogenic protein that alone or in combination with various adjuvants can elicit protective immunity to other pathogenic organisms. The polypeptide can also be conjugated or coupled to moieties which confer greater stability or improve half life such as, but not limited to albumin, an immunoglobulin Fc region, polyethylene glycol (PEG), and the like. The polypeptide can also be conjugated or coupled to moieties (e.g., immunogenic carbohydrates, e.g., a capsular polysaccharide or a surface polysaccharide) from *Staphylococcus* sp. and/or from other bacteria and/or other viruses to generate a modified immunogenic protein that alone or in combination with one or more adjuvants can enhance and/or synergize protective immunity. In certain embodiments, the polypeptide described herein further comprises an immunogenic carbohydrate. In one embodiment, the immunogenic carbohydrate is a saccharide.

The term "saccharide" throughout this specification can indicate polysaccharide or oligosaccharide and includes both. Polysaccharides of the disclosure can be isolated from bacteria and can be sized by known methods. For example, full length polysaccharides can be "sized" (e.g., their size can be reduced by various methods such as acid hydrolysis treatment, hydrogen peroxide treatment, sizing by EMULSIFLEX® followed by a hydrogen peroxide treatment to generate oligosaccharide fragments or microfluidization). Polysaccharides can be sized in order to reduce viscosity in polysaccharide samples and/or to improve filterability for conjugated products. Oligosaccharides have a low number of repeat units (e.g., 5-30 repeat units) and are typically hydrolyzed polysaccharides. Polysaccharides of the disclosure can be produced recombinantly.

*S. aureus* capsular antigens are surface associated, limited in antigenic specificity, and highly conserved among clinical isolates. In one embodiment, the immunogenic carbohydrate of the disclosure is a capsular polysaccharide (CP) of *S. aureus*. In one embodiment, a capsular saccharide can be a full length polysaccharide, however in other embodiments it can be one oligosaccharide unit, or a shorter than native length saccharide chain of repeating oligosaccharide units. Serotyping studies of staphylococcal isolates have revealed several putative capsular serotypes, with types 5 and 8 (CP5 and CP8) being the most prevalent among isolates from clinical infections, accounting for about 25% and 50% of isolates recovered from humans, respectively (O'Riordan and Lee, Clinical Microbiology Reviews, January 2004, p.

218-234, Vol. 17, No. 1; Poutrel and Sutra, J Clin Microbiol. 1993 February; 31(2):467-9). The same isolates were also recovered from poultry, cows, horses and pigs (Tollersrud et al., J Clin Microbiol. 2000 August; 38(8):2998-3003; Cunnion K M et al., Infect Immun. 2001 November; 69(11): 6796-803). Type 5 and 8 capsular polysaccharides purified from the prototype strains Reynolds and Becker, respectively, are structurally very similar to each other and to the capsule made by strain T, described previously by Wu and Park (Wu and Park. 1971. J. Bacterial. 108:874-884). Type 5 has the structure (→4)-3-O-Ac-β-D-ManNAcA-(1→4)-α-L-FucNAc-(1→3)-β-D-FucNAc-(1→)$_n$ (Fournier, J. M., et al., 1987. Ann. Inst. Pasteur Microbiol. 138:561-567; Moreau, M., et al., 1990. Carbohydr. Res. 201:285-297), and type 8 has the structure (→3)-4-O-Ac-β-D-ManNAcA-(1→3)-α-L-FucNAc-(1→3)-β-D-FucNAc-(1→)$_n$ (Fournier, J. M., et al., 1984. Infect. Immun. 45:87-93). Type 5 and 8 polysaccharides differ only in the linkages between the sugars and in the sites of O-acetylation of the mannosaminuronic acid residues, yet they are serologically distinct.

Type 5 and 8 CP conjugated to a detoxified recombinant *Pseudomonas aeruginosa* exotoxin A carrier were shown to be highly immunogenic and protective in a mouse model (A Fattom et al., Infect Immun. 1993 March; 61(3): 1023-1032; A Fattom et al., Infect Immun. 1996 May; 64(5): 1659-1665) and passive transfer of the CP5-specific antibodies from the immunized animals induced protection against systemic infection in mice (Lee et al., Infect Immun. 1997 October; 65(10): 4146-4151) and against endocarditis in rats challenged with a serotype 5 *S. aureus* (Shinefield H et al., N Engl J Med. 2002 Feb. 14; 346(7):491-6). A bivalent CP5 and CP8 conjugate vaccine (StaphVAX®, Nabi Biopharmaceutical) was developed that provided 75% protection in mice against *S. aureus* challenge. The vaccine has been tested on humans (Fattom A I et al., Vaccine. 2004 Feb. 17; 22(7):880-7; Maira-Litrán T et al., Infect Immun. 2005 October; 73(10):6752-62). In certain embodiments, the recombinant peptide or multivalent oligopeptide of the disclosure is combined with or conjugated to an immunogenic carbohydrate (e.g., CP5, CP8, a CP fragment or a combination thereof).

Immunization with poly-N-acetylglucosamine (PNAG) (McKenney D. et al., Science. 1999 May 28; 284(5419): 1523-7) or poly-N-succinyl glucosamine (PNSG) (Tuchscherr L P. et al., Infect Immun. 2008 December; 76(12): 5738-44. Epub 2008 Sep. 22), both *S. aureus* surface carbohydrates, has been shown to generate at least partial protection against *S. aureus* challenge in experimental animal models. PNSG was identified as the chemical form of the *S. epidermidis* capsular polysaccharide/adhesin (PS/A) which mediates adherence of coagulase-negative staphylococci (CoNS) to biomaterials, serves as the capsule for strains of CoNS that express PS/A, and is a target for protective antibodies. PNSG is also made by *S. aureus*, where it is an environmentally regulated, in vivo-expressed surface polysaccharide and similarly serves as a target for protective immunity (McKenney D. et al., J. Biotechnol. 2000 Sep. 29; 83(1-2): 37-44). In certain embodiments of the disclosure, the immunogenic carbohydrate is a surface polysaccharide, e.g., poly-N-acetylglucosamine (PNAG), poly-N-succinyl glucosamine (PNSG), a surface polysaccharide fragment or a combination thereof.

Wall Teichoic Acid (WTA) is a prominent polysaccharide widely expressed on *S. aureus* strains (Neuhaus, F. C. and J. Baddiley, Microbiol Mol Biol Rev, 2003. 67(4):686-723) and antisera to WTA have been shown to induce opsonophagocytic killing alone and in presence of complement ((Thakker, M., et al., Infect Immun, 1998. 66(11): 5183-9), and Fattom et al, U.S. Pat. No. 7,754,225). WTA is linked to peptidoglycans and protrudes through the cell wall becoming prominently exposed on non-encapsulated strains such as USA300 responsible for most cases of community acquired MRSA (CA MRSA) in the US (Hidron, A. I., et al., Lancet Infect Dis, 2009. 9(6):384-92).

Lipoteichoic acid (LTA) is a constituent of the cell wall of Gram-positive bacteria, e.g., *Staphylococcus aureus*. LTA can bind to target cells non-specifically through membrane phospholipids, or specifically to CD14 and to Toll-like receptors. Target-bound LTA can interact with circulating antibodies and activate the complement cascade to induce a passive immune kill phenomenon. It also triggers the release from neutrophils and macrophages of reactive oxygen and nitrogen species, acid hydrolases, highly cationic proteinases, bactericidal cationic peptides, growth factors, and cytotoxic cytokines, which can act in synergy to amplify cell damage.

In certain embodiments, a surface polysaccharide is combined with or conjugated to a polypeptide of the disclosure. In certain embodiments the surface polysaccharide is, e.g., poly-N-acetylglucosamine (PNAG), poly-N-succinyl glucosamine (PNSG), Wall Teichoic Acid (WTA), Lipoteichoic acid (LPA), a fragment of any of said surface polysaccharides, or a combination of two or more of said surface polysaccharides.

The term "sequence identity" as used herein refers to a relationship between two or more polynucleotide sequences or between two or more polypeptide sequences. When a position in one sequence is occupied by the same nucleic acid base or amino acid in the corresponding position of the comparator sequence, the sequences are said to be "identical" at that position. The percentage "sequence identity" is calculated by determining the number of positions at which the identical nucleic acid base or amino acid occurs in both sequences to yield the number of "identical" positions. The number of "identical" positions is then divided by the total number of positions in the comparison window and multiplied by 100 to yield the percentage of "sequence identity." Percentage of "sequence identity" is determined by comparing two optimally aligned sequences over a comparison window and a homologous polypeptide from another isolate. In order to optimally align sequences for comparison, the portion of a polynucleotide or polypeptide sequence in the comparison window can comprise additions or deletions termed gaps while the reference sequence is kept constant. An optimal alignment is that alignment which, even with gaps, produces the greatest possible number of "identical" positions between the reference and comparator sequences. Percentage "sequence identity" between two sequences can be determined using the version of the program "BLAST 2 Sequences" which is available from the National Center for Biotechnology Information as of Sep. 1, 2004, which program incorporates the programs BLASTN (for nucleotide sequence comparison) and BLASTP (for polypeptide sequence comparison), which programs are based on the algorithm of Karlin and Altschul (*Proc. Natl. Acad. Sci. USA* 90(12):5873-5877, 1993). When utilizing "BLAST 2 Sequences," parameters that were default parameters as of Sep. 1, 2004, can be used for word size (3), open gap penalty (11), extension gap penalty (1), gap drop-off (50), expect value (10) and any other required parameter including but not limited to matrix option.

The term "epitope," as used herein, refers to portions of a polypeptide having antigenic or immunogenic activity in an animal, for example a mammal, for example, a human.

An "immunogenic epitope," as used herein, is defined as a portion of a protein that elicits an immune response in an animal, as determined by any method known in the art. The term "antigenic epitope," as used herein, is defined as a portion of a protein to which an antibody or T-cell receptor can immunospecifically bind its antigen as determined by any method well known in the art. Immunospecific binding excludes non-specific binding but does not necessarily exclude cross-reactivity with other antigens. Whereas all immunogenic epitopes are antigenic, antigenic epitopes need not be immunogenic.

As used herein, a "coding region" is a portion of nucleic acid which consists of codons translated into amino acids. Although a "stop codon" (TAG, TGA, or TAA) is not translated into an amino acid, it can be considered to be part of a coding region, but any flanking sequences, for example promoters, ribosome binding sites, transcriptional terminators, and the like, are outside the coding region.

The term "codon optimization" is defined herein as modifying a nucleic acid sequence for enhanced expression in the cells of the host of interest by replacing at least one, more than one, or a significant number, of codons of the native sequence with codons that are more frequently or most frequently used in the genes of that host. Various species exhibit particular bias for certain codons of a particular amino acid.

The terms "composition" or "pharmaceutical composition" can include compositions containing immunogenic polypeptides of the disclosure along with e.g., adjuvants or pharmaceutically acceptable carriers, excipients, or diluents, which are administered to an individual already suffering from S. aureus infection or an individual in need of immunization against S. aureus infection.

The term "pharmaceutically acceptable" refers to compositions that are, within the scope of sound medical judgment, suitable for contact with the tissues of human beings and animals without excessive toxicity or other complications commensurate with a reasonable benefit/risk ratio. In some embodiments, the polypeptides, polynucleotides, compositions, and vaccines described herein are pharmaceutically acceptable.

An "effective amount" is that amount the administration of which to an individual, either in a single dose or as part of a series, is effective for treatment or prevention. An amount is effective, for example, when its administration results in a reduced incidence of S. aureus infection relative to an untreated individual, as determined, e.g., after infection or challenge with infectious S. aureus, including, but is not limited to reduced bacteremia, reduced toxemia, reduced sepsis, reduced symptoms, increased immune response, modulated immune response, or reduced time required for recovery. This amount varies depending upon the health and physical condition of the individual to be treated, the taxonomic group of individual to be treated. (e.g., human, nonhuman primate, primate, etc.), the responsive capacity of the individual's immune system, the extent of treatment or protection desired, the formulation of the vaccine, a professional assessment of the medical situation, and other relevant factors. It is expected that the effective amount will fall in a relatively broad range that can be determined through routine trials. Typically a single dose is from about 10 µg to 10 mg/kg body weight of purified polypeptide or an amount of a modified carrier organism or virus, or a fragment or remnant thereof, sufficient to provide a comparable quantity of recombinantly expressed multivalent oligopeptide, DT, and/or PSM as described herein. The term "peptide vaccine" or "subunit vaccine" refers to a composition comprising one or more polypeptides described herein, which when administered to an animal are useful in stimulating an immune response against staphylococcal (e.g., S. aureus) infection.

The term "subject" is meant any subject, particularly a mammalian subject, for whom diagnosis, prognosis, immunization, or therapy is desired. Mammalian subjects include, but are not limited to, humans, domestic animals, farm animals, zoo animals such as bears, sport animals, pet animals such as dogs, cats, guinea pigs, rabbits, rats, mice, horses, cattle, bears, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and so on. In one embodiment, the subject is a human subject.

As used herein, a "subject in need thereof" refers to an individual for whom it is desirable to treat, i.e., to prevent, cure, retard, or reduce the severity of staphylococcal (e.g., S. aureus) disease symptoms, or result in no worsening of disease cause by S. aureus over a specified period of time, or both.

The terms "priming" or "primary" and "boost" or "boosting" as used herein to refer to the initial and subsequent immunizations, respectively, i.e., in accordance with the definitions these terms normally have in immunology. However, in certain embodiments, e.g., where the priming component and boosting component are in a single formulation, initial and subsequent immunizations are not be necessary as both the "prime" and the "boost" compositions are administered simultaneously.

II. Delta Toxin and Phenol-soluble Modulin Peptides and Multivalent Oligopeptides This disclosure provides recombinant oligopeptide fusion proteins comprised of peptide subunits derived from staphylococcal toxins and superantigens. In certain embodiments an oligopeptide as provided herein comprises a mutant or wild-type delta toxin peptide (DT) or a mutant or wild-type phenol-soluble modulin peptide (PSM). Wild-type DT and the six forms of PSM are presented in Table 1.

TABLE 1

WILD-TYPE DT AND PSMS

| | SEQUENCE | SEQ ID NO |
|---|---|---|
| delta toxin WT | MAQDIISTIGDLVKWIIDTVNKFTKK | 1 |
| PSMα1 WT | MGIIAGIIKVIKSLIEQFTGK | 38 |
| PSMα2 WT | MGIIAGIIKFIKGLIEKFTGK | 12 |
| PSMα3 WT | MEFVAKLFKFFKDLLGKFLGNN | 13 |
| PSMα4 WT | MAIVGTIIKIIKAIIDIFAK | 14 |
| PSMβ1 WT | MEGLFNAIKDTVTAAINNDGAKLGTS IVNIVENGVGLLSKLFGF | 15 |
| PSMβ2 WT | MTGLAEAIANTVQAAQQHDSVKLGTS IVDIVANGVGLLGKLFGF | 16 |
| PSM-mec | MDFTGVITSIIDLIKTCIQAFG | 52 |

In one aspect, the disclosure provides a recombinant peptide comprising a Staphylococcus delta toxin peptide or a mutant, fragment, variant or derivative thereof (DT); a Staphylococcus phenol soluble modulin peptide or a mutant, fragment, variant or derivative thereof (PSM); or a fusion of a DT and a PSM. A DT or PSM as provided herein can be mutated to reduce toxicity, e.g., surfactant properties, while retaining antigenicity. Accordingly, a recombinant DT, PSM, or both as provided by this disclosure can be attenuated relative to wild-type DT, PSM, or both, and yet the peptide can elicit an anti-*Staphylococcus aureus* immune response when administered to a subject. The antigenicity of DT and PSM can rely on maintenance of the peptide's alpha-helical structure, where the surfactant properties can rely on the toxin having a hydrophobic face. Thus in certain aspects, the disclosure provides a DT, a PSM or both, where hydrophobicity of the peptide is reduced relative to the wild-type peptide. For example, hydrophobicity can be reduced by replacing at least one, e.g., one, two, three, four, five or more hydrophobic amino acids which make up the hydrophobic face of the toxin with less hydrophobic amino acids. Hydrophobic amino acids include, but are not limited to valine (V), leucine (L), isoleucine (I), phenylalanine (F), and methionine (M). In certain aspects, a hydrophobic amino acid is replaced with a small amino acid that would not be expected to alter the alpha helical structure of the peptide. For example, the hydrophobic amino acid can be replaced with alanine (A) or glycine (G).

In one aspect, the disclosure provides a recombinant peptide comprising a mutated DT, where the DT comprises the amino acid sequence:

$$\text{MAQDX}_5\text{X}_6\text{STX}_9\text{GDX}_{12}\text{X}_{13}\text{KWX}_{16}\text{X}_{17}\text{DTX}_{20}\text{NKFTKK} \quad \text{(SEQ ID NO: 39)}$$

According to this aspect, at least one of $X_5$, $X_6$, $X_9$, $X_{12}$, $X_{13}$, $X_{16}$, $X_{17}$, or $X_{20}$ comprises an amino acid substitution relative to SEQ ID NO: 1. Thus, according to this aspect the DT is not wild-type DT. According to this aspect, $X_5$ can be isoleucine (I), glycine (G) or alanine (A), $X_6$ can be I, G, or A, $X_9$ can be I, G, or A, $X_{12}$ can be leucine (L), G, or V, $X_{13}$ can be valine (V), G, or A, $X_{16}$ can be I, G, or A, $X_{17}$ can be I, G, or A, and $X_{20}$ can be V, G, or A. In certain aspects, only a single amino acid from among $X_5$, $X_6$, $X_9$, $X_{12}$, $X_{13}$, $X_{16}$, $X_{17}$, or $X_{20}$ is substituted relative to SEQ ID NO: 1. Thus only one of $X_5$, $X_6$, $X_9$, $X_{12}$, $X_{13}$, $X_{16}$, $X_{17}$, or $X_{20}$ is G or A. In certain aspects $X_{12}$ is the single substituted amino acid. According to this aspect, $X_{12}$ can be G, and the peptide comprises the amino acid sequence SEQ ID NO: 2, or $X_{12}$ can be A and the peptide comprises the amino acid sequence SEQ ID NO: 4. In another aspect, two amino acids from among $X_5$, $X_6$, $X_9$, $X_{12}$, $X_{13}$, $X_{16}$, $X_{17}$, or $X_{20}$ are substituted relative to SEQ ID NO: 2. For example, $X_{12}$ and $X_{20}$ can be substituted, and can be G or A. Thus in certain aspects $X_{12}$ can independently be G or A, and $X_{20}$ can independently be G or A. For example, the DT can comprise the amino acid sequence SEQ ID NO: 3, or the amino acid sequence SEQ ID NO: 5. Other amino acid substitutions, either single, or multiple substitutions, can easily be visualized and constructed by a person of ordinary skill in the art according to this disclosure.

In another aspect, the disclosure provides a recombinant peptide comprising a mutated PSM, e.g., a mutant PSMα1, PSMα2, PSMα3, PSMα4, PSMβ1, PSMβ2, PSM-mec, or any combination of two or more PSMs.

In one aspect, the peptide comprises a mutant PSMα1 comprising the amino acid sequence:

$$X_1\text{GX}_3\text{X}_4\text{AGX}_7\text{X}_8\text{KX}_{10}\text{X}_{11}\text{KSX}_{14}\text{X}_{15}\text{EQX}_{18}\text{TGK} \quad \text{(SEQ ID NO: 40)}$$

According to this aspect, at least one of $X_1$, $X_3$, $X_4$, $X_7$, $X_8$, $X_{10}$, $X_{11}$, $X_{14}$, $X_{15}$, or $X_{18}$ comprises an amino acid substitution relative to SEQ ID NO: 38. Thus, according to this aspect the PSMα1 is not wild-type PSMα1 According to this aspect, $X_1$ can be methionine (M), G, or A, $X_3$ can be I, G, or A, $X_4$ can be I, G, or A, $X_7$ can be I, G, or A, $X_8$ can be I, G, or A, $X_{10}$ can be V, G, or A, $X_{11}$ can be I, G, or A, $X_{14}$ can be L, G, or A, $X_{15}$ can be I, G, or A, and $X_{18}$ can be F, G, or A. In certain aspects, only a single amino acid from among $X_1$, $X_3$, $X_4$, $X_7$, $X_8$, $X_{10}$, $X_{11}$, $X_{14}$, $X_{15}$, and $X_{18}$ is substituted relative to SEQ ID NO: 38. Thus only one of $X_1$, $X_3$, $X_4$, $X_7$, $X_8$, $X_{10}$, $X_{11}$, $X_{14}$, $X_{15}$, and $X_{18}$ is G or A. In another aspect, two amino acids from among $X_1$, $X_3$, $X_4$, $X_7$, $X_8$, $X_{10}$, $X_{11}$, $X_{14}$, $X_{15}$, and $X_{18}$ are substituted relative to SEQ ID NO: 38. Various amino acid substitutions in PSMal, either single, or multiple substitutions, can easily be visualized and constructed by a person of ordinary skill in the art according to this disclosure.

In one aspect, the peptide comprises a mutant PSMα2 comprising the amino acid sequence:

$$X_1\text{GX}_3\text{X}_4\text{AGX}_7\text{X}_8\text{KX}_{10}\text{X}_{11}\text{KGX}_{14}\text{X}_{15}\text{EKX}_{18}\text{TGK} \quad \text{(SEQ ID NO: 41)}$$

According to this aspect, at least one of $X_1$, $X_3$, $X_4$, $X_7$, $X_8$, $X_{10}$, $X_{11}$, $X_{14}$, $X_{15}$, or $X_{18}$ comprises an amino acid substitution relative to SEQ ID NO: 12. Thus, according to this aspect the PSMα2 is not wild-type PSMα2. According to this aspect, $X_1$ can be M, G, or A, $X_3$ can be I, G, or A, $X_4$ can be I, G, or A, $X_7$ can be I, G, or A, $X_8$ can be I, G, or A, $X_{10}$ can be F, G, or A, $X_{11}$ can be I, G, or A, $X_{14}$ can be L, G, or A, $X_{15}$ can be I, G, or A, and $X_{18}$ can be F, G, or A. In certain aspects, only a single amino acid from among $X_1$, $X_3$, $X_4$, $X_7$, $X_8$, $X_{10}$, $X_{11}$, $X_{14}$, $X_{15}$, and $X_{18}$ is substituted relative to SEQ ID NO: 12. Thus only one of $X_1$, $X_3$, $X_4$, $X_7$, $X_8$, $X_{10}$, $X_{11}$, $X_{14}$, $X_{15}$, and $X_{18}$ is G or A. In another aspect, two amino acids from among $X_1$, $X_3$, $X_4$, $X_7$, $X_8$, $X_{10}$, $X_{11}$, $X_{14}$, $X_{15}$, and $X_{18}$ are substituted relative to SEQ ID NO: 12. Various amino acid substitutions, either single, or multiple substitutions, can easily be visualized and constructed by a person of ordinary skill in the art according to this disclosure.

In one aspect, the peptide comprises a mutant PSMα3 comprising the amino acid sequence:

$$X_1\text{EX}_3\text{X}_4\text{AKX}_7\text{X}_8\text{KX}_{10}\text{X}_{11}\text{KDX}_{14}\text{X}_{15}\text{GKX}_{18}\text{X}_{19}\text{GNN} \quad \text{(SEQ ID NO: 42)}$$

According to this aspect, at least one of $X_1$, $X_3$, $X_1$, $X_7$, $X_8$, $X_{10}$, $X_{11}$, $X_{14}$, $X_{15}$, $X_{18}$, or $X_{19}$ comprises an amino acid substitution relative to SEQ ID NO: 6. Thus, according to this aspect the PSMα3 is not wild-type PSMα3. According to this aspect, $X_1$ can be M, G, or A, $X_3$ can be F, G, or A, $X_4$ can be V, G, or A, $X_7$ can be L, G, or A, $X_8$ can be F, G, or A, $X_{10}$ can be F, G, or A, $X_{11}$ can be F, G, or A, $X_{14}$ can be L, G, or A, $X_{15}$ can be L, G, or A, $X_{18}$ can be F, G, or A, and $X_{19}$ can be L, G, or A. In certain aspects, only a single amino acid from among $X_1$, $X_3$, $X_4$, $X_7$, $X_8$, $X_{10}$, $X_{11}$, $X_{14}$, $X_{15}$, $X_{18}$, and $X_{19}$ is substituted relative to SEQ ID NO: 6. Thus only one, of $X_1$, $X_3$, $X_4$, $X_7$, $X_8$, $X_{10}$, $X_{11}$, $X_{14}$, $X_{15}$, $X_{18}$, and $X_{19}$ is G or A. In certain aspects $X_{14}$ is the single substituted amino acid. According to this aspect, $X_{14}$ can be G, and the peptide comprises the amino acid sequence SEQ ID NO: 9, or $X_{14}$ can be A and the peptide comprises the amino acid sequence SEQ ID NO: 7. In another aspect, two amino acids from among $X_1$, $X_3$, $X_4$, $X_7$, $X_8$, $X_{10}$, $X_{11}$, $X_{14}$, $X_{15}$, $X_{18}$, and $X_{19}$ are substituted relative to SEQ ID NO: 6. For example, $X_4$ and $X_{14}$ can be substituted, and can be G or A. Thus in certain aspects $X_4$ can independently be G or A, and $X_{14}$ can independently be G or A. For example, the PSMα3 can comprise the amino acid sequence SEQ ID NO: 8, the amino acid sequence SEQ ID NO: 10, or the amino acid sequence SEQ ID NO: 11. Other amino acid substitutions, either single, or multiple substitutions, can easily be visualized and constructed by a person of ordinary skill in the art according to this disclosure.

In one aspect, the peptide comprises a mutant PSMα4 comprising the amino acid sequence:

$$\text{(SEQ ID NO: 43)}$$
$$X_1AX_3X_4GTX_7X_8KX_{10}X_{11}KAX_{14}X_{15}DX_{17}X_{18}AK$$

According to this aspect, at least one of $X_1$, $X_3$, $X_4$, $X_7$, $X_8$, $X_{10}$, $X_{11}$, $X_{14}$, $X_{15}$, $X_{17}$, or $X_{18}$ comprises an amino acid substitution relative to SEQ ID NO: 14. Thus, according to this aspect the PSMα4 is not wild-type PSMα4. According to this aspect, $X_1$ can be M, G, or A, $X_3$ can be I, G, or A, $X_4$ can be V, G, or A, $X_7$ can be I, G, or A, $X_8$ can be I, G, or A, $X_{10}$ can be I, G, or A, $X_{11}$ can be I, G, or A, $X_{14}$ can be I, G, or A, $X_{15}$ can be I, G, or A, $X_{17}$ can be I, G, or A, and $X_{18}$ can be F, G, or A. In certain aspects, only a single amino acid from among $X_1$, $X_3$, $X_4$, $X_7$, $X_8$, $X_{10}$, $X_{11}$, $X_{14}$, $X_{15}$, $X_{17}$, and $X_{18}$ is substituted relative to SEQ ID NO: 14. Thus only one of $X_1$, $X_3$, $X_4$, $X_7$, $X_8$, $X_{10}$, $X_{11}$, $X_{14}$, $X_{15}$, $X_{17}$, and $X_{18}$ is G or A. In another aspect, two amino acids from among $X_1$, $X_3$, $X_4$, $X_7$, $X_8$, $X_{10}$, $X_{11}$, $X_{14}$, $X_{15}$, $X_{17}$, and $X_{18}$ are substituted relative to SEQ ID NO: 14. Other amino acid substitutions, either single, or multiple substitutions, can easily be visualized and constructed by a person of ordinary skill in the art according to this disclosure.

In one aspect, the peptide comprises a mutant PSMβ1 comprising the amino acid sequence:

$$\text{(SEQ ID NO: 44)}$$
$$MEGX_4X_5NAX_8KDTX_{12}TAAX_{16}NNDGAKLGTSIVNIVENGVGLLSKLFGF$$

According to this aspect, at least one of $X_4$, $X_5$, $X_8$, $X_{12}$, or $X_{16}$ comprises an amino acid substitution relative to SEQ ID NO: 15. Thus, according to this aspect the PSMβ1 is not wild-type PSMβ1. According to this aspect, $X_4$ can be L, G, or A, $X_5$ can be F, G, or A, $X_8$ can be I, G, or A, $X_{12}$ can be V, G, or A, and $X_{16}$ can be I, G, or A. In certain aspects, only a single amino acid from among $X_4$, $X_5$, $X_8$, $X_{12}$, and $X_{16}$ is substituted relative to SEQ ID NO: 15. Thus only one of $X_4$, $X_5$, $X_8$, $X_{12}$, and $X_{16}$ is G or A. In another aspect, two amino acids from among $X_4$, $X_5$, $X_8$, $X_{12}$, and $X_{16}$ are substituted relative to SEQ ID NO: 15. Other amino acid substitutions, either single, or multiple substitutions, can easily be visualized and constructed by a person of ordinary skill in the art according to this disclosure.

In one aspect, the peptide comprises a mutant PSMβ2 comprising the amino acid sequence:

$$\text{(SEQ ID NO: 45)}$$
$$MTGX_4AEAX_8ANTX_{12}QAAQQHDSVKX_{23}GTSIVDIVANGVGLLGKLFGF$$

According to this aspect, at least one of $X_4$, $X_8$, $X_{12}$, or $X_{23}$ comprises an amino acid substitution relative to SEQ ID NO: 16. Thus, according to this aspect the PSMβ2 is not wild-type PSMβ2. According to this aspect, $X_4$ can be L, G, or A, $X_8$ can be I, G, or A, $X_{12}$ can be V, G, or A, and $X_{23}$ can be L, G, or A. In certain aspects, only a single amino acid from among $X_4$, $X_8$, $X_{12}$, and $X_{23}$ is substituted relative to SEQ ID NO: 16. Thus only one of $X_4$, $X_8$, $X_{12}$, and $X_{23}$ is G or A. In another aspect, two amino acids from among $X_4$, $X_8$, $X_{12}$, and $X_{23}$ are substituted relative to SEQ ID NO: 16. Other amino acid substitutions, either single, or multiple substitutions, can easily be visualized and constructed by a person of ordinary skill in the art according to this disclosure.

In one aspect, the peptide comprises a mutant PSM-mec comprising the amino acid sequence:

$$\text{(SEQ ID NO: 53)}$$
$$MDX_3TGX_6X_7TSX_{10}X_{11}DX_{13}X_{14}KTX_{17}X_{18}QAFG$$

According to this aspect, at least one of $X_3$, $X_6$, $X_7$, $X_{10}$, $X_{11}$, $X_{13}$, $X_{14}$, $X_{17}$, or $X_{18}$ comprises an amino acid substitution relative to SEQ ID NO: 52. Thus, according to this aspect the PSM-mec is not wild-type PSM-mec. According to this aspect, $X_3$ can be F, G, or A, $X_6$ can be V, G, or A, $X_7$ can be I, G, or A, $X_{10}$ can be I, G, or A, $X_{11}$ can be I, G, or A, $X_{13}$ can be L, G, or A, $X_{14}$ can be I, G, or A, $X_{17}$ can be C, G, or A, and $X_{18}$ can be I, G, or A. In certain aspects, only a single amino acid from among $X_3$, $X_6$, $X_7$, $X_{10}$, $X_{11}$, $X_{13}$, $X_{14}$, $X_{17}$, or $X_{18}$ is substituted relative to SEQ ID NO: 52. Thus only one of $X_3$, $X_6$, $X_7$, $X_{10}$, $X_{11}$, $X_{13}$, $X_{14}$, $X_{17}$, or $X_{18}$ is G or A. In another aspect, two amino acids from among $X_1$, $X_3$, $X_4$, $X_7$, $X_8$, $X_{10}$, $X_{11}$, $X_{14}$, $X_{15}$, and $X_{18}$ are substituted relative to SEQ ID NO: 52. Various amino acid substitutions in PSM-mec, either single, or multiple substitutions, can easily be visualized and constructed by a person of ordinary skill in the art according to this disclosure.

The disclosure further provides a multivalent oligopeptide comprising a fusion of two or more, e.g., two, three, four, five, six, seven, eight, nine, ten or more *Staphylococcus aureus*-derived peptides, or mutants, fragments, variants, or derivatives thereof arranged in any order. The two or more *Staphylococcus aureus*-derived peptides, or mutants, fragments, variants, or derivatives thereof can be the same or different. A multivalent oligopeptide as provided herein can include, without limitation, two or more of:

a. a wild-type DT, a mutant DT as described above, or any fragment, variant, or derivative thereof;

b. a wild-type PSM, a mutant PSM as described above, or any fragment, variant, or derivative thereof;

c. an alpha hemolysin polypeptide or mutant, fragment, variant, or derivative thereof, including without limitation AT-62 (SEQ ID NO: 46), or other alpha hemolysin peptides as described elsewhere herein and in PCT Publication No. WO 2012/109167A1;

d. a leukocidin polypeptide or mutant, fragment, variant, or derivative thereof, including, without limitation, a Panton-Valentine leukocidin (PVL) LukS-PV subunit comprising an amino acid sequence at least 75%, 80%, 85%, 90%, 95%, 96%, 97%, 98%, or 99% identical to SEQ ID NO: 47, a Panton-Valentine leukocidin (PVL) LukF-PV subunit comprising an amino acid sequence at least 75%, 80%, 85%, 90%, 95%, 96%, 97%, 98%, or 99% identical to SEQ ID NO: 48, or a combination thereof; or other leukocidin peptides as described elsewhere herein and in PCT Publication No. WO 2013/082558, including, without limitation, LukS-Mut9 (SEQ ID NO: 54) and/or LukF-Mut-1 (SEQ ID NO: 55); or e. a superantigen (SAg) polypeptide, or mutant, fragment, variant, or derivative thereof.

In some embodiments, the peptides comprising the multivalent oligopeptide can be directly fused to each other. In other embodiments, the peptides comprising the multivalent oligopeptide can be associated via a peptide linker. Suitable peptide linkers can be chosen based on their ability to adopt a flexible, extended conformation, or a secondary structure that can interact with joined epitopes, or based on their ability to increase overall solubility of the fusion polypeptide, or based on their lack of electrostatic or water-interaction effects that influence joined peptide regions. In certain aspects, a linker for use in a multivalent oligopeptide as provided herein can include at least one, but no more than 50 amino acids, e.g., small amino acids that provide a flexible chain, e.g., glycine, serine, alanine, or a combination thereof. In certain aspects, a linker for use in a multivalent oligopeptide as provided herein can include $(GGGS)_n$ or $(GGGGS)_n$, wherein n is a integer from 1 to 10.

In certain aspects, the multivalent oligopeptide includes AT-62 and DT, in any order, where AT-62 and DT can be fused together via a linker sequence. In certain aspects, the multivalent oligopeptide comprises, consists of, or consists essentially of AT62_DT (SEQ ID NO: 18), or an oligopeptide comprising, consisting, or consisting essentially of an amino acid sequence at least 75%, 80%, 85%, 90%, 95%, 96%, 97%, 98%, or 99% identical to SEQ ID NO: 18.

In certain aspects, the multivalent oligopeptide includes AT-62 and a PSM, in any order, where AT-62 and PSM can be fused together via a linker sequence. In certain aspects, the multivalent oligopeptide comprises, consists of, or consists essentially of AT62_PSM (SEQ ID NO: 20), or an oligopeptide comprising, consisting, or consisting essentially of an amino acid sequence at least 75%, 80%, 85%, 90%, 95%, 96%, 97%, 98%, or 99% identical to SEQ ID NO: 20.

In certain aspects, the multivalent oligopeptide includes AT-62, DT, and a PSM, in any order, where AT-62, DT, and PSM can be fused together via linker sequences. In certain aspects, the multivalent oligopeptide comprises, consists of, or consists essentially of AT62_DT_PSM (SEQ ID NO: 22), or an oligopeptide comprising, consisting, or consisting essentially of an amino acid sequence at least 75%, 80%, 85%, 90%, 95%, 96%, 97%, 98%, or 99% identical to SEQ ID NO: 22.

In certain aspects, the multivalent oligopeptide includes AT-62 and a recombinant SEB or mutant, fragment, variant, or derivative thereof, in any order, where AT-62 and SEB can be fused together via a linker sequence. In certain aspects, the multivalent oligopeptide comprises, consists of, or consists essentially of AT62_rSEB (SEQ ID NO: 23), or an oligopeptide comprising, consisting, or consisting essentially of an amino acid sequence at least 75%, 80%, 85%, 90%, 95%, 96%, 97%, 98%, or 99% identical to SEQ ID NO: 23. In certain aspects, the multivalent oligopeptide comprises, consists of, or consists essentially of rSEB_AT62 (SEQ ID NO: 26), or an oligopeptide comprising, consisting, or consisting essentially of an amino acid sequence at least 75%, 80%, 85%, 90%, 95%, 96%, 97%, 98%, or 99% identical to SEQ ID NO: 26.

In certain aspects, the multivalent oligopeptide includes AT-62, a recombinant SEB or mutant, fragment, variant, or derivative thereof, and DT, in any order, where AT-62, SEB, and DT can be fused together via a linker sequence. In certain aspects, the multivalent oligopeptide comprises, consists of, or consists essentially of AT62_rSEB_DT (SEQ ID NO: 29), or an oligopeptide comprising, consisting, or consisting essentially of an amino acid sequence at least 75%, 80%, 85%, 90%, 95%, 96%, 97%, 98%, or 99% identical to SEQ ID NO: 29.

Where the provided oligopeptide includes a staphylococcal SAg or mutant, fragment, variant, or derivative thereof, the SAg, can include, without limitation, SEB, SEC1-3, SEE, SEH, SEI, SEK, TSST-1, SpeC, SED, SpeA, or any mutant, fragment, variant, or derivative thereof, or any combination thereof, in any order. In certain aspects, the oligopeptide includes a staphylococcal enterotoxin B (SEB) or mutant, fragment, variant, or derivative thereof. In certain aspects, the SEB mutant is the attenuated toxoid $SEB_{L45R/Y89A/Y94A}$ (SEQ ID NO: 49), or a polypeptide comprising an amino acid sequence at least 75%, 80%, 85%, 90%, 95%, 96%, 97%, 98%, or 99% identical to SEQ ID NO: 49. In certain aspects, the oligopeptide includes a staphylococcal enterotoxin A (SEA) or mutant, fragment, variant, or derivative thereof. In certain aspects, the SEA mutant is the attenuated toxoid $SEA_{L48R/D70R/Y92A}$ (SEQ ID NO: 50), or a polypeptide comprising an amino acid sequence at least 75%, 80%, 85%, 90%, 95%, 96%, 97%, 98%, or 99% identical to SEQ ID NO: 50. In certain aspects, the oligopeptide includes a staphylococcal toxic shock syndrome toxin-1 (TSST-1) or mutant, fragment, variant, or derivative thereof. In certain aspects, the TSST-1 mutant is the attenuated toxoid $TSST-1_{L30R/D27A/I46A}$ (SEQ ID NO: 51), or a polypeptide comprising an amino acid sequence at least 75%, 80%, 85%, 90%, 95%, 96%, 97%, 98%, or 99% identical to SEQ ID NO: 51.

The SAg toxoids can be linked together in any order, either with our without linkers. In certain aspects, the multivalent oligopeptide includes $SEB_{L45R/Y89A/Y94A}$ ("B"), $SEA_{L48R/D70R/Y92A}$ ("A"), and $TSST-1_{L30R/D27A/I46A}$ ("T"), in any order, where the toxoids can be fused together via linker sequences. In certain aspects, the multivalent oligopeptide comprises, consists of, or consists essentially of a "BAT" fusion (SEQ ID NO: 32), or an oligopeptide comprising, consisting, or consisting essentially of an amino acid sequence at least 75%, 80%, 85%, 90%, 95%, 96%, 97%, 98%, or 99% identical to SEQ ID NO: 32. In certain aspects, the multivalent oligopeptide comprises, consists of, or consists essentially of a "BTA" fusion (SEQ ID NO: 33), or an oligopeptide comprising, consisting, or consisting essentially of an amino acid sequence at least 75%, 80%, 85%, 90%, 95%, 96%, 97%, 98%, or 99% identical to SEQ ID NO: 33. In certain aspects, the multivalent oligopeptide comprises, consists of, or consists essentially of a "ABT" fusion (SEQ ID NO: 34), or an oligopeptide comprising, consisting, or consisting essentially of an amino acid sequence at least 75%, 80%, 85%, 90%, 95%, 96%, 97%, 98%, or 99% identical to SEQ ID NO: 34. In certain aspects, the multivalent oligopeptide comprises, consists of, or consists essentially of a "ATB" fusion (SEQ ID NO: 35), or an oligopeptide comprising, consisting, or consisting essentially of an amino acid sequence at least 75%, 80%, 85%, 90%, 95%, 96%, 97%, 98%, or 99% identical to SEQ ID NO: 35. In certain aspects, the multivalent oligopeptide comprises, consists of, or consists essentially of a "TAB" fusion (SEQ ID NO: 36), or an oligopeptide comprising, consisting, or consisting essentially of an amino acid sequence at least 75%, 80%, 85%, 90%, 95%, 96%, 97%, 98%, or 99% identical to SEQ ID NO: 36. In certain aspects, the multivalent oligopeptide comprises, consists of, or consists essentially of a "TBA" fusion (SEQ ID NO: 37), or an oligopeptide comprising, consisting, or consisting essentially of an amino acid sequence at least 75%, 80%, 85%, 90%, 95%, 96%, 97%, 98%, or 99% identical to SEQ ID NO: 37.

In certain aspects the multivalent oligopeptide comprises, consists of, or consists essentially of the amino acid sequence SEQ ID NO: 18, SEQ ID NO: 20, SEQ ID NO: 22, SEQ ID NO: 23, SEQ ID NO: 26, SEQ ID NO: 29, SEQ ID NO: 32, SEQ ID NO: 33, SEQ ID NO. 34, SEQ ID NO: 35, SEQ ID NO: 36, SEQ ID NO: 37, or any combination thereof.

In another embodiment, the multivalent oligopeptide, DT, and/or PSM as described herein, can be attached to a heterologous polypeptide. Various heterologous polypeptides can be used, including, but not limited to an N- or C-terminal peptide imparting stabilization, secretion, or simplified purification, such as a hexa-Histidine-tag, a ubiquitin tag, a NusA tag, a chitin binding domain, ompT, ompA, pelB, DsbA, DsbC, c-myc, KSI, polyaspartic acid, (Ala-Trp-Trp-Pro)n, polyphenyalanine, polycysteine, polyarginine, a B-tag, a HSB-tag, green fluorescent protein (GFP), influenza virus hemagglutinin (HAI), a calmodulin binding protein (CBP), a galactose-binding protein, a maltose binding protein (MBP), a cellulose binding domains (CBD's), dihydrofolate reductase (DHFR), glutathione-S-transferase (GST), streptococcal protein G, staphylococcal protein A, T7gene10, an avidin/streptavidin/Strep-tag complex, trpE, chloramphenicol acetyltransferase, lacZ (β-Galactosidase), His-patch thioredoxin, thioredoxin, a FLAG™ peptide (Sigma-Aldrich), an S-tag, or a T7-tag. See, e.g., Stevens, R. C., Structure, 8:R177-R185 (2000). Heterologous polypeptides can also include any pre- and/or pro-sequences that facilitate the transport, translocations, processing and/or purification of a multivalent oligopeptide, DT, and/or PSM as described herein from a host cell or any useful immunogenic sequence, including but not limited to sequences that encode a T-cell epitope of a microbial pathogen, or other immunogenic proteins and/or epitopes.

In some embodiments, the multivalent oligopeptide, DT, and/or PSM attached to a heterologous polypeptide, as described herein, can include a peptide linker sequence joining sequences that comprise two or more peptide regions. Suitable peptide linker sequences can be chosen based on their ability to adopt a flexible, extended conformation, or a secondary structure that could interact with joined epitopes, or based on their ability to increase overall solubility of the fusion polypeptide, or based on their lack of electrostatic or water-interaction effects that influence joined peptide regions.

In some embodiments, the multivalent oligopeptide, DT, and/or PSM as described herein, is isolated. An "isolated" polypeptide is one that has been removed from its natural milieu. The term "isolated" does not connote any particular level of purification. Recombinantly produced multivalent oligopeptides, DTs, and/or PSMs as described herein, expressed in non-native host cells is considered isolated for purposes of the disclosure, as is the polypeptide which have been separated, fractionated, or partially or substantially purified by any suitable technique, including by filtration, chromatography, centrifugation, and the like.

Production of multivalent oligopeptides, DTs, and/or PSMs as described herein, can be achieved by culturing a host cell comprising a polynucleotide which operably encodes the polypeptide of the disclosure, and recovering the polypeptide. Determining conditions for culturing such a host cell and expressing the polynucleotide are generally specific to the host cell and the expression system and are within the knowledge of one of skill in the art. Likewise, appropriate methods for recovering the polypeptide of the disclosure are known to those in the art, and include, but are not limited to, chromatography, filtration, precipitation, or centrifugation.

III. Polynucleotides

Also disclosed is an isolated polynucleotide comprising a nucleic acid encoding a multivalent oligopeptide, DT, and/or PSM as described elsewhere herein.

In certain embodiments, the isolated polynucleotide as described herein further comprises non-coding regions such as promoters, operators, or transcription terminators as described elsewhere herein. In some embodiments, the disclosure is directed to the polynucleotide as described herein, and further comprising a heterologous nucleic acid. The heterologous nucleic acid can, in some embodiments, encode a heterologous polypeptide fused to the polypeptide as described herein. For example, the isolated polynucleotide as described herein can comprise additional coding regions encoding, e.g., a heterologous polypeptide fused to the polypeptide as described herein, or coding regions encoding heterologous polypeptides separate from the polypeptide as described herein such as, but not limited to, selectable markers, additional immunogens, immune enhancers, and the like.

Also provided are expression constructs, vectors, and/or host cells comprising the polynucleotides described herein. An example of an isolated polynucleotide is a recombinant polynucleotide contained in a vector. Further examples of an isolated polynucleotide include recombinant polynucleotides maintained in heterologous host cells or purified (partially or substantially) polynucleotides in solution. In certain embodiments of the disclosure a polynucleotide is "recombinant." Isolated polynucleotides or nucleic acids according to the disclosure further include such molecules produced synthetically. The relative degree of purity of a polynucleotide or polypeptide described herein is easily determined by well-known methods.

Also included within the scope of the disclosure are genetically engineered polynucleotides encoding the multivalent oligopeptides, DTs, and/or PSMs as described herein. Modifications of nucleic acids encoding the multivalent oligopeptides, DTs, and/or PSMs as described herein, can readily be accomplished by those skilled in the art, for example, by oligonucleotide-directed site-specific mutagenesis or de novo nucleic acid synthesis.

Some embodiments disclose an isolated polynucleotide comprising a nucleic acid that encodes a multivalent oligopeptide, DT, and/or PSM as described herein, where the coding region encoding the polypeptide has been codon-optimized. As appreciated by one of ordinary skill in the art, various nucleic acid coding regions will encode the same polypeptide due to the redundancy of the genetic code. Deviations in the nucleotide sequence that comprise the codons encoding the amino acids of any polypeptide chain allow for variations in the sequence of the coding region. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 2. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the polypeptides encoded by the DNA.

TABLE 2

The Standard Genetic Code

| | T | | C | | A | | G | |
|---|---|---|---|---|---|---|---|---|
| T | TTT | Phe (F) | TCT | Ser (S) | TAT | Tyr (Y) | TGT | Cys (C) |
| | TTC | " | TCC | " | TAC | " | TGC | " |
| | TTA | Leu (L) | TCA | " | TAA | Ter | TGA | Ter |
| | TTG | " | TCG | " | TAG | Ter | TGG | Trp (W) |
| C | CTT | Leu (L) | CCT | Pro (P) | CAT | His (H) | CGT | Arg (R) |
| | CTC | " | CCC | " | CAC | " | CGC | " |
| | CTA | " | CCA | " | CAA | Gln (Q) | CGA | " |
| | CTG | " | CCG | " | CAG | " | CGG | " |
| A | ATT | Ile (I) | ACT | Thr (T) | AAT | Asn (N) | AGT | Ser (S) |
| | ATC | " | ACC | " | AAC | " | AGC | " |
| | ATA | " | ACA | " | AAA | Lys (K) | AGA | Arg (R) |
| | ATG | Met (M) | ACG | " | AAG | " | AGG | " |
| G | GTT | Val (V) | GCT | Ala (A) | GAT | Asp (D) | GGT | Gly (G) |
| | GTC | " | GCC | " | GAC | " | GGC | " |
| | GTA | " | GCA | " | GAA | Glu (E) | GGA | " |
| | GTG | " | GCG | " | GAG | " | GGG | " |

It is to be appreciated that any polynucleotide that encodes a polypeptide in accordance with the disclosure falls within the scope of this disclosure, regardless of the codons used.

Many organisms display a bias for use of particular codons to code for insertion of a particular amino acid in a growing polypeptide chain. Codon preference or codon bias, differences in codon usage between organisms, is afforded by degeneracy of the genetic code, and is well documented among many organisms.

Different factors have been proposed to contribute to codon usage preference, including translational selection, GC composition, strand-specific mutational bias, amino acid conservation, protein hydropathy, transcriptional selection and even RNA stability. One factor that determines codon usage is mutational bias that shapes genome GC composition. This factor is most significant in genomes with extreme base composition: species with high GC content (e.g., gram positive bacteria). Mutational bias is responsible not only for intergenetic difference in codon usage but also for codon usage bias within the same genome (Ermolaeva M, *Curr. Issues Mol. Biol.* 3 (4):91-97, 2001).

Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

The present disclosure provides a polynucleotide comprising a codon-optimized coding region which encodes a multivalent oligopeptide, DT, and/or PSM as described herein. The codon usage is adapted for optimized expression in a given prokaryotic or eukaryotic host cell. In certain aspects the codon usage is adapted for optimized expression in *E. coli*.

In certain aspects an isolated polynucleotide is provided comprising the nucleic acid sequence SEQ ID NO: 17, encoding AT62_DT and optimized for expression in *E. coli*. In certain aspects an isolated polynucleotide is provided comprising the nucleic acid sequence SEQ ID NO: 19, encoding AT62_PSM and optimized for expression in *E. coli*. In certain aspects an isolated polynucleotide is provided comprising the nucleic acid sequence SEQ ID NO: 21, encoding AT62_DT_PSM and optimized for expression in *E. coli*. In certain aspects an isolated polynucleotide is provided comprising the nucleic acid sequence SEQ ID NO: 25, encoding AT62_rSEB and optimized for expression in *E. coli*. In certain aspects an isolated polynucleotide is provided comprising the nucleic acid sequence SEQ ID NO: 28, encoding rSEB_AT62 and optimized for expression in *E. coli*. In certain aspects an isolated polynucleotide is provided comprising the nucleic acid sequence SEQ ID NO: 31, encoding AT62_rSEB_DT and optimized for expression in *E. coli*.

Codon-optimized polynucleotides are prepared by incorporating codons preferred for use in the genes of a given species into the DNA sequence. Also provided are polynucleotide expression constructs, vectors, host cells comprising polynucleotides comprising codon-optimized coding regions which encode a multivalent oligopeptide, DT, and/or PSM as described herein.

Given the large number of gene sequences available for a wide variety of animal, plant and microbial species, it is possible to calculate the relative frequencies of codon usage. Codon usage tables are readily available, for example, at the "Codon Usage Database" available at http://www.kazusa.or.jp/codon/ (visited Oct. 12, 2011), and these tables can be adapted in a number of ways. (Nakamura, Y., et al., "Codon usage tabulated from the international DNA sequence databases: status for the year 2000*" Nucl. Acids Res.* 28:292, 2000).

By utilizing available tables, one of ordinary skill in the art can apply the frequencies to any given polypeptide sequence, and produce a nucleic acid fragment of a codon-optimized coding region which encodes a desired polypeptide, but which uses codons optimal for a given species. For example, in some embodiments of the disclosure, the coding region is codon-optimized for expression in *E. coli.*

A number of options are available for synthesizing codon optimized coding regions designed by any of the methods described above, using standard and routine molecular biological manipulations well known to those of ordinary skill in the art. In addition, gene synthesis is readily available commercially.

IV. Vectors and Expression Systems

Further disclosed is a vector comprising the polynucleotide as described herein. The term "vector," as used herein, refers to e.g., any of a number of nucleic acids into which a desired sequence can be inserted, e.g., by restriction and ligation, for transport between different genetic environments or for expression in a host cell. Nucleic acid vectors can be DNA or RNA. Vectors include, but are not limited to, plasmids, phage, phagemids, bacterial genomes, and virus genomes. A cloning vector is one which is able to replicate in a host cell, and which is further characterized by one or more endonuclease restriction sites at which the vector can be cut in a determinable fashion and into which a desired DNA sequence can be ligated such that the new recombinant vector retains its ability to replicate in the host cell. In the case of plasmids, replication of the desired sequence can occur many times as the plasmid increases in copy number within the host bacterium or just a single time per host before the host reproduces by mitosis. In the case of phage, replication can occur actively during a lytic phase or passively during a lysogenic phase. Certain vectors are capable of autonomous replication in a host cell into which they are introduced. Other vectors are integrated into the genome of a host cell upon introduction into the host cell, and thereby are replicated along with the host genome.

Any of a wide variety of suitable cloning vectors are known in the art and commercially available which can be used with appropriate hosts. As used herein, the term "plasmid" refers to a circular, double-stranded construct made up of genetic material (i.e., nucleic acids), in which the genetic material is extrachromosomal and in some instances, replicates autonomously. A polynucleotide described herein can be in a circular or linearized plasmid or in any other sort of vector. Procedures for inserting a nucleotide sequence into a vector, e.g., an expression vector, and transforming or transfecting into an appropriate host cell and cultivating under conditions suitable for expression are generally known in the art.

The disclosure further provides a vector comprising a nucleic acid sequence encoding a multivalent oligopeptide, DT, and/or PSM as described herein. In certain embodiments the vector is an expression vector capable of expressing the multivalent oligopeptide, DT, and/or PSM as described herein in a suitable host cell. The term "expression vector" refers to a vector that is capable of expressing the polypeptide described herein, i.e., the vector sequence contains the regulatory sequences required for transcription and translation of a polypeptide, including, but not limited to promoters, operators, transcription termination sites, ribosome binding sites, and the like. The term "expression" refers to the biological production of a product encoded by a coding sequence. In most cases a DNA sequence, including the coding sequence, is transcribed to form a messenger-RNA (mRNA). The messenger-RNA is then translated to form a polypeptide product which has a relevant biological activity. Also, the process of expression can involve further processing steps to the RNA product of transcription, such as splicing to remove introns, and/or post-translational processing of a polypeptide product.

Vector-host systems include, but are not limited to, systems such as bacterial, mammalian, yeast, insect or plant cell systems, either in vivo, e.g., in an animal or in vitro, e.g., in bacteria or in cell cultures. The selection of an appropriate host is deemed to be within the scope of those skilled in the art from the teachings herein. In certain embodiments, the host cell is a bacterium, e.g., *E. coli*.

Host cells are genetically engineered (infected, transduced, transformed, or transfected) with vectors of the disclosure. Thus, one aspect of the disclosure is directed to a host cell comprising a vector which contains the polynucleotide as describe herein. The engineered host cell can be cultured in conventional nutrient media modified as appropriate for activating promoters, selecting transformants or amplifying the polynucleotides. The culture conditions, such as temperature, pH and the like, are those previously used with the host cell selected for expression, and will be apparent to the ordinarily skilled artisan. The term "transfect," as used herein, refers to any procedure whereby eukaryotic cells are induced to accept and incorporate into their genome isolated DNA, including but not limited to DNA in the form of a plasmid. The term "transform," as used herein, refers to any procedure whereby bacterial cells are induced to accept and incorporate into their genome isolated DNA, including but not limited to DNA in the form of a plasmid.

Bacterial host-expression vector systems include, but are not limited to, a prokaryote (e.g., *E. coli*), transformed with recombinant bacteriophage DNA, plasmid DNA or cosmid DNA. In some embodiments, the plasmids used with *E. coli* use the T7 promoter-driven system regulated by the LacI protein via IPTG induction. A large number of suitable vectors are known to those of skill in the art, and are commercially available. The following bacterial vectors are provided by way of example: pET (Novagen), pET28, pBAD, pTrcHIS, pBR322, pQE70, pQE60, pQE-9 (Qiagen), phagescript, psiX174, pBluescript SK, pbsks, pNH8A, pNH16a, pNH18A, pNH46A (Stratagene), ptrc99a, pKK223-3, pKK243-3, pDR540, pBR322, pPS10, RSF1010, pRIT5 (Pharmacia); pCR (Invitrogen); pLex (Invitrogen), and pUC plasmid derivatives.

A suitable expression vector contains regulatory sequences that can be operably joined to an inserted nucleotide sequence encoding the multivalent oligopeptide, DT, and/or PSM as described herein. As used herein, the term "regulatory sequences" means nucleotide sequences which are necessary for or conducive to the transcription of an inserted sequence encoding a multivalent oligopeptide, DT, and/or PSM as described herein by a host cell and/or which are necessary for or conducive to the translation by a host cell of the resulting transcript into the desired multivalent oligopeptide, DT, and/or PSM. Regulatory sequences include, but are not limited to, 5' sequences such as operators, promoters and ribosome binding sequences, and 3' sequences such as polyadenylation signals or transcription terminators. Regulatory sequences can also include enhancer sequences or upstream activator sequences.

Generally, bacterial vectors will include origins of replication and selectable markers, e.g., the ampicillin, tetracycline, kanamycin, resistance genes of *E. coli*, permitting transformation of the host cell and a promoter derived from a highly-expressed gene to direct transcription of a downstream structural sequence. Suitable promoters include, but are not limited to, the T7 promoter, lambda (λ) promoter, T5 promoter, and lac promoter, or promoters derived from operons encoding glycolytic enzymes such as 3-phosphoglycerate kinase (PGK), acid phosphatase, or heat shock proteins, or inducible promoters like cadmium (pcad), and beta-lactamase (pbla).

Once an expression vector is selected, the polynucleotide as described herein can be cloned downstream of the promoter, for example, in a polylinker region. The vector is transformed into an appropriate bacterial strain, and DNA is prepared using standard techniques. The orientation and DNA sequence of the polynucleotide as well as all other elements included in the vector, are confirmed using restriction mapping, DNA sequence analysis, and/or PCR analysis. Bacterial cells harboring the correct plasmid can be stored as cell banks.

V. Immunogenic and Pharmaceutical Compositions

Further disclosed are compositions, e.g., immunogenic or pharmaceutical compositions that contain an effective amount of the multivalent oligopeptide, DT, and/or PSM as described herein, or a polynucleotide encoding the polypeptide of the disclosure. Compositions as described herein can further comprise additional immunogenic components, e.g., as a multivalent vaccine, as well as carriers, excipients or adjuvants.

Compositions as described herein can be formulated according to known methods. Suitable preparation methods are described, for example, in *Remington's Pharmaceutical Sciences,* 19th Edition, A. R. Gennaro, ed., Mack Publishing Co., Easton, Pa. (1995), which is incorporated herein by reference in its entirety. Composition can be in a variety of forms, including, but not limited to an aqueous solution, an emulsion, a gel, a suspension, lyophilized form, or any other form known in the art. In addition, the composition can contain pharmaceutically acceptable additives including, for example, diluents, binders, stabilizers, and preservatives. Once formulated, compositions of the disclosure can be administered directly to the subject. The subjects to be treated can be animals; in particular, human subjects can be treated.

Carriers that can be used with compositions of the disclosure are well known in the art, and include, without limitation, e.g., thyroglobulin, albumins such as human serum albumin, tetanus toxoid, and polyamino acids such as poly L-lysine, poly L-glutamic acid, influenza, hepatitis B virus core protein, and the like. A variety of aqueous carriers can be used, e.g., water, buffered water, 0.8% saline, 0.3% glycine, hyaluronic acid and the like. Compositions can be sterilized by conventional, well known sterilization techniques, or can be sterile filtered. A resulting composition can be packaged for use as is, or lyophilized, the lyophilized preparation being combined with a sterile solution prior to administration. Compositions can contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamineoleate, etc.

Certain compositions as described herein further include one or more adjuvants, a substance added to an immunogenic composition to, for example, enhance, sustain, localize, or modulate an immune response to an immunogen. The term "adjuvant" refers to any material having the ability to (1) alter or increase the immune response to a particular antigen or (2) increase or aid an effect of a pharmacological agent. Any compound which can increase the expression, antigenicity or immunogenicity of the polypeptide is a potential adjuvant. The term "immunogenic carrier" as used herein refers to a first moiety, e.g., a polypeptide or fragment, variant, or derivative thereof which enhances the immunogenicity of a second polypeptide or fragment, variant, or derivative thereof.

A great variety of materials have been shown to have adjuvant activity through a variety of mechanisms. For example, an increase in humoral immunity is typically manifested by a significant increase in the titer of antibodies raised to the antigen, and an increase in T-cell activity is typically manifested in increased cell proliferation, or cellular cytotoxicity, or cytokine secretion. An adjuvant can also alter or modulate an immune response, for example, by changing a primarily humoral or $Th_2$ response into a primarily cellular, or $Th_1$ response. Immune responses to a given antigen can be tested by various immunoassays well known to those of ordinary skill in the art, and/or described elsewhere herein.

A wide number of adjuvants are familiar to persons of ordinary skill in the art, and are described in numerous references. Adjuvants which can be used in compositions described herein include, but are not limited to: inert carriers, such as alum, bentonite, latex, and acrylic particles; incomplete Freund's adjuvant, complete Freund's adjuvant; aluminum-based salts such as aluminum hydroxide; Alhydrogel ($Al(OH)_3$)); aluminum phosphate ($AlPO_4$); calcium-based salts; silica; any TLR biological ligand(s); IDC-1001 (also known as GLA-SE; glucopyranosyl lipid adjuvant stable emulsion) (Coler et al., PLoS One, 2010. 5(10): p. e13677; Coler et al., PLoS One, 2011. 6(1): p. e16333); CpG (Mullen et al., PLoS One, 2008. 3(8): p. e2940), or any combination thereof. The amount of adjuvant, how it is formulated, and how it is administered all parameters which are well within the purview of a person of ordinary skill in the art.

In some embodiments, a composition of the disclosure further comprises a liposome or other particulate carrier, which can serve, e.g., to stabilize a formulation, to target the formulation to a particular tissue, such as lymphoid tissue, or to increase the half-life of the polypeptide composition. Such particulate carriers include emulsions, foams, micelles, insoluble monolayers, liquid crystals, phospholipid dispersions, lamellar layers, iscoms, and the like. In these preparations, the polypeptide described herein can be incorporated as part of a liposome or other particle, or can be delivered in conjunction with a liposome. Liposomes for use in accordance with the disclosure can be formed from standard vesicle-forming lipids, which generally include neutral and negatively charged phospholipids and a sterol, such as cholesterol. A composition comprising a liposome or other particulate suspension as well as the polypeptide as described herein can be administered intravenously, locally, topically, etc. in a dose which varies according to, inter alia, the manner of administration, the polypeptide being delivered, and the stage of the disease being treated.

For solid compositions, conventional nontoxic solid carriers can be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, the polypeptide as described herein, often at a concentration of 25%-75%.

For aerosol or mucosal administration, the polypeptide as described herein can be supplied in finely divided form, optionally along with a surfactant and, propellant and/or a mucoadhesive, e.g., chitosan. The surfactant must, of course, be pharmaceutically acceptable, and in some embodiments soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides can be employed. The surfactant can constitute 0.1%-20% by weight of the composition, in some embodiments 0.25-5% by weight. The balance of the composition is ordinarily propellant, although an atomizer can be used in which no propellant is necessary and other percentages are adjusted accordingly. In some embodiments, the immunogenic polypeptides can be incorporated within an aerodynamically light particle, such as those particles described in U.S. Pat. No. 6,942,868 or U.S. Pat. Pub. No. 2005/0008633. A carrier can also be included, e.g., lecithin for intranasal delivery.

The disclosure is also directed to a method of producing the composition according to the disclosure. In some embodiments, the method of producing the composition comprises (a) isolating a polypeptide according to the disclosure; and (b) adding an adjuvant, carrier and/or excipient to the isolated polypeptide. Some embodiments disclose further combining the polypeptide with other staphylococcal antigens.

Some embodiments include a multivalent vaccine. A multivalent vaccine of the present disclosure can include a multivalent oligopeptide, DT, and/or PSM as described herein, or a polynucleotide encoding a multivalent oligopeptide, DT, and/or PSM, and one or more additional immunogenic components. Such components can be additional immunogens of the same infectious agent, e.g., *S. aureus*, or from other staphylococci, or can be immunogens derived from other infectious agents which can be effectively, conveniently, or economically administered together. In certain embodiments, the multivalent oligopeptide, DT, and/or PSM as described herein, can be combined with other toxins or other virulent component-based vaccines to make a broad toxin-based multivalent vaccine capable of targeting multiple bacterial virulence determinants. In other embodiments, the multivalent oligopeptide, DT, and/or PSM as described herein can be fused to other immunogenic, biologically significant, or protective epitope containing polypeptides to generate a multivalent vaccine in a single chain and induce an immune response against multiple antigens. In yet another embodiment, the multivalent oligopeptide, DT, and/or PSM as described herein, can be fused to one or more T cell epitopes to induce T cell immunity.

VI. Methods of Treatment/Prevention and Regimens

Also provided is a method of treating or preventing *Staphylococcus* infection, e.g., *S. aureus* infection or treating or preventing a disease caused by *Staphylococcus*, e.g, *S. aureus* in a subject, comprising administering to a subject in need thereof a composition as described herein comprising a multivalent oligopeptide, DT, and/or PSM as described herein, or polynucleotides, vectors, or host cells encoding same. In certain embodiments, the subject is an animal, e.g., a vertebrate, e.g., a mammal, e.g., a human. Some embodiments include a method of inducing an immune response against a *S. aureus* strain, comprising administering to a subject in need of said immune response an effective amount of a composition comprising a multivalent oligopeptide, DT, and/or PSM as described herein, or polynucleotides, vectors, or host cells encoding same.

In some embodiments, a subject is administered a composition comprising a multivalent oligopeptide, DT, and/or PSM as described herein, or polynucleotides, vectors, or host cells encoding same prophylactically, e.g., as a prophylactic vaccine, to establish or enhance immunity to *Staphylococcus*, e.g., *S. aureus*, in a healthy animal prior to potential or actual exposure to *Staphylococcus*, e.g., *S. aureus* or contraction of a *Staphylococcus*-related symptom, thus preventing disease, alleviating symptoms, reducing symptoms, or reducing the severity of disease symptoms. In one embodiment the disease is a respiratory disease, e.g., pneumonia. Other diseases or conditions to be treated or prevented include, but are not limited to, bacteremia, sepsis, skin infections, wound infections, endocarditis, bone and joint infections, osteomyelitis, and/or meningitis. One or more compositions, polypeptides, polynucleotides, vectors, or host cells as described herein can also be used to treat a subject already exposed to *Staphylococcus*, e.g., *S. aureus*, or already suffering from a *Staphylococcus* related symptom to further stimulate the immune system of the animal, thus reducing or eliminating the symptoms associated with that exposure. As defined herein, "treatment of an animal" refers to the use of one or more compositions, polypeptides, polynucleotides, vectors, or host cells of the disclosure to prevent, cure, retard, or reduce the severity of *S. aureus* symptoms in an animal, and/or result in no worsening of *S. aureus* symptoms over a specified period of time. It is not required that any composition, polypeptide, polynucleotide, a vector, or a host cell as described herein provides total protection against a staphylococcal infection or totally cure or eliminate all *Staphylococcus* related symptoms.

As used herein, "a subject in need of therapeutic and/or preventative immunity" refers to a subject in which it is desirable to treat, i.e., to prevent, cure, retard, or reduce the severity of *Staphylococcus* related symptoms, or result in no worsening of *Staphylococcus* related symptoms over a specified period of time. As used herein, "a subject in need of the immune response" refers to a subject for which an immune response(s) against a S *Staphylococcus* related disease is desired.

Treatment with pharmaceutical compositions comprising an immunogenic composition, polypeptide or polynucleotide as described herein can occur separately or in conjunction with other treatments, as appropriate.

In therapeutic applications, a composition, polypeptide or polynucleotide of the disclosure is administered to a patient in an amount sufficient to elicit an effective innate, humoral and/or cellular response to the multivalent oligopeptide, DT, and/or PSM to cure or at least partially arrest symptoms or complications.

An amount adequate to accomplish this is defined as "therapeutically effective dose" or "unit dose." Amounts effective for this use will depend on, e.g., the polypeptide or polynucleotide composition, the manner of administration, the stage and severity of the disease being treated, the weight and general state of health of the patient, and the judgment of the prescribing physician. In some embodiments, a priming dose is followed by a boosting dose over a period of time.

In alternative embodiments, generally for humans an initial immunization (that is for therapeutic or prophylactic administration) is administered followed by boosting dosages in the same dose range pursuant to a boosting regimen over weeks to months depending upon the patient's response and condition by measuring the antibody or T lymphocyte response in the patient's blood.

Polypeptides and compositions as described herein can generally be employed in serious disease states, that is, life-threatening or potentially life threatening situations. In such cases, in view of the minimization of extraneous substances and the relative nontoxic nature of the polypeptides, it is possible and can be felt desirable by the treating physician to administer substantial excesses of these polypeptide compositions.

For therapeutic use, administration can begin at the first sign of *S. aureus* infection or risk factors. In certain embodiments, the initial dose is followed by boosting doses until, e.g., symptoms are substantially abated and for a period thereafter. In frequent infection, loading doses followed by boosting doses can be required.

In certain embodiments, the composition as described herein is delivered to a subject by methods described herein, thereby achieving an effective immune response, and/or an effective therapeutic or preventative immune response. Any mode of administration can be used so long as the mode results in the delivery and/or expression of the desired polypeptide in the desired tissue, in an amount sufficient to generate an immune response to *Staphylococcus*, e.g., *S. aureus*, and/or to generate a prophylactically or therapeutically effective immune response to *Staphylococcus*, e.g., to *S. aureus*, in an animal in need of such response. According to the disclosed methods, a composition described herein can be administered by mucosal delivery, transdermal delivery, subcutaneous injection, intravenous injection, oral administration, pulmonary administration, intramuscular (i.m.) administration, or via intraperitoneal injection. Other suitable routes of administration include, but not limited to intratracheal, transdermal, intraocular, intranasal, inhalation, intracavity, intraductal (e.g., into the pancreas) and intraparenchymal (i.e., into any tissue) administration. Transdermal delivery includes, but not limited to intradermal (e.g., into the dermis or epidermis), transdermal (e.g., percutaneous) and transmucosal administration (i.e., into or through skin or mucosal tissue). Intracavity administration includes, but not limited to administration into oral, vaginal, rectal, nasal, peritoneal, or intestinal cavities as well as, intrathecal (i.e., into spinal canal), intraventricular (i.e., into the brain ventricles or the heart ventricles), intra-arterial (i.e., into the heart atrium) and sub arachnoidal (i.e., into the sub arachnoid spaces of the brain) administration.

Any mode of administration can be used so long as the mode results in the delivery and/or expression of the desired polypeptide in an amount sufficient to generate an immune response to Staphylococcus, e.g., S. aureus, and/or to generate a prophylactically or therapeutically effective immune response to Staphylococcus, e.g., S. aureus, in an animal in need of such response. Administration as described herein can be by e.g., needle injection, or other delivery or devices known in the art.

In some embodiments, a composition comprising a multivalent oligopeptide, DT, and/or PSM as described herein, or polynucleotides, vectors, or host cells encoding same, stimulate an antibody response or a cell-mediated immune response sufficient for protection of an animal against Staphylococcus, e.g., S. aureus infection. In other embodiments, a composition comprising a multivalent oligopeptide, DT, and/or PSM as described herein, or polynucleotides, vectors, or host cells encoding same, stimulate both a humoral and a cell-mediated response, the combination of which is sufficient for protection of an animal against Staphylococcus, e.g., S. aureus infection. In some embodiments, a composition comprising a multivalent oligopeptide, DT, and/or PSM as described herein, or polynucleotides, vectors, or host cells encoding same, further stimulates an innate, an antibody, and/or a cellular immune response.

In some embodiments, a composition comprising a multivalent oligopeptide, DT, and/or PSM as described herein, or polynucleotides, vectors, or host cells encoding same, can induce antibody responses to S. aureus. In certain embodiments, components that induce T cell responses (e.g., T cell epitopes) are combined with components such as the polypeptides as described herein that primarily induce an antibody response.

Further disclosed is a method for generating, enhancing, or modulating a protective and/or therapeutic immune response to S. aureus infection in a subject, comprising administering to a subject in need of therapeutic and/or preventative immunity one or more of the compositions as described herein.

The compositions as described herein can be administered to an animal at any time during the lifecycle of the animal to which it is being administered. In humans, administration of the composition as described herein can, and often advantageously occurs while other vaccines are being administered, e.g., as a multivalent vaccine as described elsewhere herein.

Furthermore, the composition as described herein can be used in any desired immunization or administration regimen; e.g., in a single administration or alternatively as part of periodic vaccination regimes such as annual vaccinations, or as in a prime-boost regime in which composition or polypeptide or polynucleotide of the disclosure is administered either before or after the administration of the same or of a different polypeptide or polynucleotide. Recent studies have indicated that a prime-boost protocol is often a suitable method of administering vaccines. In a prime-boost protocol, one or more compositions as described herein can be utilized in a "prime boost" regimen. An example of a "prime boost" regimen can be found in Yang, Z. et al. *J Virol.* 77:799-803, 2002, which is incorporated herein by reference in its entirety.

Infections to be treated include, but are not limited to a localized or systemic infection of skin, soft tissue, blood, or an organ or an auto-immune disease. Specific diseases or conditions to be treated or prevented include, but are not limited to, respiratory diseases, e.g., pneumonia, sepsis, skin infections, wound infections, endocarditis, bone and joint infections, osteomyelitis, and/or meningitis.

A number of animal models for *S. aureus* infection are known in the art, and can be used with the methods disclosed herein without undue experimentation. For example, a hamster model of methicillin-resistant *Staphylococcus aureus* (MRSA) pneumonia has been described for the testing of antimicrobials. (Verghese A. et al., *Chemotherapy.* 34:497-503 (1988), Kephart P A. et al. J Antimicrob *Chemother.* 21:33-9, (1988)). Further, a model of *S. aureus*-induced pneumonia in adult, immunocompetent C57BL/6J mice is described, which closely mimics the clinical and pathological features of pneumonia in human patients. (Bubeck-Wardenburg J. et al., *Infect Immun.* 75:1040-4 (2007)). Additionally, virulence has been tested in a rat model of *S. aureus* pneumonia as described in McElroy et al. (McElroy M C. et al., *Infect Immun.* 67:5541-4 (1999)). Finally, a standardized and reproducible model of MRSA-induced septic pneumonia to evaluate new therapies was established in sheep. (Enkhbaatar P. et al., *Shock.* 29(5):642-9 (2008)).

The practice of the disclosure will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., Sambrook et al., ed., Cold Spring Harbor Laboratory Press: (1989); Molecular Cloning: A Laboratory Manual, Sambrook et al., ed., Cold Springs Harbor Laboratory, New York (1992), DNA Cloning, D. N. Glover ed., Volumes I and II (1985); Oligonucleotide Synthesis, M. J. Gait ed., (1984); Mullis et al. U.S. Pat. No. 4,683,195; Nucleic Acid Hybridization, B. D. Hames & S. J. Higgins eds. (1984); Transcription And Translation, B. D. Hames & S. J. Higgins eds. (1984); Culture Of Animal Cells, R. I. Freshney, Alan R. Liss, Inc., (1987); Immobilized Cells And Enzymes, IRL Press, (1986); B. Perbal, A Practical Guide To Molecular Cloning (1984); the treatise, Methods In Enzymology, Academic Press, Inc., N.Y.; Gene Transfer Vectors For Mammalian Cells, J. H. Miller and M. P. Calos eds., Cold Spring Harbor Laboratory (1987); Methods In Enzymology, Vols. 154 and 155 (Wu et al. eds.); Immunochemical Methods In Cell And Molecular Biology, Mayer and Walker, eds., Academic Press, London (1987); Handbook Of Experimental Immunology, Volumes I-IV, D. M. Weir and C. C. Blackwell, eds., (1986); Manipulating the Mouse Embryo, Cold Spring Harbor Laboratory Press, Cold Spring Harbor, N.Y., (1986); and in Ausubel et al., Current Protocols in Molecular Biology, John Wiley and Sons, Baltimore, Md. (1989).

Standard reference works setting forth general principles of immunology include Current Protocols in Immunology, John Wiley & Sons, New York; Klein, J., Immunology: The Science of Self-Nonself Discrimination, John Wiley & Sons, New York (1982); Roitt, I., Brostoff, J. and Male D., Immunology, 6th ed. London: Mosby (2001); Abbas A., Abul, A. and Lichtman, A., Cellular and Molecular Immunology, Ed. 5, Elsevier Health Sciences Division (2005); and Harlow and Lane, Antibodies: A Laboratory Manual, Cold Spring Harbor Press (1988).

EXAMPLES

The breadth and scope of the present disclosure should not be limited by any of the above-described exemplary embodiments, but should be defined only in accordance with the following claims and their equivalents.

Example 1

Generation of Attenuated Mutants of δ-Toxin and PSMα3

The δ-toxin and PSM oligopeptides require an amphiphilic a-helical structure to exhibit the surfactant properties (Omae, et al., 2012, *J Biol Chem*, 287 (19):15570-15579; Wang, et al., 2007, *Nat Med*, 13 (12):1510-1514). These peptides consist of a hydrophobic and a hydrophilic surface as shown in FIG. 1A for the four PSM-α oligopeptides, two PSM-β oligopeptides, and the δ-toxin oligopeptide. These peptides consist of a hydrophobic and a hydrophilic surface as shown in FIG. 1A for the four PSM-α oligopeptides, two PSM-β oligopeptides, and the δ-toxin oligopeptide. The hydrophobic face of PSM-mec is shown in FIG. 1A (hydrophobic face shown in the lower half of the circular depictions of the peptides). The peptides are shown in Table 3, with hydrophobic face residues underlined.

TABLE 3

OLIGOPEPTIDE SEQUENCES

| Peptide | Sequence (hydrophobic face residues underlined) | SEQ ID NO |
|---|---|---|
| δ toxin | MAQD<u>II</u>S<u>TI</u>GDL<u>V</u>KW<u>II</u>DT<u>V</u>NKFTKK | 1 |
| PSMα1 | MG<u>IIA</u>G<u>II</u>K<u>VI</u>KSL<u>IE</u>Q<u>F</u>TGK | 38 |
| PSMα2 | MG<u>IIA</u>G<u>II</u>K<u>FI</u>KGL<u>IE</u>K<u>F</u>TGK | 12 |
| PSMα3 | ME<u>F</u>VAK<u>L</u>F<u>K</u>F<u>F</u>KDL<u>L</u>GK<u>F</u>LGNN | 6 or 13 |
| PSMα4 | MA<u>IV</u>G<u>TII</u>K<u>II</u>KA<u>II</u>D<u>IF</u>AK | 14 |
| PSMβ1 | MEGL<u>F</u>NA<u>I</u>KDT<u>V</u>TAA<u>I</u>NNDGAKLGTS<u>I</u>VN<u>I</u>VENGVGLLSKLFGF | 15 |
| PSMβ2 | MTG<u>L</u>AE<u>AI</u>ANT<u>V</u>QAAQQHDSVK<u>L</u>GTS<u>I</u>VD<u>I</u>VANGVGLLGKLFGF | 16 |
| PSM-mec | MD<u>F</u>TG<u>VI</u>TS<u>II</u>D<u>L</u>IKT<u>CI</u>QAFG | 52 |

Helical wheel structures shown in FIG. 1 were created using Heliquest software (heliquest.ipmc.cnrs.fr) to define and display properties such as hydrophobicity and hydrophobic moment, net charge (z) (Gautier, et al., 2008, *Bioinformatics*, 24 (18):2101-2102). Mutations disrupting the helical structure can eliminate the surfactant properties (Omae, et al., 2012, *J Biol Chem*, 287 (19):15570-15579) but could also decrease vaccine potency of the mutant. Therefore, we generated mutants by minimizing the disruption of the a-helix and to preserve immunogenicity of peptides. To eliminate surfactant properties we replaced several amino acids in the hydrophobic face of PSMα3 and δ-toxin with less hydrophobic amino acids like alanine, and glycine. The model predicts that these small amino acids will not drastically change protein structure but will substantially decrease hydrophobicity (FIG. 1B). We introduced mutations in two residues in the hydrophobic face of both PSMα3 (V4 and L14) and δ-toxin (L12 and V20). The mutants are shown in Table 4.

TABLE 4

MUTATED TOXIN SEQUENCES

| | SEQUENCE (Mutated Residues Underlined) | SEQ ID NO |
|---|---|---|
| Delta toxin mutants | | |
| Wt | MAQDIISTIGDLVKWIIDTVNKFTKK | 1 |
| ALA-1 | MAQDIISTIGD<u>A</u>VKWIIDTVNKFTKK | 2 |
| ALA-2 | MAQDIISTIGD<u>A</u>VKWIIDT<u>A</u>NKFTKK | 3 |
| GLY-1 | MAQDIISTIGD<u>G</u>VKWIIDTVNKFTKK | 4 |
| GLY-2 | MAQDIISTIGD<u>G</u>VKWIIDT<u>G</u>NKFTKK | 5 |
| PSM-α3 mutants | | |
| WT | MEFVAKLFKFFKDLLGKFLGNN | 6 or 13 |
| ALA-1 | MEFVAKLFKFFKD<u>A</u>LGKFLGNN | 7 |
| ALA-2 | MEF<u>A</u>AKLFKFFKD<u>A</u>LGKFLGNN | 8 |
| GLY-1 | MEFVAKLFKFFKD<u>G</u>LGKFLGNN | 9 |

TABLE 4-continued

MUTATED TOXIN SEQUENCES

| | SEQUENCE (Mutated Residues Underlined) | SEQ ID NO |
|---|---|---|
| GLY-2 | MEF<u>G</u>AKLFKFFKD<u>G</u>LGKFLGNN | 10 |
| GLY-ALA | MEF<u>G</u>AKLFKFFKD<u>A</u>LGKFLGNN | 11 |

We engineered single and double mutants by replacing these two amino acids either by alanine or by glycine or both. As shown in FIG. 1B, the mutant constructs have decreased hydrophobicity and hydrophobic moment compared to wild type toxin as analyzed by Heliquest program (Gautier, et al., 2008, *Bioinformatics*, 24 (18):2101-2102). Similar mutants can be generated by further mutations in the hydrophobic face as additional potential attenuated toxoids.

Example 2

Evaluation of Attenuation of δ-Toxin and PSMα3 Mutants

Mutations ala1, ala2, and gly2 were incorporated into delta toxin sequence and the mutants were tested for lytic activity towards horse red blood cells (HRBC) by the following method. Toxicity assay using horse blood: 5 ml horse blood was centrifuged at 2,000 RPM for 10 min at 20° C. Supernatant was discarded and pellet was washed once with 15 ml PBS. Required percentage of the horse RBC cells was prepared in PBS by resuspending the pellet (wt/vol). 100 μl of the various oligopeptides were added in 100 μl of horse RBC (different percentage as per required) in ELISA dilution plate and then plates were incubated at 37° C. for 45 min. Plates were then centrifuged and 100 μl of the supernatant was transferred into new NUNC ELISA plate. Absorbance in the supernatant was determined in Versamax™ plate reader (Molecular Devices CA) at 416 nm. The optical density of the supernatant reflects the degree of hemolysis of red blood cells caused by the toxin.

Neutralization Assay: For neutralization, diluted serum samples were added to 50 of the various oligopeptides (12.5 μg/ml), incubated 10 min at room temperature, and then 100 μl of 5% horse RBC were added. The plates were incubated 37° C. for 45 min. Plates were then centrifuged and 100 μl of the supernatant was transferred into new NUNC ELISA plate. Absorbance in the supernatants were determined in a Versamax™ plate reader (Molecular Devices CA) at 416 nm.

As shown in FIG. 2, delta toxin mutants ala1 (L12A), ala2 (L12A/V20A), and gly2 (L12G/V20G) were fully attenuated. To test if the mutants retained their neutralizing epitopes we tested the delta toxin-ala2 mutant for binding to human neutralizing antibodies in a pool of high titer human sera generated by screening individual normal sera. As shown in FIG. 3, delta toxin toxicity can be effectively neutralized with a 1:450 dilution of human serum pool. Delta toxin-ala2 neither induced significant lysis of the cells nor did it change the toxicity of delta toxin when the toxin and mutant were combined. However, pre-incubation with delta toxin-ala2 (22.5 μg/ml) significantly reduced the neutralizing capacity of the human sera (FIG. 3, compare $3^{rd}$ and $7^{th}$ bar) towards delta toxin (11.25 μg/ml). Since 2 fold excess of mutant can significantly reduce the neutralizing capacity of the sera by ~50% shows that the attenuated mutant retains the ability to bind to neutralizing antibodies present in the human serum.

Figure 4:
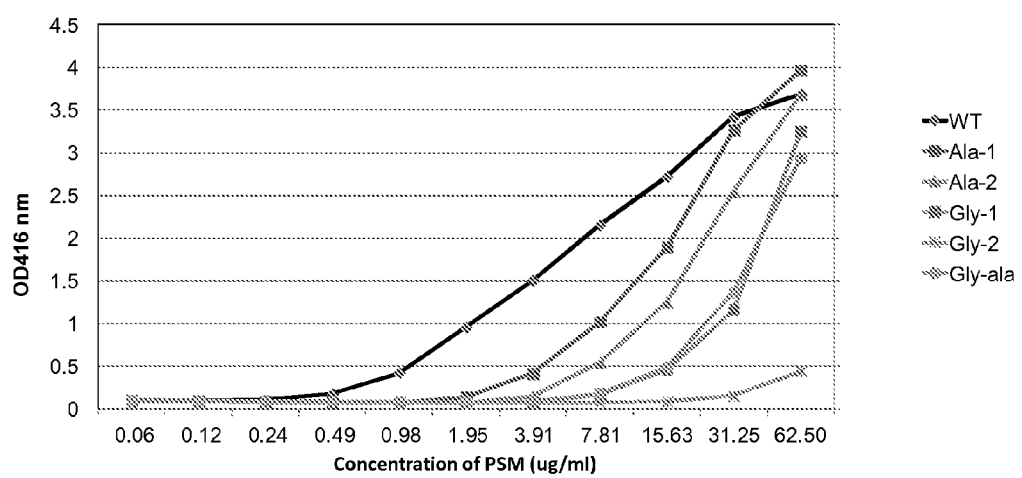

We also generated mutants at positions V4 and L15 of PSMα3. As shown in FIG. 4, mutation of both these sites in PSM to glycine (PSM-gly2: V4A/L15A) strongly attenuated the toxin while the other mutants showed partial attenuation.

Example 3

Generation of Fusion Constructs of AT62 with Delta Toxin and PSM

Figure 5:
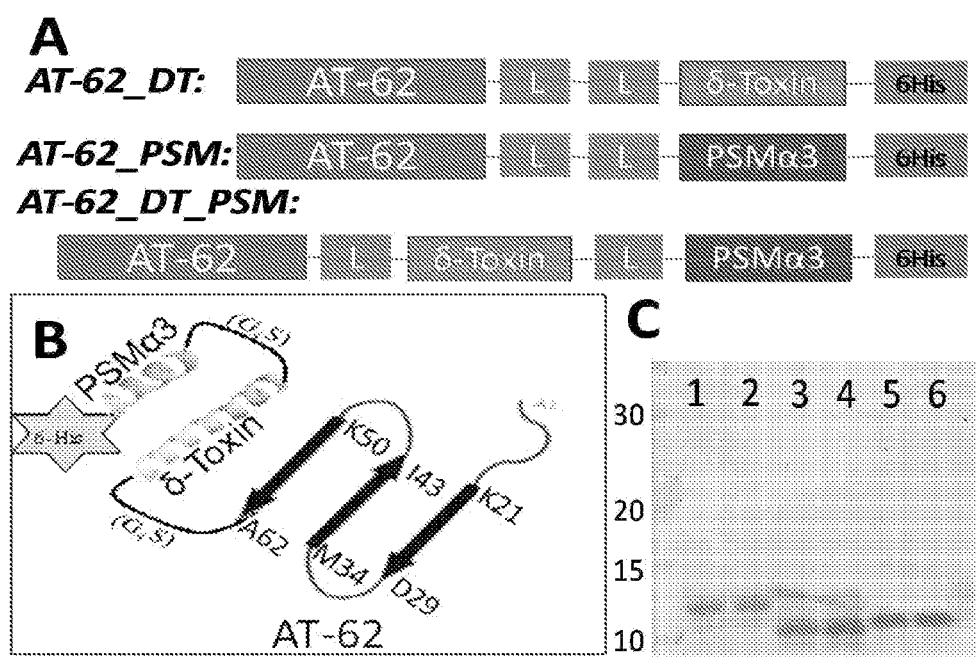

The AT62 vaccine has shown efficacy when tested in different animal models (Adhikari, et al., 2012, *PLoS One*, 7 (6):e38567). We generated three fusion proteins with AT62 as the core subunit fused to PSMα3, δ-toxin, or both using a flexible linker (GGGGS; i.e. G4S) flanked with a C-terminal 6xHis (FIG. 5A&B). The nucleic acid sequences codon optimized for expression in *E. coli* were prepared, and the three fusion proteins were produced at small scale. The specificity and the size of the constructs were confirmed by western blot with AT62 specific antibodies (6C12) (FIG. 5C). The sequences are presented in Table 5. In each instance, the AT62 oligopeptide is single-underlined, delta toxin is double-underlined, and PSM PSMα3 has a broken underline. Additional fusion proteins including AT62 and staphylococcal exotoxin B (SEB) are also presented

TABLE 5

AT62 FUSION OLIGOPEPTIDES

| Fusion Peptide | Amino Acid Sequence | SEQ ID NO | Codon-Optimized Nucleic Acid Sequence | SEQ ID NO |
|---|---|---|---|---|
| AT62_DT | ADSDINIKTGTTDIGSNTTVKT GDLVTYDKENGMHKKVFYSFI DDKNHNKKLLVIRTKGTIAGG GGSGGGGSMAQDIISTIGDLVK WIIDTVNKFTKKHHHHHH | 18 | ATGGCGGATAGCGACATCAACATCA AAACGGGTACTACGGACATTGGCAG CAATACGACCGTCAAGACCGGTGAT CTGGTCACCTATGACAAAGAGAATG GTATGCACAAAAAGGTGTTTTACAG CTTCATTGATGACAAAAATCACAAC AAGAAGCTGTTGGTTATTCGTACCA AAGGCACCATTGCCGGTGGTGGCGG TTCCGGCGGTGGCGGTAGCATGGCA CAGGACATCATCTCTACCATCGGCG ATCTGGTGAAATGGATCATTGATAC CGTTAACAAGTTCACGAAAAAGCAT CATCACCATCACCACTGATAACTCG AGCACCACCACCACCACCACTGAGA TCCG | 17 |

TABLE 5 -continued

AT62 FUSION OLIGOPEPTIDES

| Fusion Peptide | Amino Acid Sequence | SEQ ID NO | Codon-Optimized Nucleic Acid Sequence | SEQ ID NO |
|---|---|---|---|---|
| AT62_PSM | MADSDINIKTGTTDIGSNTTV KTGDLVTYDKENGMHKKVF YSFIDDKNHNKKLLVIRTKGT IAGGGGSGGGGSMEFVAKLF KFFKDLLGKFLGNNHHHHHH | 20 | ATGGCGGATAGCGACATCAACATCAA AACGGGTACTACGGACATTGGCAGCA ATACGACCGTCAAGACCGGTGATCTG GTCACCTATGACAAAGAGAATGGTAT GCACAAAAAGGTGTTTTACAGCTTCA TTGATGACAAAAATCACAACAAGAAG CTGTTGGTTATTCGTACCAAAGGCACC ATTGCCGGTGGTGGCGGCTCCGGTGG CGGTGGTTCTATGGAATTTGTTGCAAA GCTGTTCAAATTCTTTAAGGATCTGCT GGGTAAATTCCTGGGCAACAACCATC ATCACCATCACCACTGATAACT | 19 |
| AT62_DT_PSM | MADSDINIKTGTTDIGSNTTV KTGDLVTYDKENGMHKKVF YSFIDDKNHNKKLLVIRTKGT IAGGGGSMAQDIISTIGDLVK WIIDTVNKFTKKGGGGSMEF VAKLFKFFKDLLGKFLGNNH HHHH | 22 | ATGGCGGATAGCGACATCAACATCAA AACGGGTACTACGGACATTGGCAGCA ATACGACCGTCAAGACCGGTGATCTG GTCACCTATGACAAAGAGAATGGTAT GCACAAAAAGGTGTTTTACAGCTTCA TTGATGACAAAAATCACAACAAGAAG CTGTTGGTTATTCGTACCAAAGGCACC ATTGCCGGTGGTGGTGGTTCTATGGCG CAGGACATCATTTCCACGATCGGCGA TCTGGTTAAATGGATCATCGACACCGT GAACAAGTTTACCAAGAAAGGTGGTG GCGGTAGCATGGAATTTGTTGCAAAA CTGTTCAAATTCTTTAAGGATCTGCTG GGCAAGTTCCTGGGCAACAATCATCA TCACCATCACCACTGATAA | 21 |
| AT62_rSEB | MADSDINIKTGTTDIGSNTTVK TGDLVTYDKENGMHKKVFYS FIDDKNHNKKLLVIRTKGTIAG GGGSGGGGSESQPDPKPDELH KSSKFTGLMENMKVLYDDNH VSAINVKSIDQFRYFDLIYSIKD TKLGNYDNVRVEFKNKDLAD KYKDKYVDVFGANAYYQCAF SKKTNDINSHQTDKRKTCMYG GVTEHNGNQLDKYRSITVRVF EDGKNLLSFDVQTNKKKVTAQ ELDYLTRHYLVKNKKLYEFNN SPYETGYIKFIENENSFWYDM MPAPGDKFDQSKYLMMYNDN KMVDSKDVKIEVYLTTKKK | 23 | CATATGGCAGACTCGGACATCAACAT CAAAACGGGCACGACGGACATTGGCT CAAACACGACGGTGAAAACGGGCGAC CTGGTGACCTACGACAAAGAAACGG CATGCATAAAAAAGTGTTTTATAGCTT CATCGATGACAAAAACCACAACAAAA AACTGCTGGTCATTCGTACCAAGGGT ACGATCGCAGGTGGTGGTGGTTCTGG CGGTGGTGGTAGTGAATCCCAGCCGG ACCCGAAACCGGACGAACTGCATAAA AGCTCTAAATTTACCGGCCTGATGGA AAATATGAAAGTGCTGTATGATGACA ACCACGTGTCAGCCATTAATGTTAAAT CGATCGATCAATTCCGTTATTTCGACC TGATTTACTCAATCAAAGATACCAAA CTGGGCAACTATGACAATGTGCGCGT TGAATTCAAAAACAAAGATCTGGCAG ACAAATACAAAGATAAATACGTCGAC GTGTTCGGTGCGAATGCCTATTACCAG TGCGCTTTCAGCAAGAAAACCAACGA TATCAACTCTCATCAAACCGACAAAC GTAAAACGTGTATGTATGGCGGTGTG ACCGAACACAACGGCAATCAGCTGGA TAAATACCGTAGTATCACGGTTCGCGT CTTTGAAGATGGTAAAAACCTGCTGT CCTTCGATGTCCAGACCAACAAGAAA AAAGTGACGGCACACAAGAACTGGATTA TCTGACCCGCCATTACCTGGTTAAAAA CAAAAAACTGTACGAATTCAACAACT CACCGTATGAAACGGGCTACATCAAA TTCATCGAAAACGAAAACTCGTTCTG GTACGATATGATGCCGGCCCCGGGCG ATAAAATTCGACCAGTCCAAATATCTG ATGATGTACAATGATAACAAAATGGT TGACTCCAAAGATGTGAAAATCGAAG TTTACCTGACGACGAAAAAAAATAA GGATCC | 25 |

TABLE 5 -continued

AT62 FUSION OLIGOPEPTIDES

| Fusion Peptide | Amino Acid Sequence | SEQ ID NO | Codon-Optimized Nucleic Acid Sequence | SEQ ID NO |
|---|---|---|---|---|
| rSEB_AT62 | MESQPDPKPDELHKSSKFTGL MENMKVLYDDNHVSAINVKSI DQFRYFDLIYSIKDTKLGNYDN VRVEFKNKDLADKYKDKYVD VFGANAYYQCAFSKKTNDINS HQTDKRKTCMYGGVTEHNGN QLDKYRSITVRVFEDGKNLLSF DVQTNKKKVTAQELDYLTRH YLVKNKKLYEFNNSPYETGYI KFIENENSFWYDMMPAPGDKF DQSKYLMMYNDNKMVDSKD VKIEVYLTTKKKGGGGS GGGG SADSDINIKTGTTDIGSNTTVKT GDLVTYDKENGMHKKVFYSFI DDKNIINKKLLVIRTKGTIA | 26 | CATATGGAAAGCCAACCGGACCCGAA ACCGGACGAACTGCATAAAAGCTCAA AATTCACGGGCCTGATGGAAAACATG AAAGTGCTGTACGACGATAACCATGT CAGTGCAATTAATGTGAAATCCATCG ATCAGTTTCGTTATTTCGACCTGATTT ACTCAATCAAAGATACCAAACTGGGC AACTATGACAATGTGCGCGTTGAATT CAAAAACAAAGATCTGGCAGACAAAT ACAAAGATAAATACGTCGACGTGTTC GGTGCGAATGCCTATTACCAGTGCGC TTTCAGCAAGAAAACCAACGATATTA ATTCGCATCAAACCGACAAACGTAAA ACGTGTATGTATGGCGGTGTCACCGA ACACAACGGCAATCAACTGGATAAAT ACCGTAGCATCACGGTTCGCGTCTTTG AAGATGGTAAAAACCTGCTGTCTTTC GACGTGCAGACCAACAAGAAAAAAGT TACGGCGCAAGAACTGGATTATCTGA CCCGCCATTACCTGGTTAAAAACAAA AAACTGTACGAATTCAACAACTCACC GTATGAAACGGGCTACATCAAATTCA TCGAAAACGAAAACTCGTTCTGGTAC GATATGATGCCGGCCCCGGGCGATAA ATFCGACCAGAGTAAATACCTGATGA TGTACAACGATAACAAAATGGTGGAT TCCAAAGACGTGAAAATTGAAGTTTA TCTGACCACCAAGAAAAAAGGTGGTG GTGGTAGCGGTGGTGGTGGTAGCGCC GATTCTGACATTAACATCAAAACCGG CACCACGGATATCGGTTCTAATACCA CGGTTAAAACCGGCGATCTGGTCACG TATGACAAAGAAAACGGTATGCACAA AAAAGTGTTTTATTCCTTCATTGACGA CAAAAATCACAACAAAAAACTGCTGG TTATCCGCACGAAAGGCACCATCGCA TAAGGATCC | 28 |
| AT62_rSEB_DT | MADSDINIKTGTTDIGSNTTV KTGDLVTYDKENGMHKKVF YSFIDDKNHNKKLLVIRTKGT IAGGGGSESQPDPKPDELHKS SKFTGLMENMKVLYDDNHV SAINVKSIDQFRYFDLIYSIKD TKLGNYDNVRVEFKNKDLA DKYKDKYVDVFGANAYYQC AFSKKTNDINSHQTDKRKTC MYGGVTEHNGNQLDKYRSIT VRVFEDGKNLL SPDVQINKK KVTAQELDYLTRHYLVKNKK LYEFNNSPYETGYIKFIENENS FWYDMMPAPGDKFDQ SKYL MMYNDNKMVDSKDVKIEVY LTTKKKGGGGSMAQDIISTIG DLVKWIIDTVNKFTKK. | 29 | CATATGGCAGATAGCGACATCAACAT CAAGACGGGCACGACGGACATTGGCT CAAACACGACGGTGAAAACGGGTGAC CTGGTTACCTACGATAAAGAAAACGG CATGCATAAGAAGGTGTTTTATTCTTT CATCGATGACAAAAACCACAATAAAA AGCTGCTGGTTATTCGTACCAAGGGT ACGATTGCGGGCGGTGGCGGTAGTGA ATCCCAGCCGGACCCGAAACCGGACG AACTGCATAAGAGCTCTAAATTTACC GGCCTGATGGAAAATATGAAAGTGCT GTATGATGACAACCACGTCTCAGCCA TTAATGTGAAATCGATCGATCAATTTC GTTATTTCGACCTGATTTACAGCATCA AGGATACCAAACTGGGCAACTACGAC AATGTGCGCGTTGAATTTAAAAACAA GGATCTGGCAGACAAATATAAGGATA AATACGTCGACGTGTTTGGTGCGAAT GCCTATTACCAGTGCGCTTTCAGTAAA AAGACCAACGATATCAACTCCCATCA AACCGACAAGCGTAAAACGTGTATGT ATGGCGGTGTCACCGAACACAACGGC AATCAGCTGGATAAATACCGTTCAAT CACGGTTCGCGTCTTTGAAGATGGTA AAAACCTGCTGTCGTTCGATGTTCAGA CCAATAAAAAGAAAGTCACGGCACA GAACTGGATTATCTGACCCGCCATTAC CTGGTTAAGAACAAGAAGCTGTACGA ATTCAACAACAGTCCGTATGAAACGG GCTACATCAAGTTCATCGAAAACGAA AACAGCTTCTGGTACGATATGATGCC GGCACCGGGTGATAAGTTCGACCAGA | 31 |

TABLE 5 -continued

| AT62 FUSION OLIGOPEPTIDES | | | |
|---|---|---|---|
| Fusion Peptide Amino Acid Sequence | SEQ ID NO | Codon-Optimized Nucleic Acid Sequence | SEQ ID NO |
| | | GCAAGTACCTGATGATGTACAACGAT AACAAGATGGTTGATTCTAAGGACGT GAAAATCGAAGTTTATCTGACCACGA AGAAAAAGGGCGGTGGCGGTAGCATG GCTCAAGATATTATCTCTACCATCGGT GACCTGGTGAAGTGGATTATTGACAC GGTGAACAAGTTTACGAAGAAATGAG GATCC | |

Example 4

Immunogenicity of Fusion Constructs

The immunogenicity of two of the fusion constructs (AT62_DT and AT62_PSM) along with control (AT62 AA) was tested in Swiss Webster mice in groups of 4, 4 and 8 mice respectively. Mice were immunized subcutaneously with the proteins (10 μg) along with adjuvant (Sigma Adj System; an MPL based adjuvant) (5 μg) three times at two week intervals (days 0, 14 & 28). After the third immunization the mice were boosted with the respective δ-toxin or PSMα3 peptide (10 μg) and serum samples collected from the mice were tested for binding to the antigen using ELISA as described before (Adhikari, et al., 2012, PLoS *One,* 7 (6):e38567). Briefly, 96-well plates were coated with 100 ng/well of full length alpha toxin (List Biological Laboratories, Campbell, Calif.), PSMα3, or delta toxin overnight at 4° C. Plates were blocked with Starting Block buffer (Thermo Scientific) for one hour at room temperature (RT). Serum samples were diluted at 1:100 using starting block buffer as diluent. Plates were washed three times and sample dilutions were applied at 100 μl/well. Plates were incubated for one hour at RT and washed three times before applying the conjugate, goat anti-mouse IgG (H&L)-HRP (Horse Radish Peroxidase) in starting block buffer. Plates were incubated for one hour at RT, washed as described above and incubated with TMB (3,3',5,5'-tetramethylbenzidine) to detect HRP for 30 min. Optical density at 650 nm was measured using a Versamax™ plate reader (Molecular Devices CA).

As shown in FIG. 6, mice vaccinated with the fusion constructs AT62-PSM and AT62-DT showed strong antibody response to alpha hemolysin showing that the AT62 retained its immunogenicity in the context of fusion construct. Response to PSMα3 and δ-toxin peptides was also detectable although at a lower level. These data suggest that induction of an antibody response to both components is possible.

The following additional constructs will be constructed and tested:

- Fusion of a single PSMα3 or δ-toxin or 2, 3, 4, 5, or 6 tandem repeats of PSMα3 or δ-toxin (wild type or any of the mutants) at the N- or C-terminus of attenuated LukS-PV mutants as described in PCT/US12/67483.
- Fusion of a single PSMα3 or δ-toxin or 2, 3, 4, 5, or 6 tandem repeats of PSMα3 or 6-toxin (wild type or any of the mutants) at the N- or C-terminus of attenuated superantigen vaccines $SEB_{L45R/Y89A/Y94A}$, $SEA_{L48R/D70R/Y92A}$, or $TSST\text{-}1_{L30R/D27A/I46}$.
- Fusion of a single PSMα3 or δ-toxin or 2, 3, 4, 5, or 6 tandem repeats of PSMα3 or δ-toxin (wild type or any of the mutants) along with AT62 to any of the superantigen vaccines $SEB_{L45R/Y89A/Y94A}$, $SEA_{L48R/D70R/Y92A}$, or $TSST\text{-}1_{L30R/D27A/I46A}$.

An example of three potential fusion constructs is schematically shown in FIG. 7.

Example 5

Triple Fusion Mutant of Staphylococcal Superantigen Toxoids

The most prevalent *S. aureus* Superantigens (Sags) are SEB, SEC, SEA, and TSST-1. Recombinant vaccines for SEB, SEA, and TSST-1 (subject of U.S. Pat. Nos. 6,713,284; 6,399,332; 7,087,235; 7,750,132; 7,378,257, and 8,067,202) were developed and tested individually for protective efficacy in models of toxic shock syndrome (Bavari, et al., 1996, *J Infect Dis,; Bavari and Ulrich,* 1995, *Infect Immun,* 63 (2):423-429; Boles, et al., 2003 *Clin Immunol,* 108 (1):51-59; Boles, et al., 2003, *Vaccine,* 21 (21-22):2791-2796; Ulrich, et al., 1998, *Vaccine,* 16 (19):1857-1864). Whereas the SAgs play an important role in complications of SA disease, a major obstacle in developing vaccines based on SAgs is the fact that there are >20 variants of these toxins in various SA strains.

We evaluated the ability of human antibodies to SEB, SEA, and TSST-1 to neutralize a wide range of *S. aureus* Sags, by the following methods.

Affinity Purification of Human Anti-SAg Antibodies. SEA, SEB and TSST-1 were coupled to agarose beads (1 mg SAg per 1 mL bead volume) of an Aminolink® plus immobilization column (Thermo Scientific, Rockford, Ill.) following the manufacturer's protocol. Affinity purification of specific antibodies from IVIG (Omrix Biopharmaceuticals, Nes-Ziona, Israel) was carried out according to manufacturer's protocol with minor modifications: 50 mL of IVIG was incubated with toxin-coupled beads for 1 h 30 min at RT with gentle rocking, centrifuged, the supernatant removed and a fresh 50 mL of IVIG incubated with the beads for another 1 h and 30 min. Elution was performed with glycine HCl pH 2.5 buffer. To avoid degradation of proteins eluted fractions were collected in neutralizing buffer, containing (0.1 M Tris) pH 9 to give a final pH between 6-7. The concentration of the affinity purified antibodies was determined by BCA assay.

Toxin Neutralization Assay In Vitro. Peripheral blood mononuclear cells were isolated from heparinized blood of de-identified healthy human donors by Ficoll gradient centrifugation as described elsewhere (Berthold, 1981, *Blut,* 43

(6):367-371). Isolated peripheral blood mononuclear cells were washed twice in PBS, frozen in 10% DMSO in heat-inactivated fetal bovine serum (HI-FBS) overnight at −80° C., and stored in liquid nitrogen until further use. For the assay, cells were washed and re-suspended in RPMI 1640 medium, supplemented with 5% fetal bovine serum (FBS), non-essential amino acids, Penicillin/Streptomycin and L-Glutamine. Cells were, enumerated by Trypan blue exclusion and adjusted to $2 \times 10^6$ cells/ml. 75 µl of this cell suspension ($1.5 \times 10^5$ cells) with a viability of >95% was added the wells of a 96-well plate containing antibody/antigen mixes in duplicates as follows: 37.5 µl of affinity-purified anti-SEA, -SEB, -TSST-1, in semi-log dilutions (0.02-20 µg/ml) or IVIG in semi log dilutions (2.5-2500 µg/ml) IVIG and 37.5 µl of a 1 ng/ml preparation of either SEB, SEC1-3, SEE, SEH, SEI, SEK, TSST-1, SpeC, or 2 ng/ml of SED, or 3 ng/ml of SpeA. To test the synergistic activity of purified polyclonal Abs a combination of anti-SEA, -SEB, and -TSST-1 was used in a semi log dilution ranging from 0.02 to 20 µg/ml and the same amount of toxin as above. Wells containing medium with toxin only were served as positive controls. The plates were incubated at 37° C. in an atmosphere of 5% $CO_2$-95% air for 48 hours. Plates were centrifuged at 1600×g for 10 minutes, culture supernatants harvested and IFNγ concentration (pg/ml), was determined by ELISA (Human IFN-gamma DuoSet, R&D Systems, Minneapolis, Minn.) following the manufacturers' protocol. Plates were read at 450 nm using the Versamax plate reader and data was transferred to and analyzed in Excel. Positive control wells were considered to have a 0% IFNγ inhibition and, inhibition of IFNγ production in the presence of affinity purified antibodies was calculated as the difference in IFNγ concentration between the positive control and sample. $IC_{50}$ (the molar concentration of antibodies that was required to reach 50% inhibition of IFNγ production) values for the neutralizing agents (purified antibodies or IVIG) were determined using a 4-parameter logistic model (equation 205, XLfit version 5.2).

As shown in FIG. 8, affinity purified human antibodies (from IVIG) to each of these three toxins provided robust neutralization towards the homologous toxin and varying degree of cross neutralization to several other SAgs. However, a cocktail of the three human antibodies resulted in a remarkable widening of the cross neutralization activity.

In view of these results, novel fusions of the three toxoid superantigens: $SEB_{L45R/Y89A/Y94A}$, $SEA_{L48R/D70R/Y92A}$, and $TSST-1_{L30R/D27A/I46A}$ mutants are expressed as single molecules in a prokaryotic host, e.g., E. coli. Such fusion proteins can be superior to individual components riot only due to ease of manufacturing but also because they can enhance the elicitation of cross reactive antibodies between various superantigens as the common epitopes brought together into a single molecule can act in an immunodominant manner. The following fusion proteins are to be constructed.

A fusion of $SEB_{L45R/Y89A/Y94A}$, $SEA_{L48R/D70R/Y92A}$, and $TSST-1_{L30R/D27A/I46A}$ mutants in one of the following orders with a commonly used linker (L) such as but not limited to a linker consisting of one or more repeats of four glycines and one serine:

BAT Fusion:$SEB_{L45R/Y89A/Y94A}$-L-$SEA_{L48R/D70R/Y92A}$-L-$TSST-1_{L30R/D27A/I46A}$ BTA Fusion:$SEB_{L45R/Y89A/Y94A}$-L-$TSST-1_{L30R/D27A/I46A}$-L-$SEA_{L48R/D70R/Y92A}$ ABT Fusion:$SEA_{L48R/D70R/Y92A}$-L-$SEB_{L45R/Y89A/Y94A}$-L-$TSST-1_{L30R/D27A/I46A}$ ATB Fusion:$SEA_{L48R/D70R/Y92A}$-L-$TSST-1_{L30R/D27A/I46A}$-L-$SEB_{L45R/Y89A/Y94A}$ TAB Fusion:$TSST-1_{L30R/D27A/I46A}$-L-$SEA_{L48R/D70R/Y92A}$-L-$SEB_{L45R/Y89A/Y94A}$ TBA Fusion:$TSST-1_{L30R/D27A/I46A}$-L-$SEB_{L45R/Y89A/Y94A}$-L-$SEA_{L48R/D70R/Y92A}$ Representative sequences are presented in Table 6

TABLE 6

| SAG FUSION PROTEINS. | | |
|---|---|---|
| | | SEQ ID NO |
| BAT Fusion: $SEB_{L45R/Y89A/Y94A}$-L-$SEA_{L48R/D70R/Y92A}$-L-$TSST-1_{L30R/D27A/I46A}$ | MESQPDPKPDELHKSSKFTGLMENMKVLYDDNHVSAINVKSIDQFRYFDLIYSIKDT KLGNYDNVRVEFKNKDLADKYKDKYVDVFGANAYYQCAFSKKTNDINSHQTDKRKT CMYGGVTEHNGNQLDKYRSITVRVFEDGKNLLSFDVQTNKKKVTAQELDYLTRHYL VKNKKLYEFNNSPYETGYIKFIENENSFWYDMMPAPGDKFDQSKYLMMYNDNKM VDSKDVKIEVYLTTKKKGGGSEKSEEINEKDLRKKSELQGTALGNLKQIYYYNEKAKTE NKESHDQFRQHTILFKGFFTDHSWYNDLLVRFDSKDIVDKYKGKKVDLYGAYAGYQ CAGGTPNKTACMYGGVTLHDNNRLTEEKKVPINLWLDGKQNTVPLETVKTNKKNV TVQELDLQARRYLQEKYNLYNSDVFDGKVQRGLIVFHTSTEPSVNYDLFGAQGQYS NTLLRIYRDNKTINSENMHIDIYLYTSGGGGSSTNDNIKDLLDWYSSGSDTFTNSEVL ANSRGSMRIKNTDGSISLIAFPSPYYSPAFTKGEKVDLNTKRTKKSQHTSEGTYIHFQI SGVTNTEKLPTPIELPLKVKVHGKDSPLKYWPKFDKKQLAISTLDFEIRHQLTQIHGLY RSSDKTGGYWKITMNDGSTYQSDLSKKFEYNTEKPPINIDEIKTIEAEIN | 32 |
| BTA Fusion:$SEB_{L45R/Y89A/Y94A}$-L-$TSST-1_{L30R/D27A/I46A}$-L-$SEA_{L48R/D70R/Y92A}$ | MESQPDPKPDELHKSSKFTGLMENMKVLYDDNHVSAINVKSIDQFRYFDLIYSIKDT KLGNYDNVRVEFKNKDLADKYKDKYVDVFGANAYYQCAFSKKTNDINSHQTDKRKT CMYGGVTEHNGNQLDKYRSITVRVFEDGKNLLSFDVQTNKKKVTAQELDYLTRHYL VKNKKLYEFNNSPYETGYIKFIENENSFWYDMMPAPGDKFDQSKYLMMYNDNKM VDSKDVKIEVYLTTKKKGGGSSTNDNIKDLLDWYSSGSDTFTNSEVLANSRGSMRIK NTDGSISLIAFPSPYYSPAFTKGEKVDLNTKRTKKSQHTSEGTYIHFQISGVTNTEKLPT PIELPLKVKVHGKDSPLKYWPKFDKKQLAISTLDFEIRHQLTQIFIGLYRSSDKTGGYW KITMNDGSTYQSDLSKKFEYNTEKPPINIDEIKTIEAEINGGGGSEKSEEINEKDLRKKS ELQGTALGNLKQIYYYNEKAKTENKESHDQFRQHTILFKGFFTDHSWYNDLLVRFDS KDIVDKYKGKKVDLYGAYAGYQCAGGTPNKTACMYGGVTLHDNNRLTEEKKVPINL WLDGKQNTVPLETVKTNKKNVTVQELDLQARRYLQEKYNLYNSDVFDGKVQRGLIV FHTSTEPSVNYDLFGAQGQYSNTLLRIYRDNKTINSENMHIDIYLYTS | 33 |

TABLE 6-continued

SAG FUSION PROTEINS.

| | | SEQ ID NO |
|---|---|---|
| ABT Fusion: SEA$_{L48R/D70R/Y92A}$-L-SEB$_{L45R/Y89A/Y94A}$-L-TSST-1$_{L30R/D27A/I46A}$ | MEKSEEINEKDLRKKSELQGTALGNLKQIYYYNEKAKTENKESHDQFRQHTILFKGFF TDHSWYNDLLVRFDSKDIVDKYKGKKVDLYGAYAGYQCAGGTPNKTACMYGGVTL HDNNRLTEEKKVPINLWLDGKQNTVPLETVKTNKKNVTVQELDLQARRYLQEKYNL YNSDVFDGKVQRGLIVFHTSTEPSVNYDLFGAQGQYSNTLLRIYRDNKTINSENMHI DIYLYTSGGGGSESQPDPKPDELHKSSKFTGLMENMKVLYDDNHVSAINVKSIDQFR YFDLIYSIKDTKLGNYDNVRVEFKNKDLADKYKDKYVDVFGANAYYQCAFSKKTNDI NSHQTDKRKTCMYGGVTEHNGNQLDKYRSITVRVFEDGKNLLSFDVQTNKKKVTA QELDYLTRHYLVKNKKLYEFNNSPYETGYIKFIENENSFWYDMMPAPGDKFDQSKYL MMYNDNKMVDSKDVKIEVYLTTKKKGGGSSTNDNIKDLLDWYSSGSDTFTNSEVL ANSRGSMRIKNTDGSISLIAFPSPYYSPAFTKGEKVDLNTKRTKKSQHTSEGTYIHFQI SGVTNTEKLPTPIELPLKVKVHGKDSPLKYWPKFDKKQLAISTLDFEIRHQLTQIFIGLY RSSDKTGGYWKITMNDGSTYQSDLSKKFEYNTEKPPINIDEIKTIEAEIN | 34 |
| ATB Fusion: SEA$_{L48R/D70R/Y92A}$-L-TSST-1$_{L30R/D27A/I46A}$-L-SEB$_{L45R/Y89A/Y94A}$ | MEKSEEINEKDLRKKSELQGTALGNLKQIYYYNEKAKTENKESHDQFRQHTILFKGFF TDHSWYNDLLVRFDSKDIVDKYKGKKVDLYGAYAGYQCAGGTPNKTACMYGGVTL HDNNRLTEEKKVPINLWLDGKQNTVPLETVKTNKKNVTVQELDLQARRYLQEKYNL YNSDVFDGKVQRGLIVFHTSTEPSVNYDLFGAQGQYSNTLLRIYRDNKTINSENMHI DIYLYTSGGGGSSTNDNIKDLLDWYSSGSDTFTNSEVLANSRGSMRIKNTDGSISLIAF PSPYYSPAFTKGEKVDLNTKRTKKSQHTSEGTYIHFQISGVINTEKLPTPIELPLKVKVH GKDSPLKYWPKFDKKCLLAISTLDFEIRHQLTQINGLYRSSDKTGGYWKITMNDGSTY QSDLSKKFEYNTEKPPINIDEIKTIEAEINGGGSESQPDPKPDELHKSSKFTGLMENMK VLYDDNHVSAINVKSIDQFRYFDLIYSIKDTKLGNYDNVRVEFKNKDLADKYKDKYVD VFGANAYYQCAFSKKTNDINSHQTDKRKTCMYGGVTEHNGNQLDKYRSITVRVFE DGKNLLSFDVQTNKKKVTAQELDYLTRHYLVKNKKLYEFNNSPYETGYIKFIENENSF WYDMMPAPGDKFDQSKYLMMYNDNKMVDSKDVKIEVYLTTKKK | 35 |
| TAB Fusion: TSST-1$_{L30R/D27A/I46A}$-L-SEA$_{L48R/D70R/Y92A}$-L-SEB$_{L45R/Y89A/Y94A}$ | MSTNDNIKDLLDWYSSGSDTFTNSEVLANSRGSMRIKNTDGSISLIAFPSPYYSPAFT KGEKVDLNTKRTKKSQHTSEGTYIHFQISGVTNTEKLPTPIELPLKVKVHGKDSPLKY WPKFDKKQLAISTLDFEIRHQLTQIHGLYRSSDKTGGYWKITMNDGSTYQSDLSKKF EYNTEKPPINIDEIKTIEAEINGGGSEKSEEINEKDLRKKSELQGTALGNLKQIYYYNEK AKTENKESHDQFRQHTILFKGFFTDHSWYNDLLVRFDSKDIVDKYKGKKVDLYGAYA GYQCAGGTPNKTACMYGGVTLHDNNRLTEEKKVPINLWLDGKQNTVPLETVKTNK KNVfVQELDLQARRYLQEKYNLYNSDVFDGKVQRGLIVFHTSTEPSVNYDLFGAQG QYSNTLLRIYRDNKTINSENMHIDIYLYTSGGGGSESQPDPKPDELHKSSKFTGLMEN MKVLYDDNHVSAINVKSIDQFRYFDLIYSIKDTKLGNYDNVRVEFKNKDLADKYKDKY VDVFGANAYYQCAFSKKTNDINSHQTDKRKTCMYGGVTEHNGNQLDKYRSITVRV FEDGKNLLSFDVQTNKKKVTAQELDYLTRHYLVKNKKLYEFNNSPYETGYIKFIENENS FWYDMMPAPGDKFDQSKYLMMYNDNKMVDSKDVKIEVYLTTKKK | 36 |
| TBA Fusion: TSST-1$_{L30R/D27A/I46A}$-L-SEB$_{L48R/D70R/Y94A}$-L-SEA$_{L48R/D70R/Y92A}$ | MSTNDNIKDLLDWYSSGSDTFTNSEVLANSRGSMRIKNTDGSISLIAFPSPYYSPAFT KGEKVDLNTKRTKKSQHTSEGTYIHFQISGVTNTEKLPTPIELPLKVKVHGKDSPLKY WPKFDKKCLLAISTLDFEIRHQLTQIHGLYRSSDKTGGYWKITMNDGSTYQSDLSKKF EYNTEKPPINIDEIKTIEAEINGGGGSESQPDPKPDELHKSSKFTGLMENMKVLYDDN HVSAINVKSIDQFRYFDLIYSIKDTKLGNYDNVRVEFKNKDLADKYKDKYVDVFGANA YYQCAFSKKTNDINSHQTDKRKTCMYGGVTEHNGNQLDKYRSITVRVFEDGKNLLS FDVQTNKKKVTAQELDYLTRHYLVKNKKLYEFNNSPYETGYIKFIENENSFWYDMM PAPGDKFDQSKYLMMYNDNKMVDSKDVKIEVYLTTKKKGGGSEKSEEINEKDLRKK SELQGTALGNLKQIYYYNEKAKTENKESHDQFRQHTILFKGFFTDHSWYNDLLVRFD SKDIVDKYKGKKVDLYGAYAGYQCAGGTPNKTACMYGGVTLHDNNRLTEEKKVPIN LWLDGKQNTVPLETVKINKKNVIVQELDLQARRYLQEKYNLYNSDVFDGKVQRGLI VFHTSTEPSVNYDLFGAQGQYSNTLLRIYRDNKTINSENMHIDIYLYTS | 37 |

What is claimed is:

1. A multivalent oligopeptide, comprising a fusion of three or more *Staphylococcus aureus*-derived peptides, or mutants, fragments, variants, or derivatives thereof arranged in any order, wherein the multivalent oligopeptide comprises three or more superantigen (SAg) polypeptides, or mutants, fragments, variants, or derivatives thereof, and wherein three of the three or more SAg polypeptides, or mutants, fragments, variants, or derivatives thereof comprise SEQ ID NO: 49, SEQ ID NO: 50, and SEQ ID NO: 51.

2. The oligopeptide of claim 1, wherein the three or more *Staphylococcus aureus*-derived peptides, or mutants, fragments, variants, or derivatives thereof are associated via linkers.

3. The oligopeptide of claim 1, comprising the amino acid sequence SEQ ID NO: 32, SEQ ID NO: 33, SEQ ID NO. 34, SEQ ID NO: 35, SEQ ID NO: 36, SEQ ID NO: 37, or any combination thereof.

4. The oligopeptide of claim 1, further comprising a heterologous peptide or polypeptide.

5. The oligopeptide of claim 1, further comprising an immunogenic carbohydrate.

6. A composition comprising the oligopeptide of claim 1, and a carrier.

7. The composition of claim 6, further comprising an adjuvant.

8. The composition of claim 6, further comprising an immunogen.

9. A method of inducing a host immune response against *Staphylococcus aureus*, comprising administering to a subject in need of the immune response an effective amount of the composition of claim 6.

10. A method of treating a Staphylococcal disease or infection in a subject comprising administering to a subject in need thereof the composition of claim 6.

11. A method of producing a vaccine against *S. aureus* infection comprising:

isolating the oligopeptide of claim 1 and combining the oligopeptide with an adjuvant.

* * * * *